United States Patent
Sammis et al.

(10) Patent No.: US 12,264,143 B2
(45) Date of Patent: Apr. 1, 2025

(54) SYNTHESIS OF CANNABINOIDS AND CANNABINOID PRECURSORS, AND RELATED COMPOUNDS, FORMULATIONS, AND METHODS OF USE

(71) Applicant: Nalu Bio, Inc., San Francisco, CA (US)

(72) Inventors: Glenn M. Sammis, Vancouver (CA); Markus Roggen, Vancouver (CA)

(73) Assignee: Nalu Bio, Inc., San Francisco, CA (US)

( * ) Notice: Subject to any disclaimer, the term of this patent is extended or adjusted under 35 U.S.C. 154(b) by 0 days.

(21) Appl. No.: 18/750,852

(22) Filed: Jun. 21, 2024

(65) Prior Publication Data

US 2024/0368108 A1    Nov. 7, 2024

Related U.S. Application Data

(63) Continuation of application No. 18/212,061, filed on Jun. 20, 2023, which is a continuation-in-part of application No. PCT/US2021/064243, filed on Dec. 17, 2021.

(60) Provisional application No. 63/126,923, filed on Dec. 17, 2020.

(51) Int. Cl.
  *C07D 311/80* (2006.01)
  *A61K 31/00* (2006.01)
  *C07C 39/23* (2006.01)
  *C07C 215/50* (2006.01)
  *C07D 311/78* (2006.01)

(52) U.S. Cl.
  CPC .......... *C07D 311/80* (2013.01); *A61K 31/658* (2023.05); *C07C 39/23* (2013.01); *C07C 215/50* (2013.01); *C07D 311/78* (2013.01)

(58) Field of Classification Search
  CPC .................................................. C07D 311/80
  See application file for complete search history.

(56) References Cited

U.S. PATENT DOCUMENTS

| | | | |
|---|---|---|---|
| 7,186,850 | B2 | 3/2007 | Silverberg |
| 10,053,407 | B2 | 8/2018 | Dickman et al. |
| 10,059,683 | B2 | 8/2018 | Dialer et al. |
| 10,399,920 | B2 | 9/2019 | Dickman et al. |
| 2017/0283837 | A1 | 10/2017 | Kavarana et al. |
| 2020/0079715 | A1 | 3/2020 | Davis et al. |
| 2020/0325091 | A1 | 10/2020 | Porco et al. |
| 2022/0204431 | A1 | 6/2022 | Shen et al. |

FOREIGN PATENT DOCUMENTS

| | | |
|---|---|---|
| WO | 2014062965 A1 | 4/2014 |
| WO | 2019046806 A1 | 3/2019 |
| WO | 2020102901 A1 | 11/2019 |
| WO | 2020031179 A1 | 2/2020 |
| WO | 2020099283 A1 | 5/2020 |
| WO | 2020229891 A1 | 11/2020 |
| WO | 2021007661 A1 | 1/2021 |

OTHER PUBLICATIONS

Furstner et al. (Angew. Chem. Int. Ed., vol. 41 (4), pp. 609-612 (2002)).*
CAPLUS Abstract—Bezmenova and Kamakin, "Reaction of Sulfolane and its derivatives with a Grignard Reagent" Khimiya Seraorganicheskikh Soedinenii, Soderzhashchikhsya v Neftyakh i Nefteproduktakh, vol. 8, pp. 140-144 (1968).*
Oda and Yamamoto, "Reaction of Dimethyl Sulfoxide with Grignard Reagents" (J. Org. Chem. vol. 26, pp. 4679-4681 (1961)).*
Gong et al., "Synthesis of CBD and Its Derivatives Bearing Various C4'-Side Chains with a Late-Stage Diversification Method," J. Org. Chem. 2020, 85, 2704-2715.
Kinney et al., "Discovery of KLS-13019, a Cannabidiol-Derived Neuroprotective Agent, with Improved Potency, Safety, and Permeability," ACS Med. Chem. Lett. 2016, 7, 424-428.
Qi et al., "Delta9-Tetrahydrocannabinol Immunochemical Studies: Haptens, Monoclonal Antibodies, and a Convenient Synthesis of Radiolabeled Delta9-Tetrahydrocannabinol," J. Med. Chem. 2005, 48, 7389-7399.
Ben-Shabat et al. (2006), "New Cannabidiol Derivatives: Synthesis, Binding to Cannabinoid Receptor, and Evaluation of their Antiinflammatory Activity," J. Med. Chem. 49: 1113-1117.
Barker et al., "The Synthesis of Olivetol. Trimethylsilation as a Protective Group During Grignard Reactions," Organic Prep. and Procedures Int'l: The New J. Org. Synth. 11(2): 87-92.
Campeau et al. (2019), "Cross-Coupling and Related Reactions: Connecting Past Success to the Development of New Reactions for the Future," Organometallics 38(1): 3-35.
Götz (2019), "Structure-Effect Relationships of Novel Semi-Synthetic Cannabinoid Derivatives," Frontiers in Pharmacology 10: 1284.
Haj et al. (2015), "HU-444, a Novel, Potent Anti-Inflammatory, Nonpsychotropic Cannabinoid," J. Pharmacol. Exper. Ther. 355: 66-75.
Heiskanen et al. (2008), "4-Aryl-8-hydroxyquinolines from 4-chloro-8-tosyloxyquinoline using a Suzuki-Miyaura Cross-Coupling Approach," Tetrahedron 65: 518-524.
Jung et al. (2019), "Synthetic Strategies for (-)-Cannabidiol and its Structural Analogs," Chem. Asian J. 14:3749-3762.

(Continued)

*Primary Examiner* — Valerie Rodriguez-Garcia
(74) *Attorney, Agent, or Firm* — Dianne E. Reed; VLP Law Group LLP

(57) ABSTRACT

Methods are provided for the synthesis of cannabinoids, including cannabidiol (CBD), cannabinol (CBN), cannabichromene (CBC), cannabidiolic acid (CBDA), cannabigerol (CBG), cannabigerolic acid (CBGA), cannabidivarin (CBDV), cannabidibutol (CBD-C4), dihydrocannabidiol (DCBD), tetrahydrocannabivarin (THCV), analogs thereof, and precursors to the foregoing. One method employs phloroglucinol or a phloroglucinol analog as a starting material. The syntheses are stereospecific, efficient, selective, and cost-effective, with little or no potential for generation of THC ((−)-trans-$\Delta^9$-tetrahydro-cannabinol) or any other psychoactive side product. Telescoped syntheses are also provided, as are new cannabinoids, pharmaceutical formulations, and methods of use.

12 Claims, No Drawings

(56) References Cited

OTHER PUBLICATIONS

Lago-Fernandez et al. (2017), "New Methods for the Synthesis of Cannabidiol Derivatives," Methods in Enzymology 593: 237-257.
Morales et al. (2017), "An Overview on Medicinal Chemistry of Synthetic and Natural Derivatives of Cannabidiol," Frontiers in Pharmacology 8(422): 1-18.
Seltzman et al. (1991), "Synthesis of Nona-Deutero Olivetol and Nona-Deutero Cannabinoids," J. Labeled Compounds and Radiopharm. XXIX(9): 1009-1018.
Stern et al. (2007), "Medicinal Chemistry Endeavors around the Phytocannabinoids," Chemistry & Biodiversity 4: 1707-1728.
Mechoulam et al. (2002), "Cannabidiol: an overview of some chemical and pharmacological aspects. Part I: chemical aspects," Chem. Phys. Lipids 121: 35-43.

* cited by examiner

SYNTHESIS OF CANNABINOIDS AND CANNABINOID PRECURSORS, AND RELATED COMPOUNDS, FORMULATIONS, AND METHODS OF USE

CROSS-REFERENCE TO RELATED APPLICATIONS

This application is a continuation of U.S. application Ser. No. 18/212,061, filed Jun. 20, 2023, which is a continuation-in-part of PCT Application No. PCT/US2021/064243, having an International Filing Date of Dec. 17, 2021 and claims priority to provisional U.S. Application Ser. No. 63/126,923, filed Dec. 17, 2020. The disclosures of the aforementioned patent applications are incorporated by reference in their entireties.

TECHNICAL FIELD

The present invention relates generally to methods for chemically synthesizing cannabinoids, including cannabidiol (CBD) and analogs thereof, to compounds and compositions employed in and generated by the synthetic methods, to methods for synthesizing the reactants used, and to methods for using the synthesized compounds. The invention has utility in the fields of medicine, medicinal chemistry, therapeutics, and chemical and pharmaceutical manufacturing.

BACKGROUND

Medical *cannabis* and individual cannabinoids, such as THC ((−)-trans-Δ$^9$-tetrahydro-cannabinol) and CBD (cannabidiol), are receiving growing attention in the media and the scientific literature. In particular, CBD, the second most abundant component of the *Cannabis sativa* (*C. Sativa*) plant and a non-psychoactive phytocannabinoid, is known to have a number of beneficial properties and a wide range of potential therapeutic uses. Anti-oxidant, anti-inflammatory, and neuroprotective effects are among the many documented properties of CBD, and established and proposed uses range from alleviation of pain and anxiety to the treatment of cancer, neurodegenerative diseases, and seizure disorders. It has also been suggested that CBD has the potential to offset the side effects of other pharmaceuticals, including chemotherapy drugs and opioid-based analgesics. The considerable physiological significance of CBD has generated substantial interest in its pharmacotherapy potential.

CBD is a chiral 21-carbon terpenophenolic cannabinoid that is biosynthesized in the plant by decarboxylation of its immediate precursor, cannabidiolic acid. "Cannabidiol" is the term usually used to refer to the (−)-enantiomer shown below, i.e. (−)-cannabidiol:

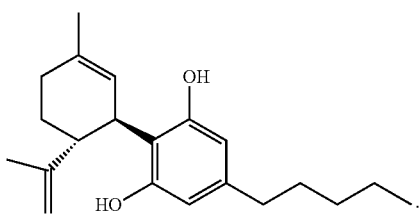 [SMILES: C=C(C)[C@@H]1CCC(C)=C[C@H]1c1c(O)cc(CCCCC)cc1O]

In a 2018 World Health Organization ("WHO") Critical Review, pure CBD was reported to be well-tolerated with a good safety profile, exhibiting no evidence of abuse or dependency potential, even at high doses.

CBD and other naturally occurring cannabinoids have been obtained primarily by extraction, isolation, and purification from *C. Sativa* and industrial hemps, cultivars that are used to manufacture fiber and oilseed. This has proven difficult primarily because of the chemical and physical similarities among the many phytocannabinoids present in the natural source, making isolation of CBD from *C. Sativa* and hemp a complex process, leading to quality control challenges in commercial manufacturing. See Lo et al. (2019) *Nature* 567: 123-126.

In order to ensure a reliable supply of CBD with consistent quality and avoid contamination of the product with impurities and toxins absorbed from soil, scientists have explored the possibility of chemically synthesizing CBD and other known and new cannabinoids. One of the earliest reported synthetic strategies for preparation of racemic CBD (i.e., +CBD) is that of Mechoulam et al. (1965) *J. Am. Chem. Soc.* 87: 3273-75, a multistep method that begins with the electrophilic addition of citral A to 1,3-dimethoxy-olivetol and concludes with the high temperature demethylation of the two methoxy groups in the penultimate intermediate to provide CBD as a racemic mixture of enantiomers.

The first direct, stereoselective synthesis of the desired enantiomer, (−)-CBD, was reported by Petrzilka et al. (Petrzilka et al. (1967) *Helv. Chim. Acta* 50: 719-23 and Petrzilka et al. (1967) *Helv. Chim. Acta* 50: 2111-13) and involves an electrophilic aromatic substitution reaction between olivetol and optically pure Δ$^9$-2,8-menthadien-1-ol. These reactants are costly to obtain and make for a very expensive synthetic process. Furthermore, and as may be seen below, the reaction exhibited poor regioselectivity, with the two reactive sites on the olivetol ring resulting in a mixture of three products, with only 25% of the mixture composed of (−)-CBD.

The Petrzilka et al. reactants:

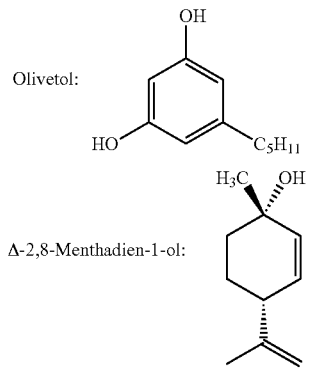

Petrzilka et al. reaction product composition:

(−)-CBD, 25%;

Unreacted olivetol, 30%;

Abnormal CBD (Abn-CBD), 35%

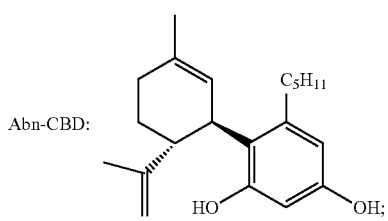

Abn-CBD:

and
(−)-2,4-di-substituted olivetol ("bis-CBD," 5%)

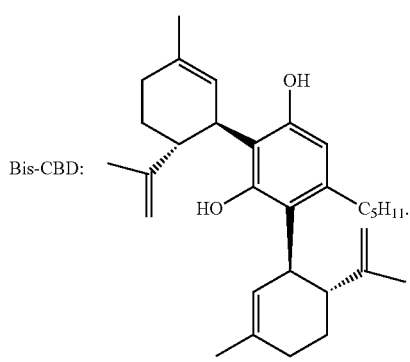

Bis-CBD:

See Jung et al. (2019), "Synthetic Strategies for (−)-Cannabidiol and Its Structural Analogs," *Chem. Asian J.* 14: 3749-62, discussing Petrzilka et al. (1967).

Subsequent attempts to improve on these two syntheses followed, including the boron trifluoride catalyzed synthesis of Razdan et al. (1974) *J. Am. Chem. Soc.* 98:5860-65, Rickards et al. (1984) *J. Org. Chem.* 49: 572-3, and Baek et al. (1985) *Tetrahedron: Asymmetry* 26: 1083-86; the $S_N2$ and 1,4-addition approach of Kobayashi et al. (2006) *Org. Lett.* 8:2699-702 (also see Kobayashi et al. (2002) *J. Org. Chem.* 67:8771-82; and Kobayashi et al. (2001) *Org. Lett.* 3:2017-20); the complicated, multifaceted approach of Shultz et al. (2018) *Org. Lett.* 20:381-84), which combines enzyme-catalyzed synthesis and resolution of a racemic reactant, an enantioselective enone reduction, a stereospecific rearrangement, and a ruthenium catalyzed ring-closing metathesis reaction. A more recent synthesis is suggested in International Patent Publication No. WO 2019/046806 A1 to Bencivenga et al., which describes a Lewis acid-catalyzed reaction between olivetol and menthadienol, exposure of the reaction mixture to a second reaction mixture containing a terpene, and phase separation to generate the desired product. U.S. Pat. No. 10,059,683 to Dialer et al. also describes a CBD synthesis analogous to the Petrzilka et al. method between olivetol and menthadienol but requiring the use of a di-halogenated olivetol compound as starting material.

There remains a need in the art for an efficient, cost-effective stereoselective synthesis of cannabinoids, including, but not limited to, CBD and CBD analogs. An ideal stereospecific synthesis would provide a number of advantages relative to cannabinoid syntheses developed to date. In particular, an ideal synthesis would:

provide a reaction product composition with a high percentage of the desired cannabinoid, with the presence of other reaction products minimized;

allow for straightforward separation of the desired product;

provide the desired product in high yield;

enable the of use mild reaction conditions, without need for harsh reagents or special precautions;

be efficient, without requiring numerous or time-consuming reaction steps, and without need to isolate and purify intermediates between steps;

eliminate or significantly reduce any incidental production of THC;

be easily adapted to produce CBD per se, CBD analogs, and other cannabinoids;

allow for a one-pot synthesis, without isolation of intermediates between steps; and be economical, making use of low cost, commercially available reactants or including cost-effective methods for the chemical synthesis of reactants.

SUMMARY OF THE INVENTION

The present invention is addressed to the above needs in the art and, in one embodiment, provides a method for synthesizing a plurality of cannabinoids, including, without limitation, CBD, cannabinol (CBN), cannabichromene (CBC), cannabidiolic acid (CBDA), cannabigerol (CBG), cannabigerolic acid (CBGA), cannabidivarin (CBDV), cannabidibutol (CBD-$C_4$), dihydrocannabidiol (DCBD), tetrahydrocannabivarin (THCV), analogs thereof, and synthetic precursors to the aforementioned compounds. The methods are stereospecific, efficient, cost-effective, and readily adapted to produce cannabinoids such as CBD and CBD precursors, as well as a host of other cannabinoids, cannabinoid precursors, and cannabinoid analogs, with little or no incidental generation of THC or other psychoactive side-products. In some embodiments, the synthetic method can be carried out as a "one pot" reaction, i.e., without isolation of intermediates between reaction steps.

In other embodiments, the invention provides novel cannabinoids. In other embodiments, pharmaceutical formulations are provided that comprise a cannabinoid that can be synthesized using the presently disclosed methods. In further embodiments, the invention provides methods of using the cannabinoids or pharmaceutical formulations thereof, wherein the methods involve administration of a cannabinoid or formulation thereof to a subject to provide a beneficial effect.

In a first embodiment, then, the invention provides a method for synthesizing olivetol or an analog thereof from a suitably substituted phloroglucinol reactant. Olivetol and olivetol analogs that are produced using the method can be used as reactants in a number of chemical syntheses (including in methods for synthesizing cannabinoids as described in detail elsewhere herein) and have the structure of formula (AA)

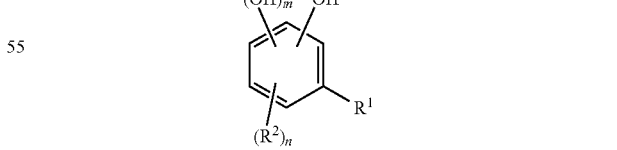

(AA)

wherein:
m is z 1;
n is zero, 1, or 2;
$R^1$ is selected from $C_1$-$C_{18}$ hydrocarbyl, substituted $C_1$-$C_{18}$ hydrocarbyl, heteroatom-containing $C_1$-$C_{18}$ hydrocarbyl, and substituted heteroatom-containing $C_1$-$C_{18}$ hydrocarbyl; and $R^2$ is selected from $C_1$-$C_{18}$ hydrocarbyl, substituted $C_1$-$C_{18}$ hydrocarbyl, heteroatom-containing $C_1$-$C_{18}$ hydrocarbyl, substituted heteroatom-containing $C_1$-$C_{18}$ hydrocarbyl, and functional groups, and when n is 2, the $R^2$ may be the same or different, and any $R^2$ on adjacent carbon atoms may be linked to form a cyclic structure, wherein the method comprises:

(a) reacting a phloroglucinol reactant having the structure of formula (AA-1)

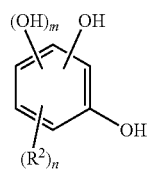

(AA-1)

with an electron-withdrawing hydroxyl-protecting reagent under conditions effective to provide a hydroxyl-protected intermediate having the structure of formula (AA-2)

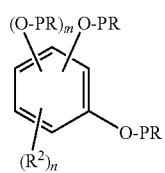

(AA-2)

in which PR represents an electron-withdrawing hydroxyl protecting group;

(b) effecting a cross-coupling reaction between the hydroxyl-protected intermediate (AA-2) and a reactant $R^1$-M in the presence of a catalyst that facilitates the cross-coupling reaction, wherein M comprises a metallic element, to provide a compound having the structure (AA-3)

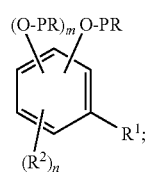

(AA-3)

(c) hydrolyzing (AA-3) to remove the hydroxyl protecting groups and provide a reaction product composition comprising compound (AA).

In another embodiment, a method is provided for synthesizing a cannabinoid, where the method comprises:
(a) synthesizing a compound having the structure of formula (AA) according to the method described above, to serve as a first reactant;
(b) contacting (AA) with a second reactant having the structure of formula (CC-1)

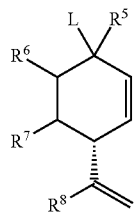

(CC-1)

wherein $R^5$ is H, carboxyl, $C_2$-$C_6$ acyloxy, $C_2$-$C_6$ alkoxycarbonyl, $C_1$-$C_6$ alkyl, or $C_1$-$C_6$ alkyl substituted with hydroxyl, carboxyl, or halo; $R^6$ and $R^7$ are independently selected from H, $C_1$-$C_{12}$ hydrocarbyl, substituted $C_1$-$C_{12}$ hydrocarbyl, heteroatom-containing $C_1$-$C_{12}$ hydrocarbyl, substituted heteroatom-containing $C_1$-$C_{12}$ hydrocarbyl, and functional groups; $R^8$ is methyl, hydroxymethyl, or halomethyl; and L is a leaving group, in the presence of a Lewis acid catalyst under reaction conditions effective to result in cross-coupling of reactants (AA) and (CC-1) and thereby provide a reaction product composition comprising a cannabinoid, the cannabinoid having the structure of formula (CC)

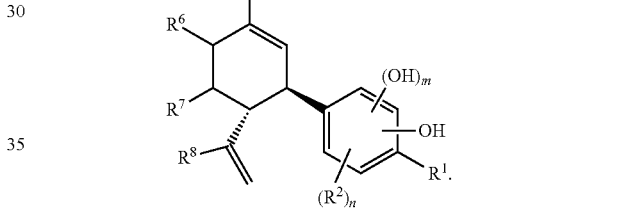

(CC)

It will be appreciated that when $R^5$ and $R^8$ are methyl, $R^6$ and $R^7$ are H, and L is hydroxyl, the compound having the structure of formula (CC-1) is (1S,4R)-p-mentha-2,8-dien-1-ol (hereafter referred to as "p-menthadienol").

In some embodiments, when $R^1$ is n-pentyl, when the cannabinoid product (CC) is CBD or analog thereof. In some embodiments, when $R^1$ is n-propyl, cannabinoid (CC) is CBDV or an analog thereof. In some embodiments, when $R^1$ is methyl, cannabinoid (CC) is CBD-$C_1$ or an analog thereof. In some embodiments, when $R^1$ is n-butyl, cannabinoid (CC) is cannabidibutol, i.e., CBD-$C_4$, or an analog thereof.

In a related embodiment, a method is provided for synthesizing tetrahydrocannabivarin (THCV) or an analog thereof. The method proceeds as above with the proviso that $R^1$ is n-propyl, such that compound (AA) is optionally substituted divarinol, such that the resulting cannabinoid is CBDV or an analog thereof. The reaction product can then be cyclized using conventional means to provide THCV or a substituted analog thereof.

In other embodiments, methods for synthesizing other cannabinoids, including, without limitation, CBN, CBDA, CBG, CBGA, and analogs of any of the foregoing are also provided.

In a further embodiment, cannabinoids, including CBD analogs, are provided as novel compounds having the structure of formula (EE)

(EE)

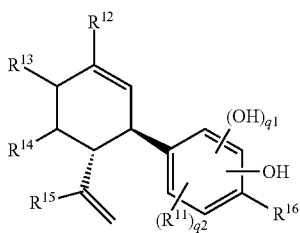

wherein:
q1 is zero or 1, and q2 is zero, 1, or 2;
$R^{11}$ is selected from $C_1$-$C_{12}$ hydrocarbyl, substituted $C_1$-$C_{12}$ hydrocarbyl, heteroatom-containing $C_1$-$C_{12}$ hydrocarbyl, substituted heteroatom-containing $C_1$-$C_{12}$ hydrocarbyl, and functional groups, and wherein when n is 2, the $R^{11}$ may be the same or different and any two $R^{11}$ bound to adjacent carbon atoms may be taken together to form a cyclic structure selected from a five-membered ring and a six-membered ring, optionally fused to an additional five-membered or six-membered ring, wherein the rings are aromatic, alicyclic, heteroaromatic, or heteroalicyclic, and have zero to 4 non-hydrogen substituents and zero to 3 heteroatoms;
$R^{12}$ is H, carboxyl, $C_2$-$C_6$ acyloxy, $C_2$-$C_6$ alkoxycarbonyl, $C_1$-$C_6$ alkyl, or $C_1$-$C_6$ alkyl substituted with hydroxyl, carboxyl, or halo;
$R^{13}$ and $R^{14}$ are independently selected from H, $C_1$-$C_{12}$ hydrocarbyl, substituted $C_1$-$C_{12}$ hydrocarbyl, heteroatom-containing $C_1$-$C_{12}$ hydrocarbyl, substituted heteroatom-containing $C_1$-$C_{12}$ hydrocarbyl, and functional groups;
$R^{15}$ is methyl, hydroxymethyl, or halomethyl; and
$R^{16}$, in some embodiments, is $C_1$-$C_{18}$ alkyl, $C_2$-$C_{18}$ alkenyl, or $C_2$-$C_{18}$ alkynyl, substituted with (a) —(CO)—$NR^{28}$—$R^{29}$ wherein $R^{28}$ is H or $C_1$-$C_{12}$ hydrocarbyl and $R^{29}$ is $C_1$-$C_{12}$ hydrocarbyl, (b) —$NR^{30}$—$R^{31}$ wherein $R^{30}$ is H or $C_1$-$C_{12}$ hydrocarbyl and $R^{31}$ is $C_6$-$C_{12}$ hydrocarbyl, $C_1$-$C_{12}$ hydrocarbyl substituted with at least one functional group, $C_1$-$C_{12}$ heterohydrocarbyl, or $C_1$-$C_{12}$ heterohydrocarbyl substituted with at least one functional group, (c) —($SO_2$)—$R^{32}$ wherein $R^{32}$ is H or $C_1$-$C_{12}$ heterohydrocarbyl, $C_1$-$C_{12}$ hydrocarbyl substituted with at least one functional group, or $C_1$-$C_{12}$ heterohydrocarbyl substituted with at least one functional group, (d) —($SO_2$)—$NR^{33}R^{34}$ wherein R is H or $C_1$-$C_{12}$ hydrocarbyl and $R^{34}$ is H or $C_1$-$C_{12}$ hydrocarbyl, (e)

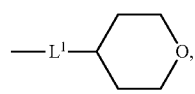

(f)

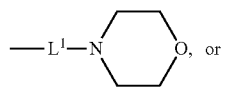

(g)

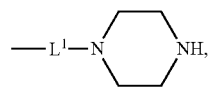

wherein $L^1$ is $C_1$-$C_6$ alkyl, or wherein $R^{16}$ is $C_1$-$C_{12}$ hydrocarbyloxy substituted with an additional $C_1$-$C_{12}$ hydrocarbyloxy.

In an additional embodiment, CBN analogs having the structure of formula (FF) are provided (FF)

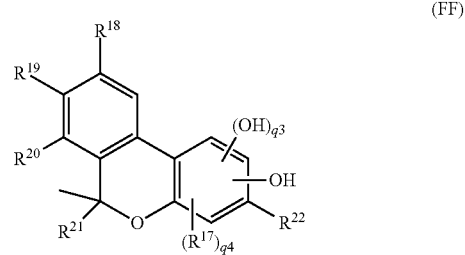

wherein:
q3 is zero or 1, and q4 is zero, 1 or 2;
$R^{17}$ is selected from $C_1$-$C_{12}$ hydrocarbyl, substituted $C_1$-$C_{12}$ hydrocarbyl, heteroatom-containing $C_1$-$C_{12}$ hydrocarbyl, substituted heteroatom-containing $C_1$-$C_{12}$ hydrocarbyl, and functional groups, and wherein when n is 2, the $R^{17}$ may be the same or different and any two $R^{17}$ bound to adjacent carbon atoms may be taken together to form a cyclic structure selected from a five-membered ring and a six-membered ring, optionally fused to an additional five-membered or six-membered ring, wherein the rings are aromatic, alicyclic, heteroaromatic, or heteroalicyclic, and have zero to 4 non-hydrogen substituents and zero to 3 heteroatoms;
$R^{18}$ is H, carboxyl, $C_2$-$C_6$ acyloxy, $C_2$-$C_6$ alkoxycarbonyl, $C_1$-$C_6$ alkyl, or $C_1$-$C_6$ alkyl substituted with hydroxyl, carboxyl, or halo;
$R^{19}$ and $R^{20}$ are independently selected from H, $C_1$-$C_{12}$ hydrocarbyl, substituted $C_1$-$C_{12}$ hydrocarbyl, heteroatom-containing $C_1$-$C_{12}$ hydrocarbyl, substituted heteroatom-containing $C_1$-$C_{12}$ hydrocarbyl, and functional groups;
$R^{21}$ is methyl, hydroxymethyl, or halomethyl; and
$R^{22}$ is $C_1$-$C_{18}$ alkyl, $C_2$-$C_{18}$ alkenyl, or $C_2$-$C_{18}$ alkynyl, substituted with (a) —(CO)—$NR^{35}$—$R^{36}$ wherein $R^{35}$ is H or $C_1$-$C_{12}$ hydrocarbyl and $R^{36}$ is $C_1$-$C_{12}$ hydrocarbyl, (b) —$NR^{37}$—$R^{38}$ wherein $R^{37}$ is H or $C_1$-$C_{12}$ hydrocarbyl and $R^{38}$ is $C_6$-$C_{12}$ hydrocarbyl, $C_1$-$C_{12}$ hydrocarbyl substituted with at least one functional group, $C_1$-$C_{12}$ heterohydrocarbyl, or $C_1$-$C_{12}$ heterohydrocarbyl substituted with at least one functional group, (c) —($SO_2$)—$R^{39}$ wherein $R^{39}$ is H or $C_1$-$C_{12}$ heterohydrocarbyl, $C_1$-$C_{12}$ hydrocarbyl substituted with at least one functional group, or $C_1$-$C_{12}$ heterohydrocarbyl substituted with at least one functional group, (d) —($SO_2$)—$NR^{40}R^{41}$ wherein $R^{42}$ is H or $C_1$-$C_{12}$ hydrocarbyl and $R^{43}$ is H or $C_1$-$C_{12}$ hydrocarbyl, (e)

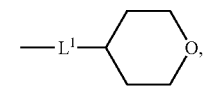

(f)

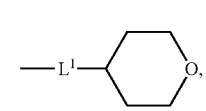

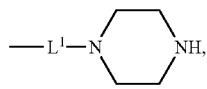

(g)

wherein $L^1$ is $C^1$-$C^6$ alkyl, or wherein $R^{22}$ is $C_1$-$C_{12}$ hydrocarbyloxy substituted with an additional $C_1$-$C_{12}$ hydrocarbyloxy.

In a further embodiment, CBC analogs are provided having the structure (GG)

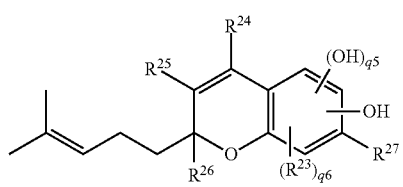

(GG)

wherein:
q5 is zero or 1, q6 is zero1, or 2, and the sum of q5 and q6 does not exceed 2;
$R^{23}$ is selected from $C_1$-$C_{12}$ hydrocarbyl, substituted $C_1$-$C_{12}$ hydrocarbyl, heteroatom-containing $C_1$-$C_{12}$ hydrocarbyl, substituted heteroatom-containing $C_1$-$C_{12}$ hydrocarbyl, and functional groups, and wherein when n is 2, the $R^{23}$ may be the same or different and any two $R^{23}$ bound to adjacent carbon atoms may be taken together to form a cyclic structure selected from a five-membered ring and a six-membered ring, optionally fused to an additional five-membered or six-membered ring, wherein the rings are aromatic, alicyclic, heteroaromatic, or heteroalicyclic, and have zero to 4 non-hydrogen substituents and zero to 3 heteroatoms;
$R^{24}$ is H, $C_1$-$C_6$ alkyl, or $C_1$-$C_6$ alkyl substituted with hydroxyl, carboxyl, or halo;
$R^{25}$ is H, $C_1$-$C_{12}$ hydrocarbyl, substituted $C_1$-$C_{12}$ hydrocarbyl, heteroatom-containing $C_1$-$C_{12}$ hydrocarbyl, substituted heteroatom-containing $C_1$-$C_{12}$ hydrocarbyl, or a functional group;
$R^{26}$ is methyl, hydroxymethyl, or halomethyl; and
$R^{27}$ is $C_1$-$C_{18}$ alkyl or $C_2$-$C_{18}$ alkenyl substituted with (a) —(CO)—$NR^{42}R^{43}$ wherein R is H or $C_1$-$C_{12}$ hydrocarbyl and $R^{43}$ is $C_1$-$C_{12}$ hydrocarbyl, (b) —$NR^{44}R^{45}$ wherein $R^{39}$ is H or $C_1$-$C_{12}$ hydrocarbyl and $R^{45}$ is $C_6$-$C_{12}$ hydrocarbyl, $C_1$-$C_{12}$ hydrocarbyl substituted with at least one functional group, $C_1$-$C_{12}$ heterohydrocarbyl, or $C_1$-$C_{12}$ heterohydrocarbyl substituted with at least one functional group, (c) —(SO$_2$)—$R^{46}$ wherein $R^{46}$ is H or $C_1$-$C_{12}$ heterohydrocarbyl, $C_1$-$C_{12}$ hydrocarbyl substituted with at least one functional group, or $C_1$-$C_{12}$ heterohydrocarbyl substituted with at least one functional group, (d), —(SO$_2$)—$NR^{47}R^{48}$ wherein $R^{47}$ is H or $C_1$-$C_{12}$ hydrocarbyl and $R^{48}$ is H or $C_1$-$C_{12}$ hydrocarbyl,

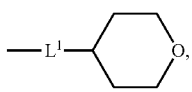

(e)

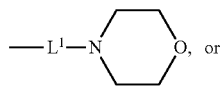

(f)

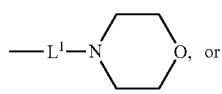

(g)

wherein $L^1$ is $C^1$-$C^6$ alkyl, or wherein $R^{27}$ is $C_1$-$C_{12}$ hydrocarbyloxy substituted with an additional $C_1$-$C_{12}$ hydrocarbyloxy.

In a further embodiment, THCV analogs are provided having the structure (HH)

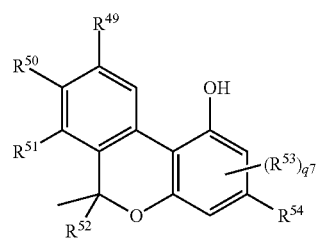

(HH)

wherein:
q7 is zero or 1;
$R^{53}$ is selected from $C_1$-$C_{12}$ hydrocarbyl, substituted $C_1$-$C_{12}$ hydrocarbyl, heteroatom-containing $C_1$-$C_{12}$ hydrocarbyl, substituted heteroatom-containing $C_1$-$C_{12}$ hydrocarbyl, and functional groups;
$R^{39}$ is H, carboxyl, $C_2$-$C_6$ acyloxy, $C_2$-$C_6$ alkoxycarbonyl, $C_1$-$C_6$ alkyl, or $C_1$-$C_6$ alkyl substituted with hydroxyl, carboxyl, or halo;
$R^{50}$ and $R^{51}$ are independently selected from H, $C_1$-$C_{12}$ hydrocarbyl, substituted $C_1$-$C_{12}$ hydrocarbyl, heteroatom-containing $C_1$-$C_{12}$ hydrocarbyl, substituted heteroatom-containing $C_1$-$C_{12}$ hydrocarbyl, and functional groups;
$R^{52}$ is methyl, hydroxymethyl, or halomethyl; and
R is $C_1$-$C_{18}$ alkyl, $C_2$-$C_{18}$ alkenyl, or $C_2$-$C_{18}$ alkynyl, substituted with (a) —(CO)—$NR^{55}R^{56}$ wherein $R^{55}$ is H or $C_1$-$C_{12}$ hydrocarbyl and $R^{56}$ is $C_1$-$C_{12}$ hydrocarbyl, (b) —$NR^{57}R^{58}$ wherein $R^{57}$ is H or $C_1$-$C_{12}$ hydrocarbyl and $R^{58}$ is $C_6$-$C_{12}$ hydrocarbyl, $C_1$-$C_{12}$ hydrocarbyl substituted with at least one functional group, $C_1$-$C_{12}$ heterohydrocarbyl, or $C_1$-$C_{12}$ heterohydrocarbyl substituted with at least one functional group, (c) —(SO$_2$)—$R^{59}$ wherein $R^{59}$ is H or $C_1$-$C_{12}$ heterohydrocarbyl, $C_1$-$C_{12}$ hydrocarbyl substituted with at least one functional group, or $C_1$-$C_{12}$ heterohydrocarbyl substituted with at least one functional group, (d) —(SO$_2$)—$NR^{60}R^{61}$ wherein $R^{60}$ is H or $C_1$-$C_{12}$ hydrocarbyl and $R^{61}$ is H or $C_1$-$C_{12}$ hydrocarbyl,

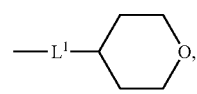

(e)

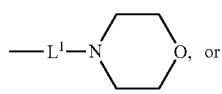

(f)

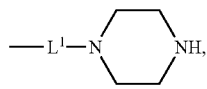
(g)

wherein $L^1$ is $C_1$-$C_6$ alkyl, or wherein $R^{16}$ is $C_1$-$C_{12}$ hydrocarbyloxy substituted with $C_1$-$C_{12}$ hydrocarbyloxy.

Also provided are pharmaceutical formulations comprising a cannabinoid synthesized using a method of the invention in combination with a pharmaceutical excipient appropriate to the selected mode of administration, where the cannabinoid is present in an effective amount for the intended purpose. The formulations may comprise an amount of an additional active agent, such that the amount of the cannabinoid and the additional active agent together represent an effective beneficial amount. Any additional active agent will typically, although not necessarily, be used for the same purpose as the selected cannabinoid analog, and any additional active agent in the formulation may or may not be an additional cannabinoid. Formulations are typically provided as unit dosage forms for administration of the active agent(s) to a subject.

In another embodiment, a method is provided for administering a cannabinoid synthesized using a method of the invention to a subject to achieve a beneficial effect, e.g., to treat a subject affected by a condition, disorder, or disease responsive to administration of a cannabinoid. The method comprises administering to the subject an effective amount of the cannabinoid to achieve the intended effect. Administration may be carried out once, on an as needed basis, or within the context of an ongoing dosage regimen. Indications for which the cannabinoids of the invention have utility are described in detail in the next section.

DETAILED DESCRIPTION OF THE INVENTION

I. Definitions and Nomenclature

A. General

Unless defined otherwise, all technical and scientific terms used herein have the meaning commonly understood by one of ordinary skill in the art to which the invention pertains. Specific terminology of particular importance to the description of the present invention is defined below.

In this specification and the appended claims, the singular forms "a," "an" and "the" include plural referents unless the context clearly dictates otherwise. Thus, for example, reference to "a catalyst" refers not only to a single catalyst but also to a combination of two or more different catalysts, "a reagent" refers to a single reagent or to a combination of reagents, and the like.

B. Chemical Terminology

As used herein, the phrase "having the formula" or "having the structure" is not intended to be limiting and is used in the same way that the term "comprising" is commonly used.

The term "hydrocarbyl" refers to hydrocarbyl groups or linkages containing 1 to about 18 carbon atoms, typically 1 to 12 carbon atoms, including linear, branched, cyclic, saturated, and unsaturated species, such as alkyl groups, alkenyl groups, aryl groups, and the like. "Substituted hydrocarbyl" refers to hydrocarbyl substituted with one or more substituent groups, and the term "heteroatom-containing hydrocarbyl" refers to hydrocarbyl in which at least one carbon atom is replaced with a heteroatom. Unless otherwise indicated, the term "hydrocarbyl" is to be interpreted as including substituted and/or heteroatom-containing hydrocarbyl moieties.

The term "alkyl" as used herein refers to a branched or unbranched saturated hydrocarbon group typically although not necessarily containing 1 to about 18 carbon atoms, such as methyl, ethyl, n-propyl, isopropyl, n-butyl, isobutyl, t-butyl, octyl, decyl, and the like, as well as cycloalkyl groups such as cyclopentyl, cyclohexyl, and the like. Generally, although again not necessarily, alkyl groups herein contain 1 to 12 carbon atoms, e.g., 1 to 12 carbon atoms, 1 to 10 carbon atoms, 1 to 8 carbon atoms, 1 to 6 carbon atoms or 1 to 3 carbon atoms. "Substituted alkyl" refers to alkyl substituted with one or more substituent groups, and the terms "heteroatom-containing alkyl" and "heteroalkyl" refer to alkyl in which at least one carbon atom is replaced with a heteroatom, as described in further detail infra. If not otherwise indicated, the term "alkyl" includes linear, branched, cyclic, unsubstituted, substituted, and/or heteroatom-containing alkyl.

The term "alkenyl" as used herein refers to a linear, branched, or cyclic hydrocarbon group of 2 to about 18 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, and the like. Alkenyl groups herein typically contain 2 to 12 carbon atoms, e.g., 2 to 12 carbon atoms, 2 to 10 carbon atoms, 2 to 8 carbon atoms, 2 to 6 carbon atoms or 2 to 3 carbon atoms. The term "cycloalkenyl" intends a cyclic alkenyl group, typically having 5 to 8 carbon atoms. The term "substituted alkenyl" refers to alkenyl substituted with one or more substituent groups, and the terms "heteroatom-containing alkenyl" and "heteroalkenyl" refer to alkenyl in which at least one carbon atom is replaced with a heteroatom. If not otherwise indicated, the term "alkenyl" includes linear, branched, cyclic, unsubstituted, substituted, and/or heteroatom-containing alkenyl.

The term "alkynyl" as used herein refers to a linear or branched hydrocarbon group of 2 to 18 carbon atoms containing at least one triple bond, such as ethynyl, n-propynyl, and the like. Generally, although again not necessarily, alkynyl groups herein contain 2 to 12 carbon atoms, e.g., 2 to 12 carbon atoms, 2 to 10 carbon atoms, 2 to 8 carbon atoms, 2 to 6 carbon atoms or 2 to 3 carbon atoms. The term "substituted alkynyl" refers to alkynyl substituted with one or more substituent groups, and the terms "heteroatom-containing alkynyl" and "heteroalkynyl" refer to alkynyl in which at least one carbon atom is replaced with a heteroatom. If not otherwise indicated, the term "alkynyl" includes linear, branched, unsubstituted, substituted, and/or heteroatom-containing alkynyl.

The term "alkoxy" as used herein refers to an alkyl group bound through a single, terminal ether linkage; that is, an "alkoxy" group may be represented as —O-alkyl where alkyl is as defined above. Alkoxy groups thus include $C_1$-$C_6$ alkoxy groups such as methoxy, ethoxy, n-propoxy, isopropoxy, t-butyloxy, etc. The terms "alkenyloxy" and "alkynyloxy" are defined in an analogous manner.

The term "aryl" as used herein, and unless otherwise specified, refers to an aromatic substituent containing a single aromatic ring or multiple aromatic rings that are fused together, directly linked, or indirectly linked (such that the different aromatic rings are bound to a common group such as a methylene or ethylene moiety). Preferred aryl groups contain 5 to 18 carbon atoms, and particularly preferred aryl groups contain 5 to 14 carbon atoms. Exemplary aryl groups contain one aromatic ring or two fused or linked aromatic rings, e.g., phenyl, naphthyl, biphenyl, diphenylether, diphenylamine, benzophenone, and the like. "Substituted aryl" refers to an aryl moiety substituted with one or more substituent groups, and the terms "heteroatom-containing aryl" and "heteroaryl" refer to aryl substituent, in which at least one carbon atom is replaced with a heteroatom, as will be described in further detail infra. If not otherwise indicated, the term "aryl" includes unsubstituted, substituted, and/or heteroatom-containing aromatic substituents.

The term "aryloxy" as used herein refers to an aryl group bound through a single, terminal ether linkage, wherein "aryl" is as defined above. An "aryloxy" group may be represented as —O-aryl where aryl is as defined above. Preferred aryloxy groups contain 5 to 18 carbon atoms, and particularly preferred aryloxy groups contain 5 to 14 carbon atoms. Examples of aryloxy groups include, without limitation, phenoxy, o-halo-phenoxy, m-halo-phenoxy, p-halo-phenoxy, o-methoxy-phenoxy, m-methoxy-phenoxy, p-methoxy-phenoxy, 2,4-dimethoxy-phenoxy, 3,4,5-trimethoxy-phenoxy, and the like.

The term "alkaryl" refers to an aryl substituent that is substituted with an alkyl group, and the term "aralkyl" refers to an alkyl substituent that is substituted with an aryl group, wherein "aryl" and "alkyl" are as defined above. Preferred alkaryl and aralkyl groups contain 6 to 18 carbon atoms, and particularly preferred aralkyl groups contain 6 to 16 carbon atoms. For example, alkaryl groups include, for example, p-methylphenyl, 2,4-dimethylphenyl, p-cyclohexylphenyl, 2,7-dimethylnaphthyl, 7-cyclooctyinaphthyl, 3-ethyl-cyclopenta-1,4-diene, and the like. Aralkyl groups include, without limitation, benzyl, 2-phenyl-ethyl, 3-phenyl-propyl, 4-phenyl-butyl, 5-phenyl-pentyl, 4-phenylcyclohexyl, 4-benzylcyclohexyl, 4-phenylcyclohexylmethyl, 4-benzylcyclohexylmethyl, and the like. The terms "alkaryloxy" and "aralkyloxy" refer to substituents of the formula —OR wherein R is alkaryl or aralkyl, respectively, as just defined.

The term "acyl" refers to substituents having the formula —(CO)-alkyl, —(CO)-aryl, or —(CO)-aralkyl, and the term "acyloxy" refers to substituents having the formula —O(CO)-alkyl, —O(CO)-aryl, or —O(CO)-aralkyl, wherein "alkyl," "aryl, and "aralkyl" are as defined above.

The term "cyclic" refers to alicyclic or aromatic substituents that may or may not be substituted and/or heteroatom containing, and that may be monocyclic, bicyclic, or polycyclic.

The term "alicyclic" is used in the conventional sense to refer to an aliphatic cyclic moiety, as opposed to an aromatic cyclic moiety, and may be monocyclic, bicyclic, polycyclic, and may be bridged.

The terms "halo" and "halogen" are used in the conventional sense to refer to a chloro, bromo, fluoro, or iodo substituent.

The term "heteroatom-containing" as in a "heteroatom-containing alkyl group" (also termed a "heteroalkyl" group) or a "heteroatom-containing aryl group" (also termed a "heteroaryl" group) refers to a molecule, linkage, or substituent in which one or more carbon atoms are replaced with an atom other than carbon, e.g., nitrogen, oxygen, sulfur, phosphorus, or silicon, typically nitrogen, oxygen, or sulfur, preferably nitrogen or oxygen. Similarly, the term "heteroalkyl" refers to an alkyl substituent that is heteroatom-containing, the term "heterocyclic" refers to a cyclic substituent that is heteroatom-containing, the terms "heteroaryl" and "heteroaromatic" respectively refer to "aryl" and "aromatic" substituents that are heteroatom-containing, and the like. Examples of heteroalkyl groups include alkoxyaryl, alkylsulfanyl-substituted alkyl, N-alkylated amino alkyl, and the like. Examples of heteroaryl substituents include pyrrolyl, pyrrolidinyl, pyridinyl, quinolinyl, indolyl, pyrimidinyl, imidazolyl, 1,2,4-triazolyl, tetrazolyl, etc., and examples of heteroatom-containing alicyclic groups are pyrrolidino, morpholino, piperazino, piperidino, etc.

By "substituted" as in "substituted alkyl," "substituted aryl," and the like, as alluded to in some of the aforementioned definitions, is meant that in the alkyl, aryl, or other moiety, at least one hydrogen atom bound to a carbon (or other) atom is replaced with one or more non-hydrogen substituents. Examples of such substituents include functional groups and hydrocarbyl moieties.

Functional groups that may represent substituents in the substituted molecular structures and segments thereof include, without limitation: halo, hydroxyl, sulfhydryl, $C_1$-$C_{18}$ alkoxy, $C_2$-$C_{18}$ alkoxyalkyl, $C_2$-$C_{18}$ alkenyloxy, $C_2$-$C_{18}$ alkynyloxy, $C_6$-$C_{18}$ aryloxy, acyl (including $C_2$-$C_{18}$ alkylcarbonyl (—CO-alkyl) and $C_6$-$C_{18}$ arylcarbonyl (—CO-aryl)), acyloxy (—O-acyl), $C_2$-$C_{18}$ alkoxycarbonyl (—(CO)—O-alkyl), $C_6$-$C_{18}$ aryloxycarbonyl (—(CO)—O-aryl), halocarbonyl (—(CO)—X where X is halo), $C_2$-$C_{18}$ alkylcarbonato (—O—(CO)—O-alkyl), $C_6$-$C_{18}$ arylcarbonato (—O—(CO)—O-aryl), carboxy (—COOH), carboxylato (—COO—), carbamoyl (—(CO)—$NH_2$), mono-($C_1$-$C_{18}$ alkyl)-substituted carbamoyl (—(CO)—NH($C_1$-$C_{18}$ alkyl)), di-($C_1$-$C_{18}$ alkyl)-substituted carbamoyl (—(CO)—N($C_1$-$C_{18}$ alkyl)$_2$), mono-($C_5$-$C_{18}$ aryl)-substituted carbamoyl (—(CO)—NH-aryl), di-($C_5$-$C_{18}$ aryl)-substituted carbamoyl (—(CO)—N(aryl)$_2$), di-N—($C_1$-$C_{18}$ alkyl), N—($C_5$-$C_{18}$ aryl)-substituted carbamoyl, thiocarbamoyl (—(CS)—$NH_2$), carbamido (—NH—(CO)—$NH_2$), cyano (—C≡N), isocyano (—$N^{30}$≡$C^-$—), cyanato (—O—C≡N), isocyanato (—O—$N^{30}$≡$C^-$—), isothiocyanato (—S—C≡N), azido (—N=$N^+$=$N^-$), formyl (—(CO)—H), thioformyl (—(CS)—H), amino (—$NH_2$), mono-($C_1$-$C_{18}$ alkyl)-substituted amino, di-($C_1$-$C_{18}$ alkyl)-substituted amino, mono-($C_5$-$C_{18}$ aryl)-substituted amino, di-($C_5$-$C_{18}$ aryl)-substituted amino, $C_2$-$C_{18}$ alkylamido (—NH—(CO)-alkyl), $C_6$-$C_{18}$ arylamido (—NH—(CO)-aryl), imino (—CR=NH where R=hydrogen, $C_1$-$C_{18}$ alkyl, $C_5$-$C_{18}$ aryl, $C_6$-$C_{18}$ alkaryl, $C_6$-$C_{18}$ aralkyl, etc.), alkylimino (—CR=N(alkyl), where R=hydrogen, $C_1$-$C_{18}$ alkyl, $C_5$-$C_{18}$ aryl, $C_6$-$C_{18}$ alkaryl, $C_6$-$C_{18}$ aralkyl, etc.), arylimino (—CR=N(aryl), where R=hydrogen, $C_1$-$C_{18}$ alkyl, $C_5$-$C_{18}$ aryl, $C_6$-$C_{18}$ alkaryl, $C_6$-$C_{18}$ aralkyl, etc.), nitro (—$NO_2$), nitroso (—NO), sulfo (—$SO_2$—OH), sulfonato (—$SO_2$—O—), $C_1$-$C_{18}$ alkylsulfanyl (—S-alkyl; also termed "alkylthio"), arylsulfanyl (—S-aryl; also termed "arylthio"), $C_1$-$C_{18}$ alkylsulfinyl (—(SO)-alkyl), $C_5$-$C_{18}$ arylsulfinyl (—(SO)-aryl), $C_1$-$C_{18}$ alkylsulfonyl (—$SO_2$-alkyl), $C_5$-$C_{18}$ arylsulfonyl (—$SO_2$-aryl), phosphono (—P(O)(OH)$_2$), phosphonato (—P(O)(O—)$_2$), phosphinato (—P(O)(O—)), phospho (—$PO_2$), and phosphino (—$PH_2$). Typically, hydrocarbyl moieties in the aforementioned functional groups, if acyclic, have 1 to 12 carbon atoms, while if cyclic, have 5 to 16 carbon atoms.

The aforementioned functional groups may, if a particular group permits, be further substituted with one or more additional functional groups or with one or more hydrocarbyl moieties such as those specifically enumerated above, and the term "functional group" encompasses all such instances.

When the term "substituted" appears prior to a list of possible substituted groups, it is intended that the term apply to every member of that group. For example, the phrase "substituted alkyl, alkenyl, and aryl" is to be interpreted as "substituted alkyl, substituted alkenyl, and substituted aryl." Analogously, when the term "heteroatom-containing" appears prior to a list of possible heteroatom-containing groups, it is intended that the term apply to every member of that group. For example, the phrase "heteroatom-containing alkyl, alkenyl, and aryl" is to be interpreted as "heteroatom-containing alkyl, substituted alkenyl, and substituted aryl."

Some of the compounds described herein may contain one or more asymmetric centers and give rise to enantiomers, diastereomers, or other stereoisomeric forms. Such a compound may be in the form of a single stereoisomer, i.e., be "stereoisomerically pure," or contained in a mixture of two or more stereoisomers, e.g., two diastereomers, two enantiomers, or a mixture of two diastereomers and two enantiomers. However, cannabidiol and analogs thereof, as referred to herein and unless otherwise specified, are in (−)-configuration rather than in the (+)-configuration or in a (±) racemic mixture (numbering convention included):

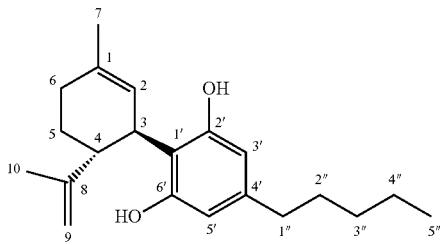

See Lago Fernandez et al. (2017), "New Methods for the Synthesis of Cannabidiol Derivatives," *Methods Enzymol.* 593: 237-257. For clarity in describing various types of analogs described herein, the phenyl group with carbon atoms 1' through 6' is sometimes referred to herein as the "phloroglucinol ring" while the cyclohexene ring with carbon atoms 1 through 6 is sometimes referred to herein as the "menthadienol ring." The numbering convention above is also used herein for other cannabinoids, including cannabinol, cannabichromene, and tetrahydrocannabivarin.

C. Pharmaceutical Terminology

A "pharmacologically active agent," sometimes referred to herein as simply an "active agent," encompasses not only the specified cannabinoid or other molecular entity but also its pharmaceutically acceptable analogs and derivatives, including, but not limited to, salts, esters, prodrugs, conjugates, active metabolites, crystalline forms, enantiomers, stereoisomers, and other such derivatives, analogs, and related compounds.

By "pharmaceutically acceptable" is meant a material that is not biologically or otherwise undesirable, i.e., the material may be incorporated into a pharmaceutical formulation or dosage form administered to a subject without causing any undesirable biological effects or interacting in a deleterious manner with any of the other components of the composition in which it is contained. When the term "pharmaceutically acceptable" is used to refer to a pharmaceutical carrier or excipient, it is implied that the carrier or excipient has met the required standards of toxicological and manufacturing testing and/or that it is included on the Inactive Ingredient Guide prepared by the U.S. Food and Drug administration.

The terms "treating" and "treatment" as used herein refer to reduction in severity and/or frequency of symptoms, elimination of symptoms and/or underlying cause, and improvement or remediation of damage, e.g., reduction in the number and/or extent of menopausal symptoms with a patient being given hormone replacement therapy using the drug delivery system of the invention. Unless otherwise indicated, the terms "treating" and "treatment" as used herein encompass prevention of symptoms as well.

The term "effective amount" of a cannabinoid or pharmaceutical formulation containing the cannabinoid refers to an amount that is nontoxic and sufficient for producing an intended beneficial effect. The beneficial effect is typically, although not necessarily, a therapeutic effect, wherein administration involves "treatment" as defined above. An "effective dosage" and a "unit dosage" provide an "effective amount" of an active agent.

As used herein, "subject" or "individual" or "patient" refers to any living individual for whom therapy is desired, and refers to the recipient of the therapy to be practiced according to the invention. The subject is generally a mammalian individual and most typically is human.

"Optional" or "optionally" means that the subsequently described circumstance may or may not occur, so that the description includes instances where the circumstance occurs and instances where it does not. For example, the phrase "optionally co-administered with" when referring to the administration of an active agent to a subject, encompasses administration of the active agent in the context of a monotherapy as well as co-administration of the active agent with a second compound. In another context, the phrase "optionally substituted" means that a non-hydrogen substituent may or may not be present on a given atom, and, thus, the description includes structures wherein a non-hydrogen substituent is present and structures wherein a non-hydrogen substituent is not present.

II. Synthesis of Olivetol and Analogs Thereof

In a first embodiment, the invention provides a method for synthesizing a compound useful as a synthetic precursor to the cannabinoids described herein, including, without limitation CBD and CBD analogs. In this embodiment, the compound synthesized is olivetol or an olivetol analog that has the structure of formula (AA)

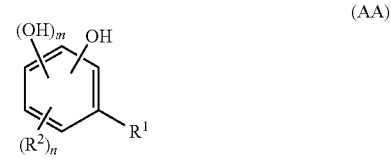

wherein:
  m is zero or 1;
  n is zero, 1, or 2;
  $R^1$ is selected from $C_1$-$C_{18}$ hydrocarbyl, substituted $C_1$-$C_{18}$ hydrocarbyl, heteroatom-containing $C_1$-$C_{18}$ hydrocarbyl, and substituted heteroatom-containing $C_1$-$C_{18}$ hydrocarbyl; and
  $R^2$ is selected from $C_1$-$C_{18}$ hydrocarbyl, substituted $C_1$-$C_{18}$ hydrocarbyl, heteroatom-containing $C_1$-$C_{18}$ hydrocarbyl, substituted heteroatom-containing $C_1$-$C_{18}$ hydrocarbyl, and functional groups, and wherein when n is 2, the $R^2$ may be the same or different and any $R^2$ bound to adjacent carbon atoms may be taken together to form a cyclic structure selected from a five-membered ring and a six-membered ring, optionally fused to an additional five-membered or six-membered ring, wherein the rings are aromatic, alicyclic, heteroaromatic, or heteroalicyclic, and have zero to 4 non-hydrogen substituents and zero to 3 heteroatoms.

$R^1$, as noted above, is an optionally substituted, optionally heteroatom-containing $C_1$-$C_{18}$ hydrocarbyl moiety. In one embodiment, $R^1$ is an optionally substituted, optionally heteroatom-containing $C_1$-$C_{12}$ hydrocarbyl moiety, typically an optionally substituted, optionally heteroatom-containing $C_1$-$C_8$ hydrocarbyl moiety. If heteroatoms are present there are generally not more than 4, typically not more than 2, e.g., in the range of 1 to 4, and the heteroatoms are typically selected from O, N, and S. A nitrogen heteroatom may be contained within a primary, secondary, or tertiary amino group or linkage, within a functional group such as an amide or a sulfonamide, or within an aromatic or alicyclic ring, thus including species such as pyrrolyl, pyrrolidinyl, pyridinyl, quinolinyl, indolyl, pyrimidinyl, imidazolyl, 1,2,3-triazolyl, 1,2,4-triazolyl, 1,3,4-triazolyl, tetrazolyl, morpholino, piperazino, and piperidino. An oxygen heteroatom may be contained within a hydroxyl group, an alkoxy group, a carbonyl moiety (e.g., in an ester or amide linkage), an ether linkage, or a furanyl, tetrahydrofuranyl, pyranyl, tetrahydropyranyl, dioxanyl, or morpholino ring, or the like. A sulfur heteroatom may be within a thioether linkage, a sulfonate linkage, a sulfonate group, or the like. When the hydrocarbyl or heteroatom-containing hydrocarbyl moiety $R^1$ is substituted, the nonhydrogen substituents are generally selected from the functional groups set forth under the definition of "substituted" in part (I) of this section. Typical substituents include, without limitation, halo, carboxyl, alkoxy, amido, amino, sulfonamido, alicyclic groups, and aromatic groups. For instance, $R^1$ may be selected from $C_1$-$C_{18}$ alkyl, $C_2$-$C_{18}$ alkenyl, and $C_2$-$C_{18}$ alkynyl, any of which may be substituted with zero to 3 functional groups selected from halo, hydroxyl, carboxyl, $C_1$-$C_8$ alkoxy, $C_2$-$C_8$ acyloxy, $C_2$-$C_8$ alkoxycarbonyl, amino, mono-($C_1$-$C_8$ alkyl)-substituted amino, di-($C_1$-$C_8$ alkyl) substituted amino, $C_2$-$C_8$ alkylamido, mono-($C_1$-$C_8$ alkyl)-substituted carbamoyl, di-($C_1$-$C_8$ alkyl)-substituted carbamoyl, and combinations thereof.

Some examples of $R^1$ include, without limitation:

$C_1$-$C_{18}$ alkyl (e.g., $C_1$-$C_{12}$ alkyl, $C_1$-$C_{10}$ alkyl, or $C_1$-$C_8$ alkyl, such as methyl, ethyl, n-propyl, isopropyl, n-butyl, isobutyl, t-butyl, n-pentyl, cyclohexyl, and the like);

$C_2$-$C_{18}$ alkenyl (e.g., $C_2$-$C_{12}$ alkenyl, $C_2$-$C_{10}$ alkenyl or $C_2$-$C_8$ alkenyl);

$C_2$-$C_{18}$ alkynyl (e.g., $C_2$-$C_{12}$ alkynyl, $C_2$-$C_{10}$ alkynyl or $C_2$-$C_8$ alkynyl);

$C_6$-$C_{18}$ aralkyl (e.g., $C_5$-$C_6$ aryl-substituted $C_1$-$C_{12}$ alkyl or $C_5$-$C_6$ aryl-substituted $C_1$-$C_8$ alkyl);

$C_4$-$C_{16}$ heteroaralkyl (e.g., $C_3$-$C_6$ heteroaryl-substituted $C_1$-$C_{10}$ alkyl or $C_3$-$C_6$ heteroaryl-substituted $C_1$-$C_8$ alkyl), wherein the heteroaryl substituent may be saturated or unsaturated;

$C_1$-$C_{18}$ haloalkyl (e.g., $C_1$-$C_{12}$ chloroalkyl, $C_1$-$C_{10}$ chloroalkyl, $C_1$-$C_8$ chloroalkyl, $C_1$-$C_{12}$ fluoroalkyl, $C_1$-$C_{10}$ fluoroalkyl, or $C_1$-$C_8$ fluoroalkyl);

$C_1$-$C_{18}$ hydroxyalkyl (e.g., $C_1$-$C_{12}$ hydroxyalkyl, $C_1$-$C_{10}$ hydroxyalkyl, or $C_1$-$C_8$ hydroxyalkyl);

$C_2$-$C_{18}$ haloalkenyl (e.g., $C_2$-$C_{12}$ chloroalkenyl, $C_2$-$C_{10}$ chloroalkenyl, $C_2$-$C_8$ chloroalkenyl, $C_2$-$C_{12}$ fluoroalkenyl, $C_2$-$C_{10}$ fluoroalkenyl or $C_2$-$C_6$ fluoroalkenyl);

$C_2$-$C_{18}$ haloalkynyl (e.g., $C_2$-$C_{12}$ chloroalkynyl, $C_2$-$C_{10}$ chloroalkynyl, $C_2$-$C_8$ chloroalkynyl, $C_2$-$C_{12}$ fluoroalkynyl, $C_2$-$C_{10}$ fluoroalkynyl or $C_2$-$C_6$ fluoroalkynyl);

$C_2$-$C_{18}$ alkoxyalkyl (e.g., ($C_1$-$C_8$ alkoxy)-substituted $C_1$-$C_{12}$ alkyl or ($C_1$-$C_8$ alkoxy)-substituted $C_1$-$C_8$ alkyl), unsubstituted or substituted with an additional $C_2$-$C_{18}$ alkoxyalkyl;

$C_2$-$C_{18}$ alkoxyalkenyl (e.g., ($C_1$-$C_8$ alkoxy)-substituted $C_2$-$C_{12}$ alkenyl or ($C_1$-$C_8$ alkoxy)-substituted $C_2$-$C_8$ alkenyl);

$C_2$-$C_{12}$ alkoxyalkynyl (e.g., ($C_1$-$C_8$ alkoxy)-substituted $C_2$-$C_{12}$ alkynyl or ($C_1$-$C_8$ alkoxy)-substituted $C_2$-$C_8$ alkynyl);

$C_2$-$C_{18}$ carboxyalkyl (e.g., $C_2$-$C_{12}$ carboxyalkyl, $C_2$-$C_{10}$ carboxyalkyl, or $C_2$-$C_8$ carboxyalkyl), $C_3$-$C_{18}$ carboxyalkenyl (e.g., $C_3$-$C_{12}$ carboxyalkenyl, $C_3$-$C_{10}$ carboxyalkenyl, or $C_3$-$C_8$ carboxyalkenyl), $C_1$-$C_{18}$ alkyl, e.g., $C_1$-$C_{12}$ alkyl, substituted with mono-($C_1$-$C_8$ alkyl)-substituted carbamoyl (—(CO)—NH($C_1$-$C_8$ alkyl)) or di-($C_1$-$C_8$ alkyl)-substituted carbamoyl (—(CO)—N($C_1$-$C_8$ alkyl)$_2$);

$C_2$-$C_{18}$ alkenyl, e.g., $C_2$-$C_{12}$ alkenyl, substituted with mono-($C_1$-$C_8$ alkyl)-substituted carbamoyl (—(CO)—NH($C_1$-$C_8$ alkyl)) or di-($C_1$-$C_8$ alkyl)-substituted carbamoyl (—(CO)—N($C_1$-$C_{12}$ alkyl)$_2$);

$C_1$-$C_{18}$ alkyl, e.g., $C_1$-$C_{12}$ alkyl, substituted with $C_2$-$C_8$ alkylamido (—NH—(CO)-alkyl);

$C_2$-$C_{18}$ alkenyl, e.g., $C_2$-$C_{12}$ alkenyl, substituted with $C_2$-$C_8$ alkylamido (—NH—(CO)-alkenyl);

$C_1$-$C_{18}$ alkyl, e.g., $C_1$-$C_{12}$ alkyl, substituted with —NH—($C_1$-$C_8$ alkyl) or —N($C_1$-$C_8$ alkyl)$_2$;

$C_2$-$C_{18}$ alkenyl, e.g., $C_2$-$C_{12}$ alkenyl, substituted with —NH—($C_1$-$C_8$ alkyl) or —N($C_1$-$C_8$ alkyl)$_2$;

$C_1$-$C_{18}$ alkyl, e.g., $C_1$-$C_{12}$ alkyl, substituted with $C_1$-$C_8$ alkylsulfonyl (—SO$_2$-alkyl);

$C_2$-$C_{18}$ alkenyl, e.g., $C_2$-$C_{12}$ alkenyl, substituted with $C_1$-$C_8$ alkylsulfonyl (—SO$_2$-alkyl);

$C_1$-$C_{18}$ alkyl, e.g., $C_1$-$C_{12}$ alkyl, substituted with $C_0$-$C_8$ sulfonamido (—SO$_2$—NH$_2$ or —SO$_2$—N alkyl);

$C_2$-$C_{18}$ alkenyl, e.g., $C_2$-$C_{12}$ alkenyl, substituted with $C_0$-$C_8$ sulfonamido (—SO$_2$—NH$_2$ or —SO$_2$—N alkyl);

$C_1$-$C_{18}$ alkyl, e.g., $C_1$-$C_{12}$ alkyl, substituted with oxanyl, morpholino, diazinanyl, generally at the nitrogen atom of a nitrogen heterocycle, as in morpholino and diazinanyl; or $C_2$-$C_{18}$ alkenyl, e.g., $C_2$-$C_{12}$ alkenyl, substituted with oxanyl, morpholino, diazinanyl, generally at the nitrogen atom of a nitrogen heterocycle, as in morpholino and diazinanyl.

Any of the foregoing $R^1$ substituents may be further substituted with one or more additional substituents that may or may not be the same as the substituents identified above. Examples of such $R^1$ substituents include a $C_1$-$C_{18}$ alkyl group (e.g., a $C_1$-$C_{12}$ alkyl group, a $C_1$-$C_{10}$ alkyl, or $C_1$-$C_8$ alkyl group) disubstituted with Cl or F; a $C_2$-$C_{18}$ alkoxyalkyl group substituted with one or more $C_2$-$C_{18}$ alkoxyalkyl groups, e.g., a $C_2$-$C_{12}$ alkoxyalkyl group having the structure ($C_1$-$C_6$ alkoxy)-substituted $C_1$-$C_{12}$ alkyl, wherein the $C_1$-$C_{12}$ alkyl is substituted with an additional $C_2$-$C_{12}$ alkoxyalkyl group, and the like.

Specific examples of $R^1$ substituents (sometimes referred to hereafter as the "representative $R^1$ substituents") are as follows:

For example, the $R^1$ substituent may be —(CH$_2$)—(CO)—NH—CH$_3$, —(CH$_2$)—(CO)—NH—CH$_2$CH$_3$, —(CH$_2$)—(CO)—NH—(CH$_2$)$_2$CH$_3$, —(CH$_2$)—(CO)—NH—(CH$_2$)$_3$CH$_3$, —(CH$_2$)—(CO)—NH—(CH$_2$)$_4$CH$_3$, —(CH$_2$)$_2$—(CO)—NH—CH$_3$, —(CH$_2$)$_2$—(CO)—NH—CH$_2$CH$_3$, —(CH$_2$)$_2$—(CO)—NH—(CH$_2$)$_2$CH$_3$, —(CH$_2$)$_2$—(CO)—NH—(CH$_2$)$_3$CH$_3$, —(CH$_2$)$_2$—(CO)—NH—(CH$_2$)$_4$CH$_3$, —(CH$_2$)$_3$—(CO)—NHCH$_3$, —(CH$_2$)$_3$—(CO)—NHCH$_2$CH$_3$, —(CH$_2$)$_3$—(CO)—NH—(CH$_2$)$_2$CH$_3$, —(CH$_2$)$_3$—(CO)—NH—(CH$_2$)$_3$CH$_3$, —(CH$_2$)$_3$—(CO)—NH—(CH$_2$)$_3$CH$_3$, —(CH$_2$)—NH—CH$_3$, —(CH$_2$)—NH—CH$_2$CH$_3$, —(CH$_2$)—NH—(CH$_2$)$_2$CH$_3$, —(CH$_2$)—NH—(CH$_2$)$_3$CH$_3$, —(CH$_2$)$_2$—NH—CH$_3$, —(CH$_2$)$_2$—NH—CH$_2$CH$_3$, —(CH$_2$)$_2$—NH—(CH$_2$)$_2$CH$_3$, —(CH$_2$)$_2$—NH—(CH$_2$)$_3$CH$_3$, —(CH$_2$)$_3$—NH—CH$_3$, —(CH$_2$)$_3$—NH—CH$_2$CH$_3$, —(CH$_2$)$_3$—NH—(CH$_2$)$_2$CH$_3$, —(CH$_2$)$_3$—NH—(CH$_2$)$_3$CH$_3$, —(CH$_2$)$_3$—NH—(CH$_2$)$_4$CH$_3$, —(CH$_2$)—(SO$_2$)—CH$_3$, —(CH$_2$)—(SO$_2$)—CH$_2$CH$_3$, —(CH$_2$)—(SO$_2$)—(CH$_2$)$_3$CH$_3$, —(CH$_2$)—(SO$_2$)—(CH$_2$)$_4$CH$_3$, —(CH$_2$)$_2$—(SO$_2$)—CH$_3$, —(CH$_2$)$_2$—(SO$_2$)—CH$_2$CH$_3$, —(CH$_2$)$_2$—(SO$_2$)—(CH$_2$)$_2$CH$_3$, —(CH$_2$)$_2$—(SO$_2$)—(CH$_2$)$_4$CH$_3$, —(CH$_2$)$_3$—(SO$_2$)—CH$_3$, —(CH$_2$)$_3$—(SO$_2$)—CH$_2$CH$_3$, —(CH$_2$)$_3$—(SO$_2$)—(CH$_2$)$_3$CH$_3$, —(CH$_2$)$_3$—(SO$_2$)—(CH$_2$)$_4$CH$_3$, —(CH$_2$)—(SO$_2$)—NH—CH$_3$, —(CH$_2$)—(SO$_2$)—NH—CH$_2$CH$_3$, —(CH$_2$)—(SO$_2$)—NH—(CH$_2$)$_2$CH$_3$, —(CH$_2$)—(SO$_2$)—NH—(CH$_2$)$_4$CH$_3$, —(CH$_2$)$_2$—(SO$_2$)—NH—CH$_3$, —(CH$_2$)$_2$—(SO$_2$)—NH—CH$_2$CH$_3$, —(CH$_2$)$_2$—(SO$_2$)—NH—(CH$_2$)$_2$CH$_3$, —(CH$_2$)$_2$—(SO$_2$)—NH—(CH$_2$)$_4$CH$_3$, —(CH$_2$)$_3$—(SO$_2$)—NH—CH$_3$, —(CH$_2$)$_3$—(SO$_2$)—NH—CH$_2$CH$_3$, —(CH$_2$)$_3$—(SO$_2$)—NH—(CH$_2$)$_2$CH$_3$, —(CH$_2$)$_3$—(SO$_2$)—NH—(CH$_2$)$_4$CH$_3$, —(SO)$_2$—NH—CH$_3$, —CH$_2$—O—CH$_3$, —CH$_2$—O—CH$_2$CH$_3$, —CH$_2$—O—(CH$_2$)$_2$CH$_3$, —CH$_2$—O—(CH$_2$)$_3$CH$_3$, —CH$_2$—O—(CH$_2$)$_4$CH$_3$, —(CH$_2$)$_2$—O—CH$_3$, —(CH$_2$)$_2$—O—CH$_2$CH$_3$, —(CH$_2$)$_2$—O—(CH$_2$)$_2$CH$_3$, —(CH$_2$)$_2$—O—(CH$_2$)$_3$CH$_3$, —(CH$_2$)$_2$—O—(CH$_2$)$_4$CH$_3$, —(CH$_2$)$_3$—O—CH$_3$, —(CH$_2$)$_3$—O—CH$_2$CH$_3$, —(CH$_2$)$_3$—O—(CH$_2$)$_2$CH$_3$, —(CH$_2$)$_3$—O—(CH$_2$)$_3$CH$_3$, —(CH$_2$)$_3$—O—(CH$_2$)$_4$CH$_3$, —O—CH$_3$, —O—CH$_2$CH$_3$, —O—(CH$_2$)$_2$CH$_3$, —O—(CH$_2$)$_3$CH$_3$, —O—(CH$_2$)$_4$CH$_3$, —O—CH$_2$—O—CH$_3$, —O—(CH$_2$)$_2$—OCH$_3$, —O—(CH$_2$)$_3$—OCH$_3$, —O—(CH$_2$)$_4$—OCH$_3$, —O—CH$_2$—O—CH$_2$CH$_3$, —O—(CH$_2$)$_2$—CH$_2$CH$_3$, —O—(CH$_2$)$_3$—OCH$_2$CH$_3$, —O—CH$_2$—O—(CH$_2$)$_2$CH$_3$, —O—(CH$_2$)$_2$—O—(CH$_2$)$_2$CH$_3$, —O—(CH$_2$)$_3$—O(CH$_2$)$_2$CH$_3$, —O—(CH$_2$)$_3$—O—(CH$_2$)$_2$CH$_3$, —O—CH$_2$—O—(CH$_2$)$_2$CH$_3$, —O—(CH$_2$)$_2$—O—(CH$_2$)$_2$CH$_3$, —O—(CH$_2$)$_3$—O(CH$_2$)$_2$CH$_3$, —O—(CH$_2$)$_3$—O(CH$_2$)$_2$CH$_3$, —CH$_2$—O—CH$_2$—O—CH$_3$, —CH$_2$—O—(CH$_2$)$_2$—OCH$_3$, —CH$_2$—O—(CH$_2$)$_3$—OCH$_3$, —CH$_2$—O—(CH$_2$)$_3$—OCH$_3$, —O—CH$_2$—NH—CH$_3$, —O—(CH$_2$)$_2$—NH—CH$_3$, —O—(CH$_2$)$_3$—NH—CH$_3$, —O—(CH$_2$)$_4$—NH—CH$_3$, —(CO)—NH—CH$_3$, —(CO)—NH—CH$_2$CH$_3$, —(CO)—NH—(CH$_2$)$_2$CH$_3$, —(CO)—NH—(CH$_2$)$_3$CH$_3$, or any of the following:

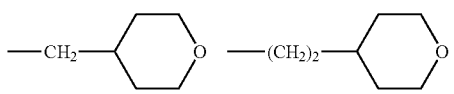

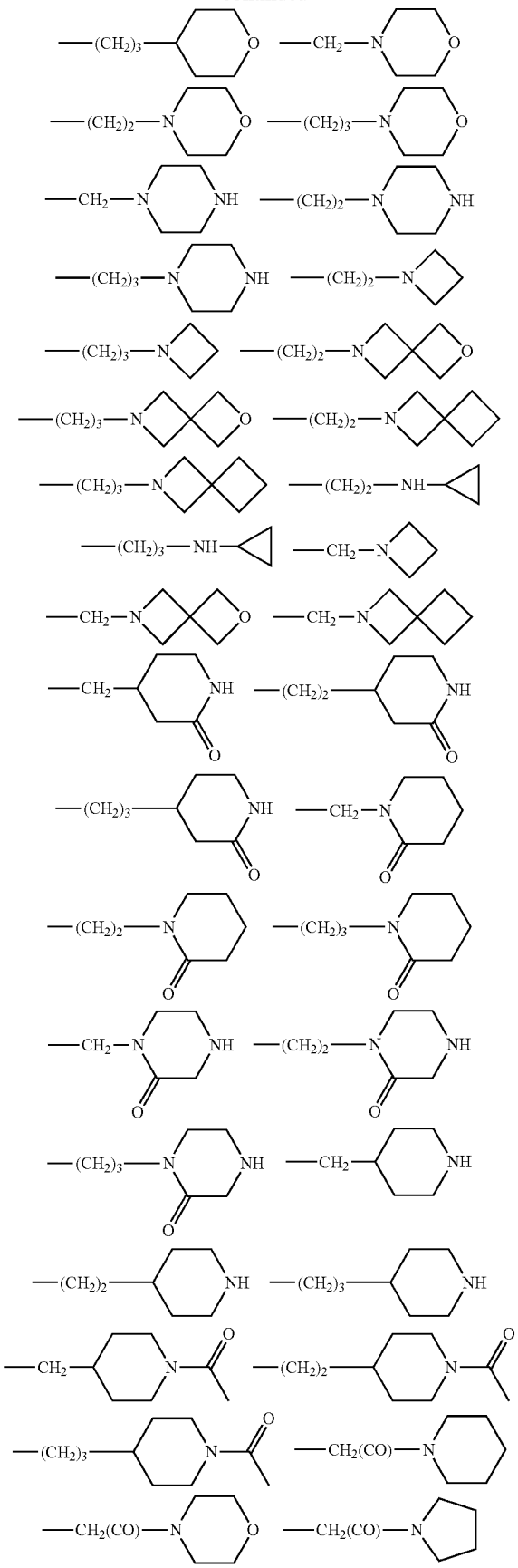

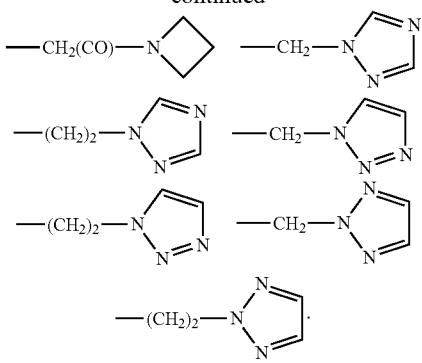

$R^2$ may be any of the groups and substituents identified above with respect to $R^1$, and may, in addition, be a functional group selected from those set forth in part (I) of this Detailed Description. Examples of functional groups that may serve as $R^2$ substituents thus include, without limitation, halo, carboxyl, $C_1$-$C_{12}$ alkoxy, $C_1$-$C_{12}$ alkylsulfanyl, $C_2$-$C_{12}$ acyl, $C_2$-$C_{12}$ acyloxy, $C_2$-$C_{12}$ alkoxycarbonyl, and $C_6$-$C_{18}$ aryloxycarbonyl (—(CO)—O-aryl).

$R^2$, when n is 1 or 2, is typically $C_1$-$C_{12}$ alkyl (e.g., $C_1$-$C_8$ alkyl), $C_1$-$C_{12}$ alkoxy (e.g., $C_1$-$C_8$ alkoxy), $C_2$-$C_{12}$ alkoxyalkyl (e.g., $C_2$-$C_8$ alkoxyalkyl), carboxyl, or halo (with Br and Cl generally preferred), It follows from the above description and substituent definitions that numerous compounds can be produced using the present method. One example of a compound of formula (AA) is olivetol; i.e., the compound is olivetol when $R^1$ is n-pentyl, m is 1, n is zero, and the substituents are in the 1,3,5 configuration. As another example, compound (AA) is divarinol when $R^1$ is n-propyl and, as for olivetol, m is 1, n is zero, and the phenyl ring is 1,3,5-trisubstituted.

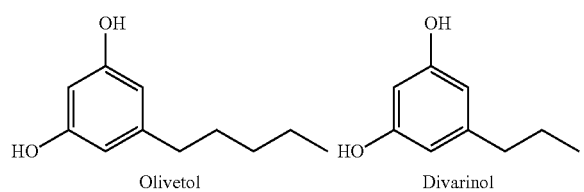

Step 1: Olivetol Divarinol

Synthesis of compounds having the structure of formula (AA) proceeds, initially, by reaction of a starting material having the structure of formula (AA-1)

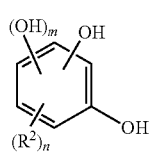

(AA-1)

with an electron-withdrawing hydroxyl-protecting reagent under conditions effective to provide a hydroxyl-protected intermediate having the structure of formula (AA-2)

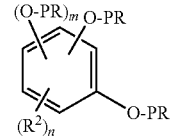

(AA-2)

wherein m, n, and $R^2$ are as defined previously and PR represents an electron-withdrawing hydroxyl-protecting group. The starting material (AA-1) can be obtained commercially or synthesized using procedures known or readily available to one of ordinary skill in the art.

The electron-withdrawing protecting group PR can be one of any number of electron-withdrawing protecting groups. In one embodiment, —O—PR represents a sulfonate ester. In some embodiments, —O—PR may be represented as —O—(SO$_2$)—R$^3$ wherein R$^3$ is selected from: $C_1$-$C_{12}$ hydrocarbyl optionally substituted with one or more non-hydrogen substituents and optionally containing at least one heteroatom; $C_1$-$C_{12}$ perfluorocarbyl; and fluoro. By way of illustration, examples of such protecting groups include tosylate, mesylate, triflate (trifluoromethanesulfonate), benzyl sulfonate, 2-[(4-nitrophenyl)ethyl] sulfonate, and fluorosulfate, corresponding to the following —O—PR moieties:

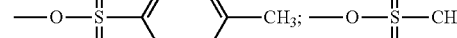

tosylate; mesylate

triflate; benzenesulfonate

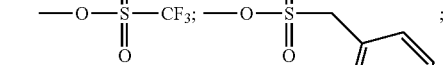

2-[(4-nitrophenyl)ethyl] sulfonate; fluorosulfonate

It is to be understood that the above —O—PR moieties are intended as representative and non-limiting examples of electron-withdrawing protecting groups useful in conjunction with the practice of the invention.

Suitable electron-withdrawing hydroxyl-protecting reagents for effecting protection of the hydroxyl groups as —O—PR will be known to those in the art or found in the pertinent texts and literature, as are the reaction conditions normally employed. For example, the hydroxyl groups of compound (AA-1) can be protected by treatment of (AA-1) using electron-withdrawing hydroxyl-protecting reagents as follows:

Treatment of (AA-1) with p-toluenesulfonyl chloride (Ts-Cl) in approximately equimolar amounts in the presence of a base. e.g., triethylamine, pyridine, dimethylaminopyridine (DMAP), sodium carbonate (NaHCO$_3$), sodium hydroxide, potassium hydroxide, or a combination of any of the foregoing, in a suitable solvent, e.g., aqueous tetrahydrofuran (THF), aqueous toluene, dichloromethane (DCM), or pyridine, at a temperature in the range of about 10° C. to about 40° C., preferably about 30° C. to about 40° C. and with a reaction time of about 0.5 hours to about 5 hours, to provide (AA-2) in which —O—PR is a tosylate ester;

Treatment of (AA-1) with methanesulfonyl chloride ("mesyl chloride") or methanesulfonic anhydride in the presence of a base and in a suitable solvent, both typically selected from those exemplified for tosylation, to provide (AA-2) in which —O—PR is a mesylate;

Treatment of (AA-1) with trifluoromethanesulfonic anhydride in the presence of a base and in a suitable solvent, as before, to provide (AA-2) in which —O—PR is a triflate;

Treatment of (AA-1) with benzenesulfonyl chloride or nitrobenzylsulfonyl chloride in the presence of a base and in a suitable solvent, as before, to provide (AA-2) in which —O—PR is a benzene sulfonate or nitrobenzyl sulfonate, respectively;

Treatment of (AA-1) with 2-[(4-nitrophenyl)ethyl)sulfonyl chloride in the presence of base and in a suitable solvent, as before, to provide (AA-2) in which —O—PR is 2-[(4-nitrophenyl)ethyl)sulfonate; or Treatment of (AA-1) with sulfuryl fluoride in the presence of a base and in a suitable solvent, as before, to provide (AA-2) in which —O—PR is a fluorosulfate ester (see Lekkala et al. (2019) *Organic Chemistry Frontiers* 6: 3490-3516).

The hydroxyl-protected compound (AA-2) may or may not be isolated and purified at this point. It may be preferred, in some instances, that the reaction proceed as a "one pot" reaction without isolation of (AA-2) before continuing. For example, the synthesis of (AA) might be carried out in a flow reactor, where the starting material is introduced at an initial inlet and the final product is obtained downstream without isolation of any intermediates therebetween.

Step 2:

Next, a cross-coupling reaction is carried out between the hydroxyl-protected intermediate (AA-2) and a reactant $R^1$-M in the presence of a catalyst that facilitates the cross-coupling reaction, wherein $R^1$ is as defined earlier and M comprises a metallic element, to provide a compound having the structure of formula (AA-3)

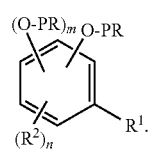

(AA-3)

As the reaction involves the coupling of $R^1$-M to the aromatic ring of compound (AA-2), it will be appreciated that the reaction is an sp2-sp3 cross-coupling reaction. As is known in the art, cross-coupling reactions traditionally involve the metal-catalyzed coupling of an sp2-hybridized substituted aryl electrophile with an organometallic nucleophile, wherein the aryl electrophile may be a phenol derivative or an aryl halide. Numerous techniques are suitable for carrying out this step and have been described in the literature. Among these cross-coupling techniques are:

Negishi cross-coupling, in which the co-reactant $R^1$-M (i.e., the reactant that cross couples with (AA-2)) is typically $R^1$—Zn—X where X is halo, and the catalyst employed is typically a palladium or nickel catalyst (see Negishi et al. (1977), *J. Org. Chem.* 42(10): 1821-23);

Suzuki-Miyaura cross-coupling, in which the co-reactant $R^1$-M is an organoboron reagent $R^1$—$B(OH)_2$ or $R^1$—B$(OR)_2$ (where R is hydrocarbyl), the catalyst is, as in Negishi cross-coupling, generally a palladium or nickel catalyst, and the reaction proceeds in the presence of base (see Miyaura et al. (1995) *Chem. Rev.* 95: 2457-83; and Minard et al. (2014) *Eur. J. Org. Chem.* 2942-55);

Fürstner cross-coupling, in which the co-reactant $R^1$-M is a Grignard reagent having the structure $R^1$—MgBr, and uses an iron-based catalyst, i.e., a salt or an organometallic complex containing iron (e.g., $FeCl_2$, $FeCl_3$, $Fe(acac)_2$, or $Fe(acac)_3$ where "acac" is an acetylacetonate ligand) (see Fürstner et al. (2002) *J. Am. Chem. Soc.* 124(46): 13856-63);

Kumada cross-coupling, in which the co-reactant $R^1$-M is a Grignard reagent $R^1$—MgBr and the catalyst is generally a palladium, nickel, or iron catalyst (Tamao et al. (1976) *Bull. Chem. Soc. Jpn.* 49:1958; and Jiro (1992) *J. Synth. Org. Chem.* 50(12): 1125-30); and Corey-House synthesis, in which the co-reactant $R^1$-M is $(R^1)_2$CuLi or $R^1$—MgBr and a Cu catalyst is usually used (see Posner et al. (1975) *Organic Reactions* 22: 253-400).

The foregoing publications are hereby incorporated by reference with regard to the disclosed reactants, procedures, and reaction conditions that can be used in conjunction with the present invention to provide compound (AA-3).

Preferred cross-coupling reactions herein are carried out at a reaction temperature lower than about 25° C., e.g., lower than about 15° C., lower than about 5° C., lower than about −5°, etc. For example, the cross-coupling reaction temperature may be in the range of about −25° C. to about 25° C., such as about −20° C. to about 20° C., about −15° C. to about 15° C., about −10° C. to about 10° C., about −15° C. to about 5° C., about −15° C. to about 0° C., about −15° C. to about −10° C., about −5° C. to about 5° C., about −25° C. to about 5° C., about −25° C. to about −5° C., or at approximately −10° C.

Negishi, Suzuki-Miyaura and Fürstner cross-coupling are generally preferred herein, with the iron-catalyzed Fürstner coupling particularly preferred, insofar as the reaction can be carried out under relatively mild conditions and iron catalysts tend to be low in cost, non-toxic, and selective.

In one embodiment, introduction of the $R^1$ substituent is carried out using the Fürstner reaction, using about 1 equivalent to about 1.5 equivalents of the Grignard reagent $R^1$—MgBr. The reaction temperature is maintained in the range of about −15° C. to about −5° C., preferably in the range of about −15° C. to about −10° C.; either ferric chloride or ferric acetylacetonate ($Fe(acac)_3$) is used to catalyze the reaction; catalyst load is in the range of about 5 mol % to about 10 mol %; and the reaction is carried out in a solvent such as THF or a THF/toluene mixture in the presence of an additive that facilitates cross-coupling with iron salts (see, e.g., Neidig et al. (2019), "Development and Evolution of Mechanistic Understanding in Iron-Catalyzed Cross-Coupling," *Acc Chem Res* 52(1): 140-150) such as N-methyl pyrrolidone (NMP), tetramethylethylenediamine (TMEDA), N, N'-dimethylethylene urea (DMEU), and N,N'-dimethylpropyleneurea (DMPU). See, e.g., Examples 1 and 3 herein.

It will be appreciated that the $R^1$-M reagents can be selected to provide (AA-3) intermediates having a variety of $R^1$ substituents, wherein $R^1$ is as defined earlier in this section.

Compound (AA-3) can be isolated and purified at this point, although, if desired, the next step of the synthesis, deprotection, can instead proceed without isolation and purification, in the same reaction vessel, as explained with respect to the initial reaction step and the intermediate (AA-2).

The compound having the structure of formula (AA-3) is believed to be a new chemical entity and is claimed as such herein. In one embodiment, m is 1, n is zero, $R^1$ is n-pentyl, and the ring is 1,3,5-trisubstituted, such the compound has the structure (AA-4):

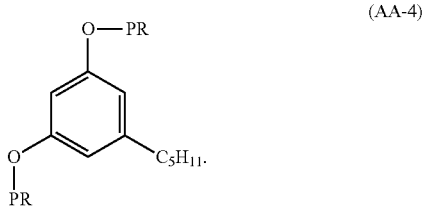

In the final step of this synthesis, compound (AA-3) is deprotected to give the desired end product, compound (AA). Deprotecting reagents and reaction conditions for removal of hydroxyl protecting groups are known to those of ordinary skill in the art, and are described throughout the pertinent texts. See, e.g., Greene et al., "Protective Groups in Organic Synthesis," 3rd Ed. (New York: John Wiley & Sons, 1999). Greene states, for example, that tosyl groups can be removed by reductive cleavage with Na/NH$_3$ or by treatment with sodium borohydride or lithium aluminum hydride. In the present method, tosyl groups are preferably removed by potassium hydroxide, sodium hydroxide, isobutyl alcohol, or t-butyl alcohol. Benzyl sulfonate can be cleaved with sodium amide, while mesylate groups can be removed by photolysis in the presence of potassium iodide, triflate groups can be removed by acid and hydrogenolysis, and fluorosulfate protecting groups can be removed by a strong aqueous base or under hydridic conditions. Following deprotection, the reaction product can be isolated and then purified by any suitable means or combination thereof, e.g., by filtration, extraction, crystallization or recrystallization, use of chromatographic means, or the like. Alternatively, the reaction product can be used without purification in a subsequent synthesis, i.e., in a "one-pot" reaction. For example, the reaction product can be immediately used in synthesizing a cannabinoid such as CBD or an analog thereof as described herein. Also see Example 28, pertaining to the synthesis of olivetol via a telescoped reaction.

In one embodiment, n is zero, such that the starting compound of formula (AA-1) is dihydroxy- or trihydroxybenzene. When m is also zero, it will be appreciated that compound (AA-1) is a dihydroxybenzene, i.e., 1,2-dihydroxybenzene, 1,3-dihydroxybenzene, or 1,4-dihydroxybenzene. When n is zero and m is 1, compound (AA-1) is a trihydroxybenzene, typically 1,2,4-trihydroxybenzene or 1,3,5-trihydroxybenzene. The latter compound is also known as phloroglucinol.

When compound (AA-1), the starting material, is phloroglucinol, and $R^1$ in the $R^1$-M co-reactant is n-pentyl, the reaction product (AA) is olivetol:

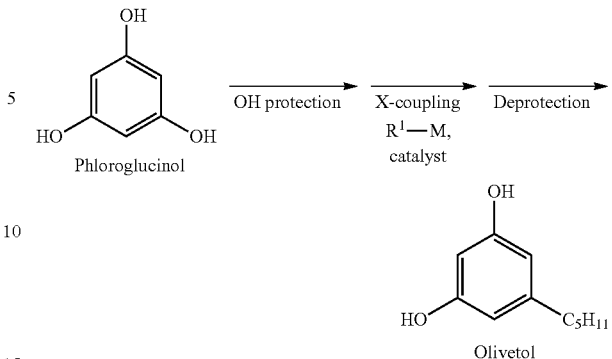

Accordingly, the invention provides, in one embodiment, a method for synthesizing olivetol and analogs thereof, where the method can be scaled up to an efficient and economical process that provides a high purity reaction product and no harmful by-products.

The purified reaction product may be a composition that comprises, in addition to compound (AA), an additional compound in which cross-coupling has occurred at two ring hydroxyl sites instead of one, such that the reaction product comprises a compound having the structure of formula (AA-5) and a compound having the structure of formula (AA-6) wherein:

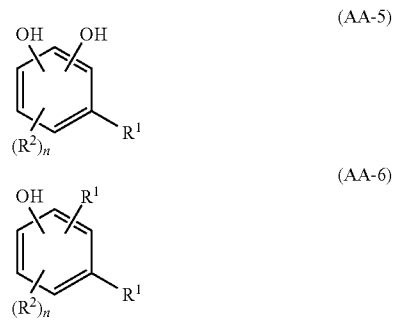

n is zero, 1, or 2;
$R^1$ and $R^2$ are as defined previously for compounds of formula (AA),
wherein when n is 2, the $R^2$ may be the same or different.

The molar ratio of (AA-5) to (AA-6) in the purified reaction product can vary. Generally, (AA-6) represents at most about 2 mol % of the combination of (AA-5) and (AA-6), while (AA-5) correspondingly represents greater than about 98 mol % of (AA-5) plus (AA-6), such that the mol ratio of (AA-5) to (AA-6) is at least about 49:1. More typically, (AA-6) represents at most about 0.1 mol % of the combination of (AA-5) and (AA-6), while (AA-5) correspondingly represents greater than about 99.9 mol % of (AA-5) plus (AA-6). In one embodiment, (AA-6) represents at most about 0.01 mol % of the combination of (AA-5) and (AA-6), while (AA-5) correspondingly represents greater than about 99.99 mol % of (AA-5) plus (AA-6). In another embodiment, (AA-6) represents in the range of about 0.001 mol % to about 2 mol % of the combination of (AA-5) and (AA-6), with (AA-5) correspondingly represents about 98 mol % to about 99.999 mol % of the (AA-5) plus (AA-6) combination.

When the starting material (AA-1) is phloroglucinol, compounds (AA-5) and (AA-6) will have the structures of compounds (AA-7) and (AA-8), respectively:

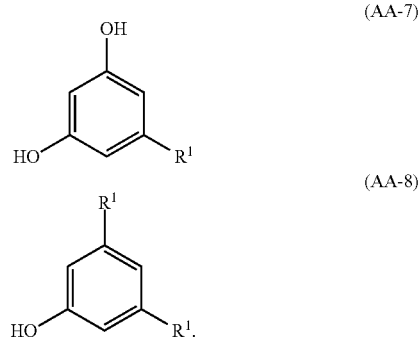

The substituent $R^1$ is as defined previously for compounds having structure (AA).

Representative (AA) Compounds:

It will be appreciated that a variety of compounds are encompassed by (AA) and can be synthesized using the above-described method. These include the following compounds collectively referred to herein as "(AA)-type compounds":

1,3-dihydroxybenzene, 1,2-dihydroxybenzene, or 1,4-dihydroxybenzene substituted at the 5-position with substituted or unsubstituted $C_1$-$C_{12}$ alkyl containing zero to 3 heteroatoms; substituted or unsubstituted $C_2$-$C_{12}$: alkenyl containing zero to 3 heteroatoms, substituted or unsubstituted $C_2$-$C_{12}$: alkynyl containing zero to 3 heteroatoms, including straight-chain, branched, and cyclic moieties that may be substituted or unsubstituted and/or heteroatom-containing;

phenol ortho, para, or meta-substituted with substituted or unsubstituted $C_1$-$C_{12}$ alkyl containing zero to 3 heteroatoms; substituted or unsubstituted $C_2$-$C_{12}$: alkenyl containing zero to 3 heteroatoms, substituted or unsubstituted $C_2$-$C_{12}$: alkynyl containing zero to 3 heteroatoms, including straight-chain, branched, and cyclic moieties that may be substituted or unsubstituted and/or heteroatom-containing; and phenol ortho and meta di-substituted, ortho and pare di-substituted, or meta and pare di-substituted with two substituents that are the same or different and are selected from substituted or unsubstituted $C_1$-$C_{12}$ alkyl containing zero to 3 heteroatoms; substituted or unsubstituted $C_2$-$C_{12}$ alkenyl containing zero to 3 heteroatoms, substituted or unsubstituted $C_2$-$C_{12}$: alkynyl containing zero to 3 heteroatoms, including straight-chain, branched, and cyclic moieties that may be substituted or unsubstituted and/or heteroatom-containing.

III. Synthesis of CBD, CBD Analogs, and Other Cannabinoids

A Synthesis of CBD and CBD Analogs from Compound (AA):

In another embodiment, a method is provided for the synthesis of cannabidiol or analogs thereof from the compound synthesized in the preceding section, i.e., compound (AA), which may, as noted previously, be olivetol per Se. Compound (AA) may be isolated and purified prior to use in this synthesis, using conventional means or methods readily apparent to those of ordinary skill in the art. However, compound (AA) can be used in this synthesis as prepared, without isolation and purification.

In this embodiment, the method results in the synthesis of a compound having the structure of formula (CC) wherein:

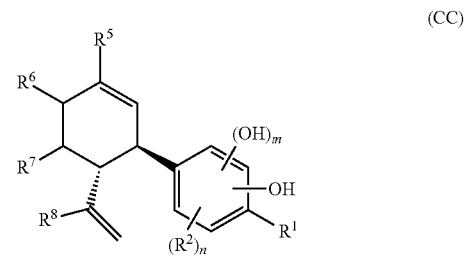

m is zero or 1;

n is zero, 1, or 2;

$R^1$ and $R^2$ are defined as for compounds of formula (AA);

$R^5$ is H, carboxyl, $C_2$-$C_6$ acyloxy, $C_2$-$C_6$ alkoxycarbonyl, $C_1$-$C_6$ alkyl, or $C_1$-$C_6$ alkyl substituted with hydroxyl, carboxyl, or halo;

$R^6$ and $R^7$ are independently selected from H, $C_1$-$C_{12}$ hydrocarbyl, substituted $C_1$-$C_{12}$ hydrocarbyl, heteroatom-containing $C_1$-$C_{12}$ hydrocarbyl, substituted heteroatom-containing $C_1$-$C_{12}$ hydrocarbyl, and functional groups; and $R^8$ is methyl, hydroxymethyl, or halomethyl.

In some embodiments, $R^1$ is selected from:

$C_1$-$C_{18}$ alkyl (e.g., $C_1$-$C_{12}$ alkyl, $C_1$-$C_{10}$ alkyl, or $C_1$-$C_8$ alkyl, such as methyl, ethyl, n-propyl, isopropyl, n-butyl, isobutyl, t-butyl, n-pentyl, cyclohexyl, and the like);

$C_2$-$C_{18}$ alkenyl (e.g., $C_2$-$C_{12}$ alkenyl, $C_2$-$C_{10}$ alkenyl or $C_2$-$C_8$ alkenyl);

$C_2$-$C_{18}$ alkynyl (e.g., $C_2$-$C_{12}$ alkynyl, $C_2$-$C_{10}$ alkynyl or $C_2$-$C_8$ alkynyl);

$C_6$-$C_{18}$ aralkyl (e.g., $C_5$-$C_6$ aryl-substituted $C_1$-$C_{12}$ alkyl or $C_5$-$C_6$ aryl-substituted $C_1$-$C_8$ alkyl);

$C_4$-$C_{16}$ heteroaralkyl (e.g., $C_3$-$C_6$ heteroaryl-substituted $C_1$-$C_{10}$ alkyl or $C_3$-$C_6$ heteroaryl-substituted $C_1$-$C_8$ alkyl), wherein the heteroaryl substituent may be saturated or unsaturated;

$C_1$-$C_{18}$ haloalkyl (e.g., $C_1$-$C_{12}$ chloroalkyl, $C_1$-$C_{10}$ chloroalkyl, $C_1$-$C_8$ chloroalkyl, $C_1$-$C_{12}$ fluoroalkyl, $C_1$-$C_{10}$ fluoroalkyl, or $C_1$-$C_8$ fluoroalkyl);

$C_1$-$C_{18}$ hydroxyalkyl (e.g., $C_1$-$C_{12}$ hydroxyalkyl, $C_1$-$C_{10}$ hydroxyalkyl, or $C_1$-$C_8$ hydroxyalkyl);

$C_2$-$C_{18}$ haloalkenyl (e.g., $C_2$-$C_{12}$ chloroalkenyl, $C_2$-$C_{10}$ chloroalkenyl, $C_2$-$C_8$ chloroalkenyl, $C_2$-$C_{12}$ fluoroalkenyl, $C_2$-$C_{10}$ fluoroalkenyl or $C_2$-$C_6$ fluoroalkenyl);

$C_2$-$C_{18}$ haloalkynyl (e.g., $C_2$-$C_{12}$ chloroalkynyl, $C_2$-$C_{10}$ chloroalkynyl, $C_2$-$C_8$ chloroalkynyl, $C_2$-$C_{12}$ fluoroalkynyl, $C_2$-$C_{10}$ fluoroalkynyl or $C_2$-$C_6$ fluoroalkynyl);

$C_2$-$C_{18}$ alkoxyalkyl (e.g., ($C_1$-$C_8$ alkoxy)-substituted $C_1$-$C_{12}$ alkyl or ($C_1$-$C_8$ alkoxy)-substituted $C_1$-$C_8$ alkyl);

$C_2$-$C_{18}$ alkoxyalkenyl (e.g., ($C_1$-$C_8$ alkoxy)-substituted $C_2$-$C_{12}$ alkenyl or ($C_1$-$C_8$ alkoxy)-substituted $C_2$-$C_8$ alkenyl);

$C_2$-$C_{12}$ alkoxyalkynyl (e.g., ($C_1$-$C_8$ alkoxy)-substituted $C_2$-$C_{12}$ alkynyl or ($C_1$-$C_8$ alkoxy)-substituted $C_2$-$C_8$ alkynyl);

$C_2$-$C_{18}$ carboxyalkyl (e.g., $C_2$-$C_{12}$ carboxyalkyl, $C_2$-$C_{10}$ carboxyalkyl, or $C_2$-$C_8$ carboxyalkyl), $C_3$-$C_{18}$ carboxyalkenyl (e.g., $C_3$-$C_{12}$ carboxyalkenyl, $C_3$-$C_{10}$ carboxyalkenyl, or $C_3$-$C_8$ carboxyalkenyl), $C_1$-$C_{18}$ alkyl, e.g., $C_1$-$C_{12}$ alkyl, substituted with mono-($C_1$-$C_8$ alkyl)-substituted carbamoyl (—(CO)—NH($C_1$-$C_8$ alkyl)) or di-($C_1$-$C_8$ alkyl)-substituted carbamoyl (—(CO)—N($C_1$-$C_8$ alkyl)$_2$);

$C_2$-$C_{18}$ alkenyl, e.g., $C_2$-$C_{12}$ alkenyl, substituted with mono-($C_1$-$C_8$ alkyl)-substituted carbamoyl (—(CO)—NH($C_1$-$C_8$ alkyl)) or di-($C_1$-$C_8$ alkyl)-substituted carbamoyl (—(CO)—N($C_1$-$C_{12}$ alkyl)$_2$);

$C_1$-$C_{18}$ alkyl, e.g., $C_1$-$C_{12}$ alkyl, substituted with $C_2$-$C_8$ alkylamido (—NH—(CO)-alkyl);

$C_2$-$C_{18}$ alkenyl (e.g., $C_2$-$C_{12}$ alkenyl, $C_2$-$C_{10}$ alkenyl or $C_2$-$C_8$ alkenyl);

$C_2$-$C_{18}$ alkynyl (e.g., $C_2$-$C_{12}$ alkynyl, $C_2$-$C_{10}$ alkynyl or $C_2$-$C_8$ alkynyl);

$C_6$-$C_{18}$ aralkyl (e.g., $C_5$-$C_6$ aryl-substituted $C_1$-$C_{12}$ alkyl or $C_5$-$C_6$ aryl-substituted $C_1$-$C_8$ alkyl);

$C_4$-$C_{16}$ heteroaralkyl (e.g., $C_3$-$C_6$ heteroaryl-substituted $C_1$-$C_{10}$ alkyl or $C_3$-$C_6$ heteroaryl-substituted $C_1$-$C_8$ alkyl), wherein the heteroaryl substituent may be saturated or unsaturated;

$C_1$-$C_{18}$ haloalkyl (e.g., $C_1$-$C_{12}$ chloroalkyl, $C_1$-$C_{10}$ chloroalkyl, $C_1$-$C_8$ chloroalkyl, $C_1$-$C_{12}$ fluoroalkyl, $C_1$-$C_{10}$ fluoroalkyl, or $C_1$-$C_8$ fluoroalkyl);

$C_1$-$C_{18}$ hydroxyalkyl (e.g., $C_1$-$C_{12}$ hydroxyalkyl, $C_1$-$C_{10}$ hydroxyalkyl, or $C_1$-$C_8$ hydroxyalkyl);

$C_2$-$C_{18}$ haloalkenyl (e.g., $C_2$-$C_{12}$ chloroalkenyl, $C_2$-$C_{10}$ chloroalkenyl, $C_2$-$C_8$ chloroalkenyl, $C_2$-$C_{12}$ fluoroalkenyl, $C_2$-$C_{10}$ fluoroalkenyl or $C_2$-$C_6$ fluoroalkenyl);

$C_2$-$C_{18}$ haloalkynyl (e.g., $C_2$-$C_{12}$ chloroalkynyl, $C_2$-$C_{10}$ chloroalkynyl, $C_2$-$C_8$ chloroalkynyl, $C_2$-$C_{12}$ fluoroalkynyl, $C_2$-$C_{10}$ fluoroalkynyl or $C_2$-$C_6$ fluoroalkynyl);

$C_2$-$C_{18}$ alkoxyalkyl (e.g., ($C_1$-$C_8$ alkoxy)-substituted $C_1$-$C_{12}$ alkyl or ($C_1$-$C_8$ alkoxy)-substituted $C_1$-$C_8$ alkyl);

$C_2$-$C_{18}$ alkoxyalkenyl (e.g., ($C_1$-$C_8$ alkoxy)-substituted $C_2$-$C_{12}$ alkenyl or ($C_1$-$C_8$ alkoxy)-substituted $C_2$-$C_8$ alkenyl);

$C_2$-$C_{12}$ alkoxyalkynyl (e.g., ($C_1$-$C_8$ alkoxy)-substituted $C_2$-$C_{12}$ alkynyl or ($C_1$-$C_8$ alkoxy)-substituted $C_2$-$C_8$ alkynyl);

$C_2$-$C_{18}$ carboxyalkyl (e.g., $C_2$-$C_{12}$ carboxyalkyl, $C_2$-$C_{10}$ carboxyalkyl, or $C_2$-$C_8$ carboxyalkyl), $C_3$-$C_{18}$ carboxyalkenyl (e.g., $C_3$-$C_{12}$ carboxyalkenyl, $C_3$-$C_{10}$ carboxyalkenyl, or $C_3$-$C_8$ carboxyalkenyl), $C_1$-$C_{18}$ alkyl, e.g., $C_1$-$C_{12}$ alkyl, substituted with mono-($C_1$-$C_8$ alkyl)-substituted carbamoyl (—(CO)—NH($C_1$-$C_8$ alkyl)) or di-($C_1$-$C_8$ alkyl)-substituted carbamoyl (—(CO)—N($C_1$-$C_8$ alkyl)$_2$);

$C_2$-$C_{18}$ alkenyl, e.g., $C_2$-$C_{12}$ alkenyl, substituted with mono-($C_1$-$C_8$ alkyl)-substituted carbamoyl (—(CO)—NH($C_1$-$C_8$ alkyl)) or di-($C_1$-$C_8$ alkyl)-substituted carbamoyl (—(CO)—N($C_1$-$C_{12}$ alkyl)$_2$);

$C_1$-$C_{18}$ alkyl, e.g., $C_1$-$C_{12}$ alkyl, substituted with $C_2$-$C_8$ alkylamido (—NH—(CO)-alkyl);

$C_2$-$C_{18}$ alkenyl, e.g., $C_2$-$C_{12}$ alkenyl, substituted with $C_2$-$C_8$ alkylamido (—NH—(CO)-alkenyl);

$C_1$-$C_{18}$ alkyl, e.g., $C_1$-$C_{12}$ alkyl, substituted with —NH—($C_1$-$C_8$ alkyl) or —N($C_1$-$C_8$ alkyl)$_2$;

$C_2$-$C_{18}$ alkenyl, e.g., $C_2$-$C_{12}$ alkenyl, substituted with —NH—($C_1$-$C_8$ alkyl) or —N($C_1$-$C_8$ alkyl)$_2$;

$C_1$-$C_{18}$ alkyl, e.g., $C_1$-$C_{12}$ alkyl, substituted with $C_1$-$C_8$ alkylsulfonyl (—SO$_2$-alkyl);

$C_2$-$C_{18}$ alkenyl, e.g., $C_2$-$C_{12}$ alkenyl, substituted with $C_1$-$C_8$ alkylsulfonyl (—SO$_2$-alkyl);

$C_1$-$C_{18}$ alkyl, e.g., $C_1$-$C_{12}$ alkyl, substituted with $C_0$-$C_8$ sulfonamido (—SO$_2$—NH$_2$ or —SO$_2$—N alkyl);

$C_2$-$C_{18}$ alkenyl, e.g., $C_2$-$C_{12}$ alkenyl, substituted with $C_0$-$C_8$ sulfonamido (—SO$_2$—NH$_2$ or —SO$_2$—N alkyl);

$C_1$-$C_{18}$ alkyl, e.g., $C_1$-$C_{12}$ alkyl, substituted with oxanyl, morpholino, diazinanyl, generally at the nitrogen atom of a nitrogen heterocycle, as in morpholino and diazinanyl; or $C_2$-$C_{18}$ alkenyl, e.g., $C_2$-$C_{12}$ alkenyl, substituted with oxanyl, morpholino, diazinanyl, generally at the nitrogen atom of a nitrogen heterocycle, as in morpholino and diazinanyl.

As before, any of the foregoing representative $R^1$ substituents may be further substituted with one or more additional substituents that may or may not be the same as the substituents identified above. Examples of such $R^1$ substituents include a $C_1$-$C_{18}$ alkyl group (e.g., a $C_1$-$C_{12}$ alkyl group $C_1$-$C_{10}$ alkyl, or $C_1$-$C_8$ alkyl group) disubstituted with Cl or F; a $C_2$-$C_{18}$ alkoxyalkyl group substituted with one or more $C_2$-$C_{18}$ alkoxyalkyl groups, e.g., a $C_2$-$C_{12}$ alkoxyalkyl group having the structure ($C_1$-$C_6$ alkoxy)-substituted $C_1$-$C_{12}$ alkyl, wherein the $C_1$-$C_{12}$ alkyl is substituted with an additional $C_2$-$C_{12}$ alkoxyalkyl group; a $C_2$-$C_{18}$ alkoxyalkyl group substituted with one or more heterocyclic substituents such as oxanyl, morpholino, or diazinanyl, generally by linking to a nitrogen atom within the heterocycle, if present.

In some embodiments, $R^1$ is selected from the representative $R^1$ substituents as defined and exemplified in Section II, above.

In this embodiment, compound (AA), which may be obtained commercially or used as synthesized as described in Section II, undergoes a Lewis acid-catalyzed coupling reaction with a second reactant having the structure of formula (CC-1)

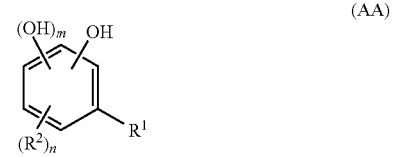

(AA)

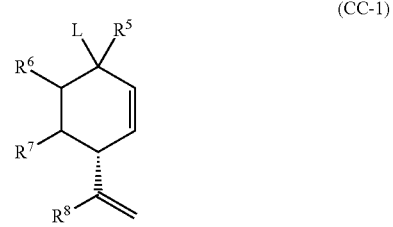

(CC-1)

wherein L is a leaving group such as hydroxyl, triflate, Br, Cl, or the like, with hydroxyl preferred; and $R^5$ through $R^8$ are defined above. The reaction results in the reaction product (CC)

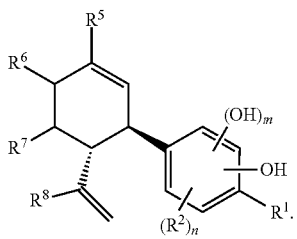

When compound (AA) has the structure (AA-9)

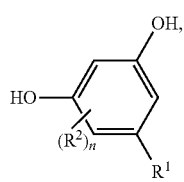

the reaction product (CC) then has the structure (CC-2)

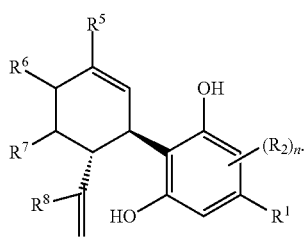

When L is hydroxyl, $R^5$ and $R^8$ are methyl, and $R^6$ and $R^7$ are H, the reactant of formula (CC-1) is p-menthadienol, i.e.,

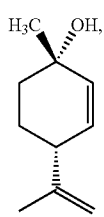

and the reaction product with (AA-9) then has the structure (CC-3)

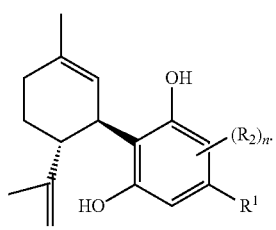

When n is zero, the reaction product has the structure of formula (CC-4)

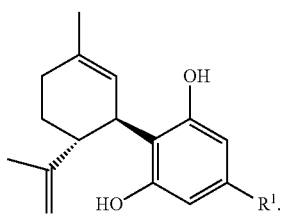

$R^1$ in reactant (AA) can be varied to provide many different cannabinoids, e.g., CBD analogs, substituted at the 4' position (the location of the $R^1$ substituent). It will be understood that when $R^1$ is n-pentyl, the compound of formula (CC-4) is CBD, and when $R^1$ is n-propyl, the compound of formula (CC-4) is CBDV. Cyclization of CBDV, the penultimate intermediate in the synthesis of THCV, can be carried out using methods known to those of ordinary skill in the art and/or described in the pertinent texts and literature with respect to synthesis of either THCV or THC.

The reaction between reactant (AA) and reactant (CC-1) to provide compound (CC) is essentially an electrophilic aromatic substitution reaction and requires a Lewis acid catalyst. As is understood in the art, and as alluded to earlier herein with respect to synthesis of the (AA) reactant, Lewis acid catalysts are based on metals such as aluminum, boron, nickel, silicon, tin, titanium, iron, copper, zinc, and palladium, with aluminum and boron catalysts being most common and generally preferred herein for the reaction of (AA) with (CC-1). Representative Lewis acid catalysts that can be advantageously employed for the reaction include, without limitation, boron trichloride, boron trifluoride, boron trifluoride ethyl etherate, iron (III) bromide, iron (III) chloride, aluminum chloride, and aluminum bromide. An exemplary Lewis acid catalyst for the reaction is boron trifluoride ($BF_3$), which may be in the form of an organic complex, e.g., $BF_3$ etherate ($BF_3 \cdot Et_2O$), optionally used in conjunction with a metal oxide support such as zeolite or alumina.

The coupling of the two reactants is carried out in a suitable organic solvent, e.g., heptane, dichloroethane (DCE), dichloromethane (DCM), N-methylpyrrolidone (NMP), chlorobenzene, or the like, in an inert atmosphere (e.g., under argon), at an elevated temperature in the range of about 30° C. to about 140° C., or about 30° C. to about 130° C., or about 35° C. to about 100° C., such as 35° C., 40° C., 65° C., 80° C., 85° C., or 90° C., typically although not necessarily at reflux. The reaction is quenched with sodium bisulfate or another suitable base, and the product is extracted with diethyl ether or another organic solvent effective to extract the desired product. See Examples 4 and 5. An excess of the (AA) reactant may, in some cases, be desired in order to reduce the presence of one or more contaminants such as abn-CBD and tetrahydrocannabinol (THC) in the synthesis of CBD. The yield of the reaction is in the range of about 30% to about 60%, with the desired reaction product (CC) obtained as at least about 95% pure.

Following completion of the synthesis, the reaction product obtained may be modified to provide other desired analogs as explained in Part III of this section.

As may be deduced from Examples 4-20, the selected solvent, reaction temperature, catalyst loading, and stoichiometry may be varied to optimize the composition of the reaction product, e.g., by reducing the presence of contaminants, and to maximize yield. Use of a molecular sieve is also advantageous in minimizing incidental formation of contaminants, particularly THC.

When the reactant of formula (AA) has the structure of formula (AA-8)

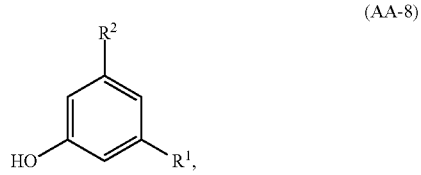
(AA-8)

the reaction product comprises a mixture of two regioisomers having the structures of formula (CC-4A) and (CC-4B):

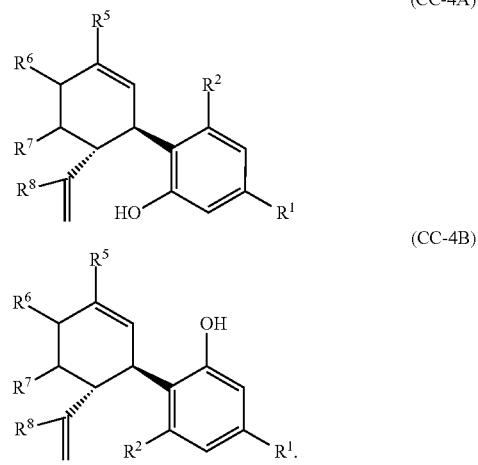
(CC-4A)

(CC-4B)

When $R^5$ and $R^8$ are methyl, and $R^6$ and $R^7$ are H, isomers of formula (CC-4A) and formula (CC-4B) result that have the structures of formula (CC-5A) and formula CC-5B), respectively:

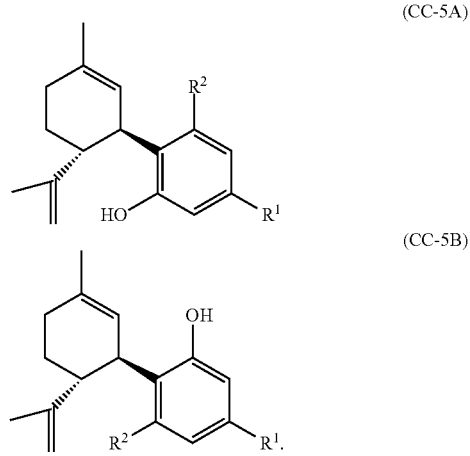
(CC-5A)

(CC-5B)

The reaction product composition generally comprises at least about 98 mol % compound (CC-5), such as at least about 99.9 mol % compound (CC-5), or at least about 99.999 mol % compound (CC-5). In one embodiment, the at least one additional compound selected from (CC-5A) and (CC-5B), and (CC-5C) represents in the range of about 0.001 mol % to about 2 mol % of the composition.

It is to be understood that the menthadienol ring of the CBD analog (CC-1) synthesized as just described may be substituted in different ways and the substituents having different possible configurations, depending on the particular (AA)-type reactant selected. See "Representative (AA) Reactants" in Section II. For instance, 8,9-dehydro analogs of structure (CC), including 8,9-dihydrocannabidiol ($H_2$CBD) and variations thereof, may be prepared from α-phellandrene or via the Friedel-Crafts reaction described in Millimaci et al. (Jun. 8, 2023, Version 1) *ChemRxiv*, doi 10.26434/chemrxiv-2023-7wtzg, the disclosure of which is incorporated by reference herein.

B. Synthesis of Cannabinoids from Compound (AB-1):

In a variation on the method of part A, the starting material that reacts with reactant (CC-4) is the compound (AB-1)

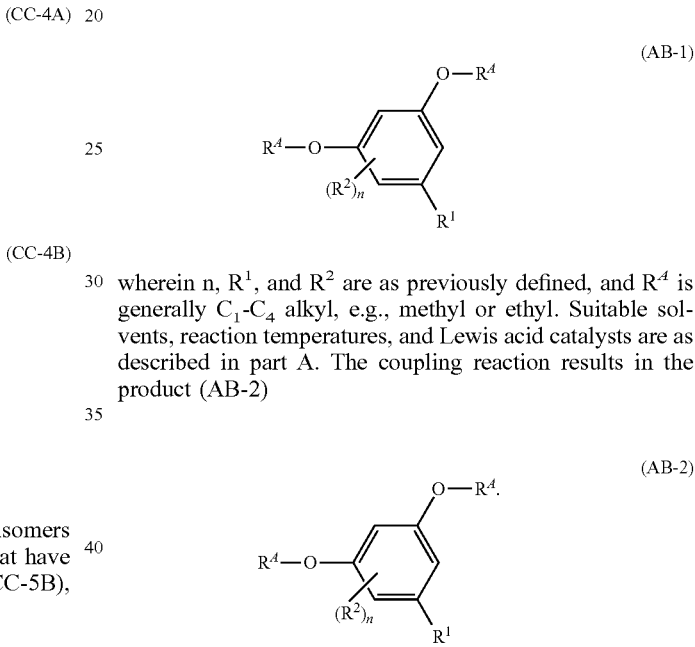
(AB-1)

wherein n, $R^1$, and $R^2$ are as previously defined, and $R^4$ is generally $C_1$-$C_4$ alkyl, e.g., methyl or ethyl. Suitable solvents, reaction temperatures, and Lewis acid catalysts are as described in part A. The coupling reaction results in the product (AB-2)

(AB-2)

When the co-reactant (CC-1) has the structure (3), it will be appreciated that the reaction product has the structure of formula (CC-6)

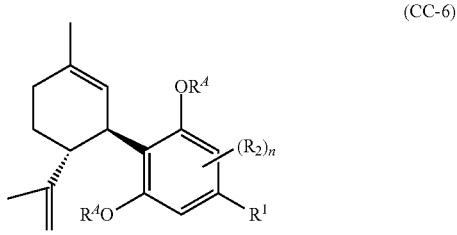
(CC-6)

A representative reaction is included herein in Example 20. As with the cross-coupling reaction described in part A, a variety of analogs can be synthesized in this way by selection of appropriately substituted reactants. For example, analogs of CBD having modifications at the 4' position may be prepared by starting with a reactant (AB-1) having the desired $R^1$ substituent.

C Synthesis of CBD, CBD Analogs, and Other Cannabinoids Via Ketone Route:

In another embodiment of the invention, an alternative method is provided for synthesizing a cannabinoid such as CBD, the cannabinoid having the structure of formula (DD)

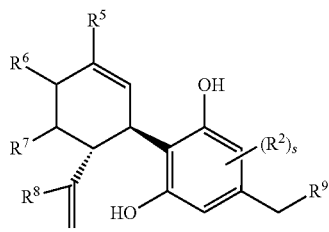

(DD)

that relies on a ketone intermediate in a synthesis that begins with an optionally substituted hydroxyl-protected 3,5-dihydroxybenzoic acid (DD-1) as starting material.

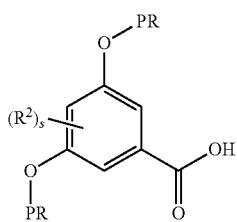

(DD-1)

In the above molecular structures:

s is zero, 1 or 2;

$R^1$ and $R^2$ are as defined previously in the preceding sections, with the proviso that when s is 2, the $R^2$ may be the same or different;

$R^5$ is H, carboxyl, $C_2$-$C_6$ acyloxy, $C_2$-$C_6$ alkoxycarbonyl, $C_1$-$C_6$ alkyl, or $C_1$-$C_6$ alkyl substituted with hydroxyl, carboxyl, or halo;

$R^6$ and $R^7$ are independently selected from $C_1$-$C_{12}$ hydrocarbyl, substituted $C_1$-$C_{12}$ hydrocarbyl, heteroatom-containing $C_1$-$C_{12}$ hydrocarbyl, substituted heteroatom-containing $C_1$-$C_{12}$ hydrocarbyl, and functional groups;

$R^8$ is methyl, hydroxymethyl, or halomethyl;

$R^9$ is selected from $C_1$-$C_{11}$ hydrocarbyl, substituted $C_1$-$C_{11}$ hydrocarbyl, heteroatom-containing $C_1$-$C_{11}$ hydrocarbyl, and substituted heteroatom-containing $C_1$-$C_{11}$ hydrocarbyl; and PR is an electron-withdrawing hydroxyl-protecting group as described earlier herein.

The starting material may be obtained commercially, e.g., as benzyloxy-protected 3,5-dihydroxybenzoic acid, and modified to include one or more $R^2$ substituents, or a desired $R^2$-substituted analog of may be purchased and used without modification, The initial step of the synthesis involves reacting (DD-1) with $R^9$—Li under reducing conditions to provide a hydroxyl-protected ketone intermediate having the structure (DD-2)

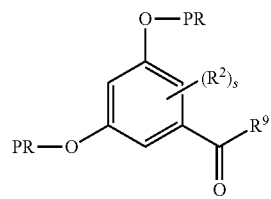

(DD-2)

This can be accomplished, as is known in the art, by treatment of the carboxylic acid (DD-1) with sodium hydride, followed by reaction with the appropriately substituted lithium reagent, i.e., $R^9$—Li herein. The hydroxyl-protected ketone (DD-2) is then deprotected to generate free hydroxyl groups and provide ketone intermediate (DD-3)

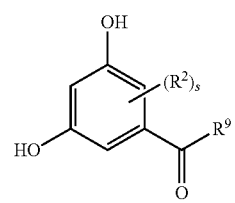

(DD-3)

When benzyloxy protecting groups are used, i.e., if the hydroxyl groups of the starting compound (DD-1) are benzyloxy protected, deprotection can be readily accomplished by hydrogenation using a Pd/C catalyst. Deprotection reactions are known in the art, and discussed in Section II with regard to deprotection of compound (AA-4).

In the next step, intermediate (DD-3) undergoes an electrophilic addition reaction with compound (CC-1), i.e., the menthadienol reactant as defined earlier herein

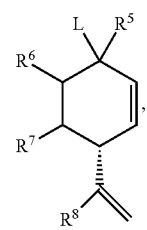

(CC-1)

such that compound (CC-1) is added at the 4-position of (DD-3) in the presence of a Lewis Acid catalyst, to form the immediate precursor to compound (DD), i.e., compound (DD-4):

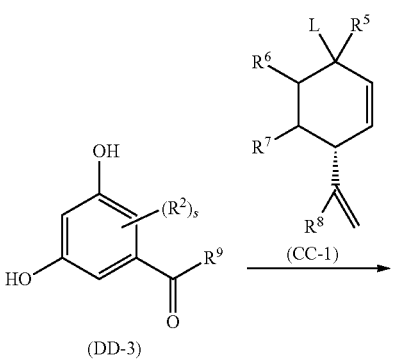

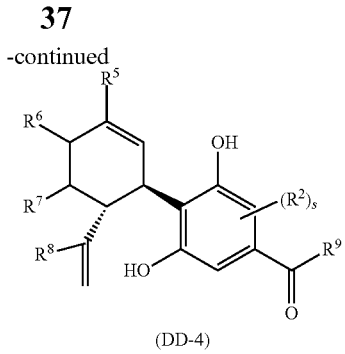

(DD-4)

Compound (DD-4) is then decarbonylated using conventional means to yield the product (DD-3).

Like the syntheses described in Parts A and B of this section, this method is efficient and economical, enables the use of mild reaction conditions without need for harsh reagents or special precautions, is readily adapted to produce a variety of cannabinoids, including, but not limited to, CBD analogs as well as CBD per se, and has little or no potential for incidental production of THC.

D. Alternative Synthesis of CBD, CBD Analogs, and Other Cannabinoids:

In another embodiment of the invention, a method is provided for synthesizing a compound having the structure of formula (BB) wherein:

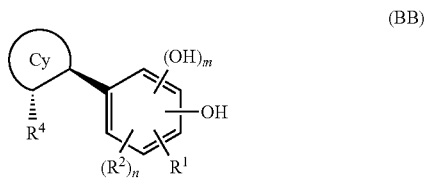

(BB)

m is zero or 1;

n is zero, 1, or 2;

$R^1$ and $R^2$ are defined as for compounds of formula (AA);

$R^4$ is H, $C_2$-$C_6$ alkenyl, or $C_1$-$C_6$ alkyl, and if $C_2$-$C_6$ alkenyl or $C_1$-$C_6$ alkyl, optionally substituted with a non-hydrogen substituent selected from hydroxyl, carboxyl, and halo; and Cy is a four- to seven-membered cyclic group that is either substituted or unsubstituted and optionally contains 1-3 heteroatoms. In a preferred embodiment, Cy is a five- to seven-membered hydrocarbyl ring, e.g., cyclohexyl, cyclohexenyl, or phenyl, optionally substituted with a $C_1$-$C_{12}$ hydrocarbyl group or a functional group.

In one aspect of the embodiment:

$R^4$ is selected from isopropyl, isopropenyl, hydroxyethyl, and hydroxypropyl; and Cy is selected from cyclohexyl, cyclohexenyl, and phenyl, optionally substituted with one or two $C_1$-$C_6$ alkyl, $C_1$-$C_6$ alkoxy, carboxyl, or halo substituents.

The method comprises:

(a) reacting a compound having the structure of formula (BB-1)

(BB-1)

with an electron-withdrawing hydroxyl-protecting reagent under conditions effective to provide a hydroxyl-protected intermediate having the structure of formula (BB-2)

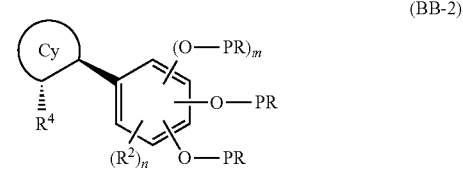

(BB-2)

in which PR represents an electron-withdrawing hydroxyl protecting group;

(b) effecting a cross-coupling reaction between the hydroxyl-protected intermediate (BB-2) and a reactant $R^1$-M in the presence of a catalyst that facilitates the cross-coupling reaction, wherein M comprises a metallic element, to provide a compound having the structure (BB-3)

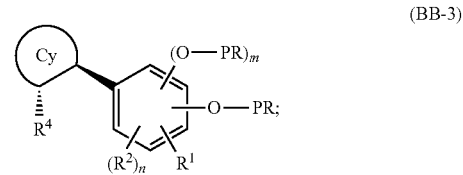

(BB-3)

and (c) treating compound (BB-3) with a reagent composition effective to remove the hydroxyl protecting groups and provide compound (BB).

Suitable electron-withdrawing hydroxyl-protecting reagents, PR moieties, hydroxyl-protecting techniques, deprotection techniques, cross-coupling reaction techniques, cross-coupling catalysts, and cross-coupling reaction conditions are as set forth with respect to the synthesis of compound (AA) in Section II.

In a related aspect of this embodiment, a method is provided for synthesizing a compound having the structure of formula (CC)

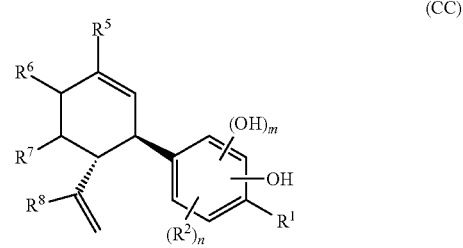

(CC)

wherein m, n, $R^1$, $R^2$, and $R^5$ through $R^8$ are as defined previously.

The method comprises:
(a) reacting a compound having the structure of formula (BA-1)

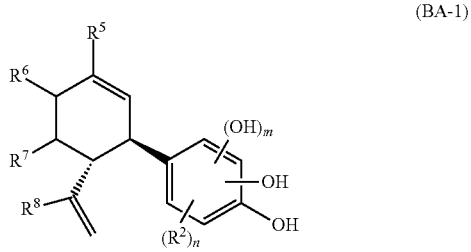

(BA-1)

with an electron-withdrawing hydroxyl-protecting reagent as before under conditions effective to provide a hydroxyl-protected intermediate having the structure of formula (BA-2)

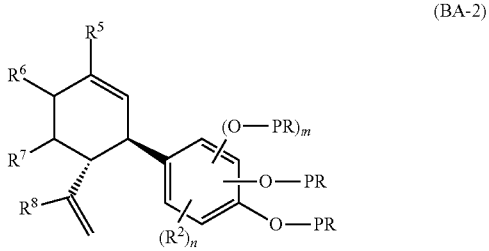

(BA-2)

in which PR represents an electron-withdrawing hydroxyl protecting group as defined previously;
(b) effecting a cross-coupling reaction between the hydroxyl-protected intermediate (BA-2) and a reactant $R^1$-M in the presence of a catalyst that facilitates the cross-coupling reaction, wherein $R^1$-M is defined as in Section II, to provide a compound having the structure (BA-3)

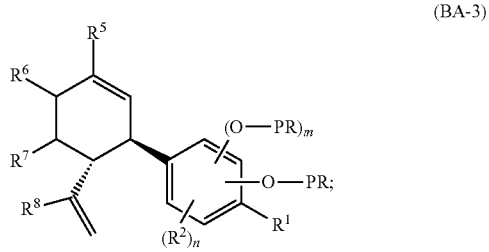

(BA-3)

(c) treating the compound (BA-3) with a deprotecting reagent effective to remove the hydroxyl protecting groups and provide compound (CC), which can either be isolated and purified using standard techniques or be used directly, after preparation, in a subsequent reaction.

Reagents, reactants, techniques, and reaction conditions appropriate for carrying out steps (a) through (b) in the synthesis of compound (CC) are analogous to, and for the most part, the same as, those described in Section II with respect to synthesis of the CBD precursor, the olivetol analog having the structure of formula (AA).

In one embodiment,
$R^1$ is selected from $C_1$-$C_{12}$ hydrocarbyl, substituted $C_1$-$C_{12}$ hydrocarbyl, heteroatom-containing $C_1$-$C_{12}$ hydrocarbyl, and substituted heteroatom-containing $C_1$-$C_{12}$ hydrocarbyl;
$R^2$ is selected from $C_1$-$C_{12}$ hydrocarbyl, substituted $C_1$-$C_{12}$ hydrocarbyl, heteroatom-containing $C_1$-$C_{12}$ hydrocarbyl, substituted heteroatom-containing $C_1$-$C_{12}$ hydrocarbyl, and functional groups, and wherein when n is 2, the $R^2$ may be the same or different;
$R^5$ is H, carboxyl, $C_2$-$C_6$ acyloxy, $C_2$-$C_6$ alkoxycarbonyl, $C_1$-$C_6$ alkyl, or $C_1$-$C_6$ alkyl substituted with hydroxyl, carboxyl, or halo, e.g., $C_1$-$C_3$ alkyl or $C_1$-$C_3$ alkyl substituted with hydroxyl, carboxyl, or halo;
$R^6$ and $R^7$ are H;
$R^8$ is H; and
—O—PR is a sulfonate ester such as a tosylate ester, a mesylate ester, or the like.

Accordingly, $R^1$ can be $C_1$-$C_{12}$ hydrocarbyl, including $C_1$-$C_{10}$ hydrocarbyl, e.g., $C_1$-$C_{10}$ alkyl, $C_2$-$C_{10}$ alkenyl, $C_2$-$C_{10}$ alkynyl, and $C_5$-$C_{10}$ aryl, including cycloalkyl, branched alkyl, cycloalkenyl, branched cycloalkenyl, etc., any of which is optionally substituted, e.g., substituted with zero to 3 functional groups typically selected from hydroxyl, halo, carboxyl, $C_2$-$C_6$ acyloxy, $C_2$-$C_6$ alkoxycarbonyl, $C_2$-$C_6$ alkylamido, and combinations thereof, and containing zero to 3 heteroatoms such as 0, S. or N (including NH, NR where is $C_1$-$C_{12}$ hydrocarbyl, and N-heterocycles such as pyrrole, pyrrolidine, pyridine, imidazole, pyrazole, pyrazolidine, pyrazine, piperidine, azetidine, etc.).

As explained previously with regard to compound (AA), $R^2$ may be any of the groups and substituents identified above with respect to $R^1$, and may, in addition, be a functional group selected from those set forth in part (I) of this Detailed Description. Examples of functional groups that may serve as $R^2$ substituents thus include, without limitation, halo, carboxyl, $C_1$-$C_{12}$ alkoxy, $C_1$-$C_{12}$ alkylsulfanyl, $C_2$-$C_{12}$: acyl, $C_2$-$C_{12}$: acyloxy, $C_2$-$C_{12}$ alkoxycarbonyl, and $C_6$-$C_{18}$ aryloxycarbonyl (—(CO)—O-aryl).

E. Modifications to the Reaction Product:

Following completion synthesis as described in Parts A, B, C, or D, the reaction product may be modified to provide desired analogs of the compound obtained, e.g., by: hydrogenation of the isopropenyl substituent to an isopropyl group (see, e.g., Ben-Shabat et al. (2005) *J. Med. Chem.* 49:1113-17), a substitution reaction at the double bond of the isopropenyl group to provide a substituted alkyl group at that location; reaction of the free hydroxyl groups on the phenyl ring of the CBD structure to provide ether or ester substituents or the like; conversion to a tricyclic compound by effecting linkage between the isopropenyl group and the closest hydroxyl group on the phenyl ring; aromatization of the menthadienol ring; hydrogenation of the menthadienol ring to a cyclohexyl moiety, or a combination of two or more of the foregoing.

IV. Cannabinoid Analogs

It will be appreciated that the synthetic methods of Section III are useful to produce a variety of cannabinoids and analogs thereof, including naturally occurring analogs as well as semi-synthetic or synthetic analogs that are not found in nature. The invention, in another embodiment, also provides cannabinoid analogs having novel molecular structures and thus represent new compositions of matter, as discussed infra in Part B of this section.

A. Naturally Occurring or Other Known CBD Analogs:

Table 1 illustrates various CBD analogs that may be prepared using the methods of Section III, using different $R^1$-M reactants to produce variants at the 4' position of the CBD molecule:

TABLE 1

| $R^1$ | Compound |
|---|---|
| Methyl | 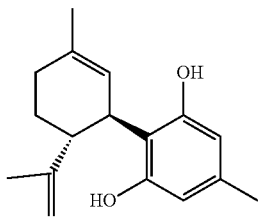<br>Cannabidiorcol (CBD-C1) |
| n-Propyl | 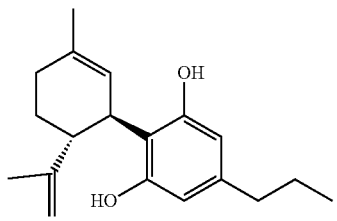<br>Cannabidivarin (CBDV) |
| n-Butyl | 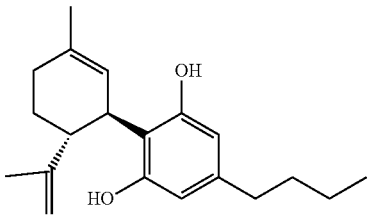<br>Nor-cannabidiol (CBD-C4) |
| N-Acetyl azetidine | 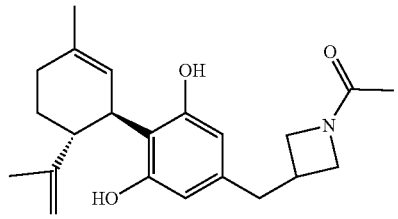 [SMILES: C=C(C)[C@@H]1CCC(C)=C[C@H]1c1c(O)cc(CC2CN(C(C)=O)C2)cc1O] |
| 4-Hydroxybutyl | 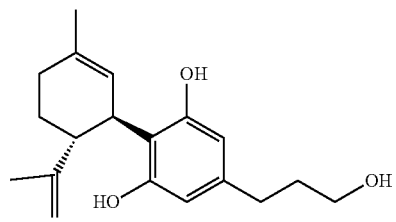 [SMILES: C=C(C)[C@@H]1CCC(C)=C[C@H]1c1c(O)cc(CCCO)cc1O] |

TABLE 1-continued

| $R^1$ | Compound |
|---|---|
| Carboxyethyl | 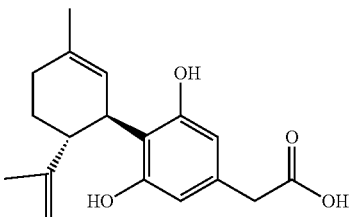 [SMILES: C=C(C)[C@@H]1CCC(C)=C[C@H]1c1c(O)cc(CC(=O)O)cc1O] |
| 3-Carboxypropyl | 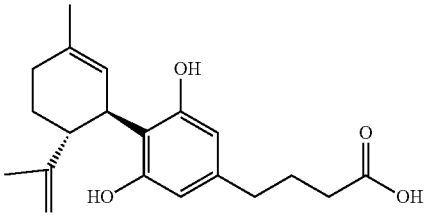 [SMILES: C=C(C)[C@@H]1CCC(C)=C[C@H]1c1c(O)cc(CCCC(=O)O)cc1O] |
| 2-(1H-1,2,3-Triazolyl)ethyl | 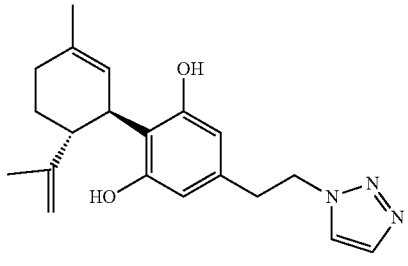 [SMILES: C=C(C)[C@@H]1CCC(C)=C[C@H]1c1c(O)cc(CCn2ccnn2)cc1O] |
| 2-Morpholino-ethyl | 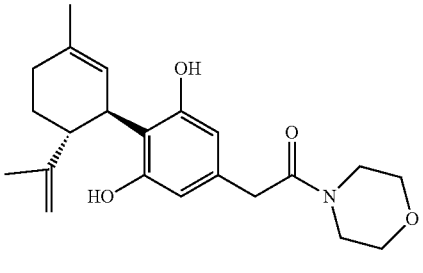 [SMILES: C=C(C)[C@@H]1CCC(C)=C[C@H]1c1c(O)cc(CC(=O)N2CCOCC2)cc1O] |
| 2-Ethoxyethyl | 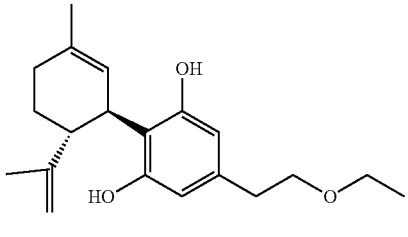 [SMILES: C=C(C)[C@@H]1CCC(C)=C[C@H]1c1c(O)cc(CCOCC)cc1O] |
| 1,2'-Dimethyl-heptyl | 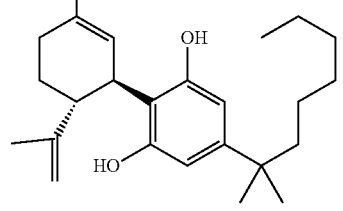<br>Dimethylheptyl CBD (DMH-CBD) ("Nabilone") |

See, e.g., Morales (2017), "An Overview on Medicinal Chemistry of Synthetic and Natural Derivatives of Cannabidiol," *Frontiers in Pharmacology* 8: 1-18; and Jung et al. (2019), supra.

The aforementioned list is by no means limited to the compounds in the table, but merely exemplifies several representative 4' analogs of CBD that can be prepared using the above syntheses.

Additional CBD analogs can be prepared using the present syntheses by selection of different $R^2$ groups when n is nonzero, optionally combined with selection of different $R^1$ moieties in the $R^1$-M reactant and/or different placement of the substituents on the phenyl ring.

For instance, when the reactant of formula (AA-1)

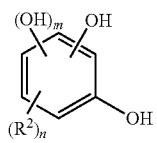

(AA-1)

is tetra-substituted with m equal to 1 and n equal to 1, and the ring is 1,3,5-trihydroxylated, the compound then has the structure of formula (CC-7)

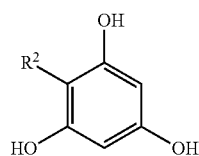

(CC-7)

Following reaction with (+)-menthadienol or analog thereof, hydroxyl protection as described earlier, cross-coupling with a co-reactant $R^1$-M, and deprotection, the reaction product has the structure of formula (CC-8)

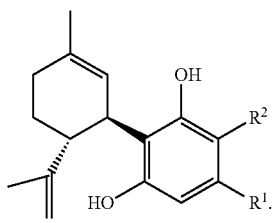

(CC-8)

Examples of analogs that can be prepared by selection of different $R^1$ moieties in $R^1$-M and varying m, n, and $R^2$ in the reactant (AA-1) are set forth in Table 2:

TABLE 2

| $R^1$ | $R^2$ | m, n | Compound |
|---|---|---|---|
| n-Pentyl | Carboxyl | m = 2, n = 1 | Cannabidiolic acid (CBDA) |
| n-Propyl | Carboxyl | m = 2, n = 1 | Cannabidivarinic acid (CBDVA-C3) |
| n-Pentyl | F | m = 2, n = 1 | |
| n-Pentyl | Cl | m = 2, n = 1 | |
| n-Pentyl | Br | m = 2, n = 1 | |
| N-Pentyl | Cl | m = 2, n = 2 | |

TABLE 2-continued

| R¹ | R² | m, n | Compound |
|---|---|---|---|
| N-Pentyl | Br | m = 2<br>n = 2 |  |

TABLE 2-continued

| R¹ | R² | m, n | Compound |
|---|---|---|---|
| N-Pentyl | n-Butoxy | m = 1<br>n = 2 | 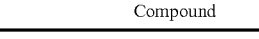 |

Examples of another group of analogs, wherein $R^2$ is substituted or unsubstituted alkoxycarbonyl of the form —(CO)—O—$R^{10}$, are set forth in Table 3.

TABLE 3

| R¹ | R¹⁰ | Compound |
|---|---|---|
| n-Pentyl | 2-Hydroxyethyl | |
| n-Pentyl | 2-Hydroxypentyl | |
| n-Pentyl | 2,3-Dihydoxypropyl | |
| N-Pentyl | Cyclohexyl | |
| N-Pentyl | N-Hexyl | |
| N-Pentyl | 2-(Methylsulfonamido)ethyl | |
| N-Propyl | 2-Hydroxyethyl | |

TABLE 3-continued

| R¹ | R¹⁰ | Compound |
|---|---|---|
| N-Propyl | Cyclohexyl | (structure) |
| N-Propyl | N-Hexyl | (structure) |

See, e.g., Götz et al. (2019), "Structure-Effect Relationships of Novel Semi-Synthetic Cannabinoid Derivatives," *Frontiers in Pharmacology* 10: 1284.

Other CBD analogs that can be prepared using the present synthetic methods include, without limitation, analogs that have modified hydroxyl groups such as alkoxy groups, or in some cases acyloxy groups, a conversion that can be carried out prior to or after reaction of (+)-menthadienol or (+)-menthadienol analog (BA-4) or (CC-3) with phloroglucinol or phloroglucinol analog (AA-1) (for examples of such compounds, see Haj et al. (2015) *J. Pharmacol. Exper. Ther.* 355: 66-75, e.g., compounds HU-444 and HU-445; and Jung et al. (2019) *Chem. Asian J.* 14: 3749-62, cited previously); analogs having a carboxyl or ester group at the 1-position, which can be introduced by using an appropriately substituted (+)-menthadienol analog (BA-4) or (CC-3) (Haj et al. (2015); analogs such as H$_2$CBD, having an isopropyl group instead of an isopropenyl substituent at the 4-position, which again can be accomplished by using a modified (+)-menthadienol analog as a reactant, i.e., a compound having a 4-isopropyl substituent (ibid.); analogs having a substituted alkyl group such as hydroxyethyl or hydroxypropyl instead of an isopropenyl group at the 4-position, which can be accomplished in the same way, by using a modified (+)-menthadienol analog as a reactant; other analogs classified by Jung et al. (2019) as "limonene-moiety modified analogs"; aryl-oxidized compounds, also as described in Jung et al. (2019); analogs in which the (+)-menthadienol ring is hydrogenated, as in H$_4$CBD; Jung et al.'s "double-modified" or multiply modified analogs, having two or more types of modifications relative to CBD per se; and analogs having alkenyl groups than are larger than the isopropenyl group of CBD (ibid., citing Kobayashi et al. (2006) *Org. Lett.* 8: 2699-702, William et al. (2002) *J. Org. Chem.* 67: 8771-82, and William et al. (2001) *Org. Lett.* 3: 2017-20). The foregoing list is not intended to be complete but rather illustrative of representative CBD analogs that can be prepared using the present methods.

As noted above, the compound or compounds ultimately synthesized may be further modified, if desired, to produce an additional type of analog, e.g., partial hydrogenation of a reaction product to convert the isopropenyl group of the (+)-menthadienol ring to an isopropyl group, or full hydrogenation to additionally convert the (+)-menthadienol ring to a cyclohexyl group.

The present method can, accordingly, be used to make not only CBD but also naturally occurring CBD analogs as well as known and unknown synthetic analogs, including metabolites, prodrugs, salts, esters, crystalline forms, stereoisomers, and the like. These analogs include, without limitation, Cannabichromanone (CBCN),
Cannabichromanone-C$_3$ (CBCN—C$_3$),
Cannabichromene (CBC),
Cannabichromenic acid (CBCA),
Cannabichromevarin (CBCV),
Cannabichromevarinic acid (CBCVA)
Cannabicitran (CBTC),
Cannabicoumaronone (CBCON),
Cannabicyclol (CBL),
Cannabicyclolic acid (CBLA),
Cannabicyclovarin (CBLV),
Cannabidiol monomethyl ether (CBDM)
Cannabidiol dimethyl ether (CBDD),
Cannabidiol dimethyl heptyl (CBD-DMH),
Cannabidiol dimethyl heptyl-7-oic acid (HU-320),
Dimethyl heptylpentyl cannabidiol (DMHP-CBD),
Cannabidiolic acid (CBDA),
Cannabidiorcol (CBD-C$_1$),
Cannabidiphorol (CBDP),
Cannabidivarin (CBDV),
Cannabidivarinic acid (CBDVA)
Cannabielsoin (CBE),
Cannabielsoic acid A (CBEA-C$_5$ A),
Cannabielsoic acid B (CBEA-O$_5$ B)
Cannabifuran (CBF),
Cannabigerocin (CBGO),
Cannabigerol (CBG);
Cannabigerol monomethyl ether (CBGM),
Cannabigerolic acid A (CBGA),
Cannabigerolic acid A monomethyl ether (CBGAM-C$_5$A),
Cannabigerorcin (CBGO);
Cannabigerovarin (CBGV),
Cannabigerovarinic acid (CBGVA),
Cannabiglendol-C$_3$,
Cannabimovone (CBM),
Cannabinidiol (CBND),
Cannabinodiol (CBND-C$_5$),
Cannabinodivarin (CBV)
Cannabinol (CBN),
Cannabinolic acid (CBNA),
Cannabinol methyl ether (CBNM),
Cannabiorcol (CBN—C$_1$), Cannabioxepane (CBX),
Cannabiripsol (CBR),
Cannabitetrol (CBTT),
Cannabitriol (CBT),
Cannabitriol-C$_3$ (CBT-C$_3$),
Cannabivarichromene,
Cannabivarin (CBV),
7-Carboxyl-CBD,
Dehydrocannabifuran (DCBF),
8,9-Dihydrocannabidiol (H2CBD) and H4CBD,
10-O-Ethyl-cannabitriol,
7-Hydroxyl-CBD,
Isotetrahydrocannabinol,
Isotetrahydrocannabivarin, and
Tetrahydrocannabivarin (THCV).

B. New Cannabinoids:

In another embodiment, the invention provides new cannabinoids, including, without limitation, analogs of CBD, analogs of CBN, analogs of CBC, and analogs of THCV. The analogs can be synthesized using any of the methods described in Section III, or other methods as will be described infra. The new compounds share not only certain aspects of molecular structure with known and/or naturally occurring cannabinoids, but also pharmacological properties and uses.

The novel analogs include CBD analogs having the structure of formula (EE)

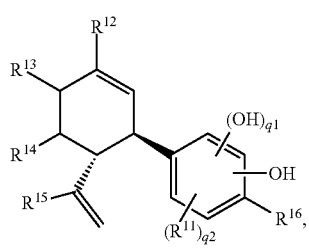

CBN analogs having the structure of formula (FF)

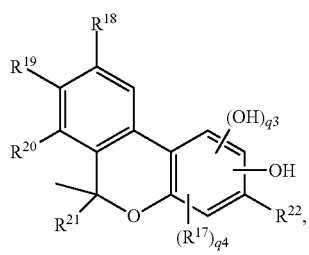

CBC analogs having the structure of formula (GG)

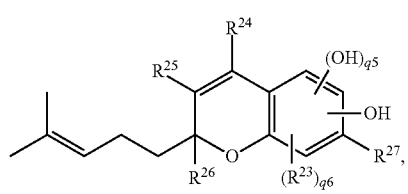

and THCV analogs having the structure of formula (HH)

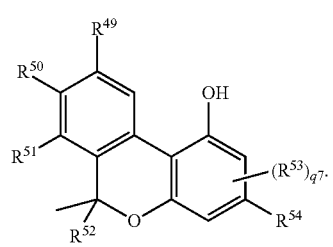

In the CBD analogs having the structure of formula (EE), q1 is zero or 1, q2 is zero, 1 or 2, and the substituents are as follows:

R$^{11}$ is selected from C$_1$-C$_{12}$ hydrocarbyl, substituted C$_1$-C$_{12}$ hydrocarbyl, heteroatom-containing C$_1$-C$_{12}$ hydrocarbyl, substituted heteroatom-containing C$_1$-C$_{12}$ hydrocarbyl, and functional groups (e.g., halo, carboxyl, C$_1$-C$_{12}$ alkoxy, C$_1$-C$_{12}$ alkylsulfanyl, C$_2$-C$_{12}$ acyl, C$_2$-C$_{12}$ acyloxy, C$_2$-C$_{12}$ alkoxycarbonyl, and C$_6$-C$_{18}$ aryloxycarbonyl (—(CO)—O-aryl)), and wherein when n is 2, the R$^{11}$ may be the same or different and any two R$^{11}$ bound to adjacent carbon atoms may be taken together to form a cyclic structure selected from a five-membered ring and a six-membered ring, optionally fused to an additional five-membered or six-membered ring, wherein the rings are aromatic, alicyclic, heteroaromatic, or heteroalicyclic, and have zero to 4 non-hydrogen substituents and zero to 3 heteroatoms;

R$^{12}$ is H, carboxyl, C$_2$-C$_6$ acyloxy, C$_2$-C$_6$ alkoxycarbonyl, C$_1$-C$_6$ alkyl, or C$_1$-C$_6$ alkyl substituted with hydroxyl, carboxyl, or halo;

R$^{13}$ and R$^{14}$ are independently selected from H, C$_1$-C$_{12}$ hydrocarbyl, substituted C$_1$-C$_{12}$ hydrocarbyl, heteroatom-containing C$_1$-C$_{12}$ hydrocarbyl, substituted heteroatom-containing C$_1$-C$_{12}$ hydrocarbyl, and functional groups;

R$^{15}$ is methyl, hydroxymethyl, or halomethyl; and

R$^{16}$ is C$_1$-C$_{18}$ alkyl, C$_2$-C$_{18}$ alkenyl, or C$_2$-C$_{18}$ alkynyl, substituted with (a) —(CO)—NR$^{28}$—R$^{29}$ wherein R$^{28}$ is H or C$_1$-C$_{12}$ hydrocarbyl and R$^{29}$ is C$_1$-C$_{12}$ hydrocarbyl, (b) —NR$^{30}$—R$^{31}$ wherein R$^{30}$ is H or C$_1$-C$_{12}$ hydrocarbyl and R$^{31}$ is C$_6$-C$_{12}$ hydrocarbyl, C$_1$-C$_{12}$ hydrocarbyl substituted with at least one functional group, C$_1$-C$_{12}$ heterohydrocarbyl, or C$_1$-C$_{12}$ heterohydrocarbyl substituted with at least one functional group, (c) —(SO$_2$)—R$^{32}$ wherein R$^{32}$ is H or C$_1$-C$_{12}$ heterohydrocarbyl, C$_1$-C$_{12}$ hydrocarbyl substituted with at least one functional group, or C$_1$-C$_{12}$ heterohydrocarbyl substituted with at least one functional group, (d) —(SO$_2$)—NR$^{33}$R$^{34}$ wherein R$^{33}$ is H or C$_1$-C$_{12}$ hydrocarbyl and R$^{34}$ is H or C$_1$-C$_{12}$ hydrocarbyl,

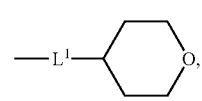

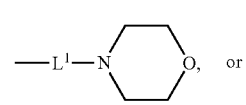

-continued

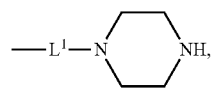
(g)

wherein $L^1$ is $C_1$-$C_6$ alkyl, or wherein $R^{16}$ is $C_1$-$C_{12}$ hydrocarbyloxy substituted with $C_1$-$C_{12}$ hydrocarbyloxy, wherein "hydrocarbyl," as noted in Section I, refers to unsubstituted hydrocarbyl, substituted hydrocarbyl, and/or heteroatom-containing hydrocarbyl.

In one embodiment, q1 is 1, q2 is zero, and the two hydroxyl groups are located meta to $R^{16}$.

In another embodiment, q1 is 1, q2 is zero, and the two hydroxyl groups are located meta to $R^{16}$, $R^{12}$ and $R^{15}$ are $C_1$-$C_6$ alkyl, e.g., methyl, $R^{13}$ and $R^{14}$ are H, and $R^{16}$ is $C_1$-$C_{12}$ alkyl or $C_2$-$C_{12}$ alkyl substituted with:

(a) —(CO)—$NR^{28}$—$R^{29}$ wherein $R^{28}$ is H or $C_1$-$C_8$ alkyl and $R^{29}$ is $C_1$-$C_8$ alkyl;

(b) —$NR^{30}R^{31}$ wherein $R^{30}$ is H or $C_1$-$C_8$ alkyl and $R^{31}$ is $C_6$-$C_{12}$ alkyl, $C_1$-$C_8$ alkyl substituted with at least one functional group, $C_1$-$C_8$ heteroalkyl, or $C_1$-$C_8$ heteroalkyl substituted with at least one functional group;

(c) —($SO_2$)—$R^{32}$ wherein $R^{32}$ is $C_1$-$C_8$ heteroalkyl, $C_1$-$C_8$ alkyl substituted with at least one functional group, or $C_1$-$C_8$ heteroalkyl substituted with at least one functional group;

(d) —($SO_2$)—$NR^{33}R^{34}$ wherein $R^{33}$ is H or $C_1$-$C_8$ alkyl and $R^{34}$ is H or $C_1$-8 alkyl, wherein the $C_1$-$C_8$ alkyl groups are either substituted or unsubstituted;

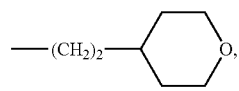
(e)

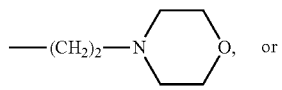
(f)

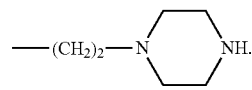
(g)

When $R^{12}$ and $R^{15}$ are methyl, the compound of formula (EE) is a CBD analog having the structure of formula (EE-1)

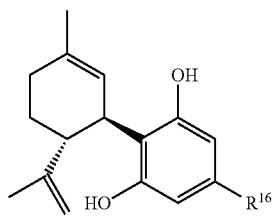
(EE-1)

wherein $R^{16}$ is as defined above.

In the CBN analogs having the structure of formula (FF),

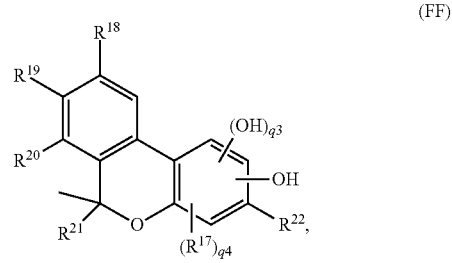
(FF)

q3 is zero or 1, q4 is zero, 1 or 2, and the substituents are as follows:

$R^{17}$ is selected from $C_1$-$C_{12}$ hydrocarbyl, substituted $C_1$-$C_{12}$ hydrocarbyl, heteroatom-containing $C_1$-$C_{12}$ hydrocarbyl, substituted heteroatom-containing $C_1$-$C_{12}$ hydrocarbyl, and functional groups (e.g., halo, carboxyl, $C_1$-$C_{12}$ alkoxy, $C_1$-$C_{12}$ alkylsulfanyl, $C_2$-$C_{12}$ acyl, $C_2$-$C_{12}$ acyloxy, $C_2$-$C_{12}$ alkoxycarbonyl, and $C_6$-$C_{18}$ aryloxycarbonyl (—(CO)—O-aryl)), and wherein when n is 2, the $R^{17}$ may be the same or different and any two $R^{17}$ bound to adjacent carbon atoms may be taken together to form a cyclic structure selected from a five-membered ring and a six-membered ring, optionally fused to an additional five-membered or six-membered ring, wherein the rings are aromatic, alicyclic, heteroaromatic, or heteroalicyclic, and have zero to 4 non-hydrogen substituents and zero to 3 heteroatoms;

$R^{18}$ is H, carboxyl, $C_2$-$C_6$ acyloxy, $C_2$-$C_6$ alkoxycarbonyl, $C_1$-$C_6$ alkyl, or $C_1$-$C_6$ alkyl substituted with hydroxyl, carboxyl, or halo;

$R^{19}$ and $R^{20}$ are independently selected from H, $C_1$-$C_{12}$ hydrocarbyl, substituted $C_1$-$C_{12}$ hydrocarbyl, heteroatom-containing $C_1$-$C_{12}$ hydrocarbyl, substituted heteroatom-containing $C_1$-$C_{12}$ hydrocarbyl, and functional groups;

$R^{21}$ is methyl, hydroxymethyl, or halomethyl; and $R^{22}$ is $C_1$-$C_{18}$ alkyl, $C_2$-$C_{18}$ alkenyl, or $C_2$-$C_{18}$ alkynyl, substituted with (a) —(CO)—$NR^{35}$—$R^{36}$ wherein $R^{35}$ is H or $C_1$-$C_{12}$ hydrocarbyl and $R^{36}$ is $C_1$-$C_{12}$ hydrocarbyl, (b) —$NR^{37}$—$R^{38}$ wherein $R^{37}$ is H or $C_1$-$C_{12}$ hydrocarbyl and $R^{38}$ is $C_6$-$C_{12}$ hydrocarbyl, $C_1$-$C_{12}$ hydrocarbyl substituted with at least one functional group, $C_1$-$C_{12}$ heterohydrocarbyl, or $C_1$-$C_{12}$ heterohydrocarbyl substituted with at least one functional group, (c) —($SO_2$)—$R^{39}$ wherein $R^{39}$ is H or $C_1$-$C_{12}$ heterohydrocarbyl, $C_1$-$C_{12}$ hydrocarbyl substituted with at least one functional group, or $C_1$-$C_{12}$ heterohydrocarbyl substituted with at least one functional group, (d) —($SO_2$)—$NR^{40}R^{41}$ wherein $R^{42}$ is H or $C_1$-$C_{12}$ hydrocarbyl and $R^{43}$ is H or $C_1$-$C_{12}$ hydrocarbyl,

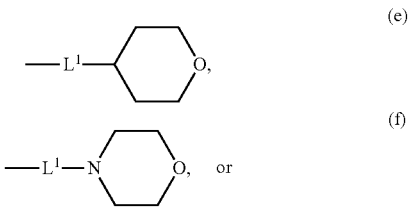
(e)

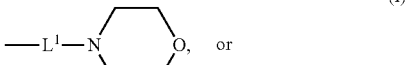
(f)

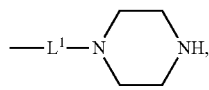
(g)

wherein $L^1$ is $C^1$-$C^6$ alkyl, or wherein $R^{22}$ is $C_1$-$C_{12}$ hydrocarbyloxy substituted with $C_1$-$C_{12}$ hydrocarbyloxy, wherein "hydrocarbyl," as noted in Section I, refers to unsubstituted hydrocarbyl, substituted hydrocarbyl, and/or heteroatom-containing hydrocarbyl.

In one embodiment, q3 and q4 are zero, and the hydroxyl group is located meta to $R^{22}$, $R^{18}$ and $R^{21}$ are $C_1$-$C_6$ alkyl, e.g., methyl, $R^{19}$ and $R^{20}$ are H, and $R^{22}$ is $C_1$-$C_{12}$ alkyl or $C_2$-$C_{12}$ alkenyl substituted with:

(a) —(CO)—$NR^{35}R^{36}$ wherein $R^{35}$ is H or $C_1$-$C_8$ alkyl and $R^{36}$ is $C_1$-$C_8$ alkyl;

(b) —$NR^{37}R^{38}$ wherein $R^{37}$ is H or $C_1$-$C_8$ alkyl and $R^{38}$ is $C_6$-$C_{12}$ alkyl, $C_1$-$C_8$ alkyl substituted with at least one functional group, $C_1$-$C_8$ heteroalkyl, or $C_1$-$C_8$ heteroalkyl substituted with at least one functional group;

(c) —($SO_2$)—$R^{39}$ wherein $R^{39}$ is $C_1$-$C_8$ heteroalkyl, $C_1$-$C_8$ alkyl substituted with at least one functional group, or $C_1$-$C_8$ heteroalkyl substituted with at least one functional group;

(d) —($SO_2$)—$NR^{40}R^{41}$ wherein $R^{40}$ is H or $C_1$-$C_8$ alkyl and $R^{41}$ is H or $C_1$-$C_8$ alkyl, wherein the $C_1$-$C_8$ alkyl groups are either substituted or unsubstituted;

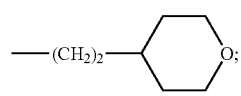
(e)

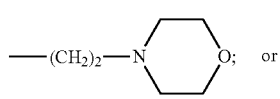
(f)

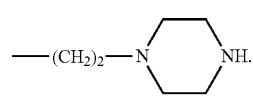
(g)

In this embodiment, when $R^{18}$ and $R^{21}$ are methyl, the compound of formula (FF) is a CBN analog having the structure of formula (FF-1)

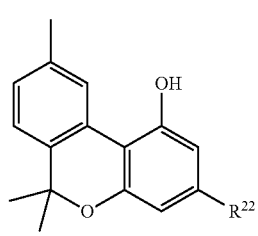
(FF-1)

wherein $R^{22}$ is as defined above.

In the CBC analogs having the structure of formula (GG), the reactant (AA), again, can be appropriately substituted to generate desired CBC analogs. In (GG),

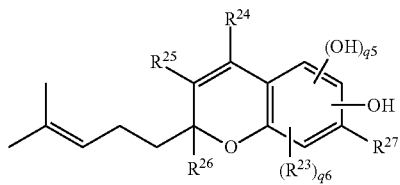
(GG)

q5 is zero or 1, q6 is zero, 1, or 2, the sum of q5 and q6 does not exceed 2, and the substituents are as follows:

$R^{23}$ is selected from $C_1$-$C_{12}$ hydrocarbyl, substituted $C_1$-$C_{12}$ hydrocarbyl, heteroatom-containing $C_1$-$C_{12}$ hydrocarbyl, substituted heteroatom-containing $C_1$-$C_{12}$ hydrocarbyl, and functional groups (e.g., halo, carboxyl, $C_1$-$C_{12}$ alkoxy, $C_1$-$C_{12}$ alkylsulfanyl, $C_2$-$C_{12}$ acyl, $C_2$-$C_{12}$ acyloxy, $C_2$-$C_{12}$ alkoxycarbonyl, and $C_6$-$C_{18}$ aryloxycarbonyl (—(CO)—O-aryl)), and wherein when n is 2, the $R^{23}$ may be the same or different and any two $R^{23}$ bound to adjacent carbon atoms may be taken together to form a cyclic structure selected from a five-membered ring and a six-membered ring, optionally fused to an additional five-membered or six-membered ring, wherein the rings are aromatic, alicyclic, heteroaromatic, or heteroalicyclic, and have zero to 4 n3on-hydrogen substituents and zero to 3 heteroatoms;

$R^{24}$ is H, $C_1$-$C_6$ alkyl, or $C_1$-$C_6$ alkyl substituted with hydroxyl, carboxyl, or halo;

$R^{25}$ is H, $C_1$-$C_{12}$ hydrocarbyl, substituted $C_1$-$C_{12}$ hydrocarbyl, heteroatom-containing $C_1$-$C_{12}$ hydrocarbyl, substituted heteroatom-containing $C_1$-$C_{12}$ hydrocarbyl, or a functional group;

$R^{26}$ is methyl, hydroxymethyl, or halomethyl; and $R^{27}$ is $C_1$-$C_{18}$ alkyl or $C_2$-$C_{18}$ alkenyl substituted with (a) —(CO)—$NR^{42}R^{43}$ wherein $R^{42}$ is H or $C_1$-$C_{12}$ hydrocarbyl and $R^{43}$ is $C_1$-$C_{12}$ hydrocarbyl, (b) —$NR^{44}R^{45}$ wherein $R^{39}$ is H or $C_1$-$C_{12}$ hydrocarbyl and $R^{45}$ is $C_6$-$C_{12}$ hydrocarbyl, $C_1$-$C_{12}$ hydrocarbyl substituted with at least one functional group, $C_1$-$C_{12}$ heterohydrocarbyl, or $C_1$-$C_{12}$ heterohydrocarbyl substituted with at least one functional group, (c) —($SO_2$)—$R^{46}$ wherein $R^{47}$ is H or $C_1$-$C_{12}$ heterohydrocarbyl, $C_1$-$C_{12}$ hydrocarbyl substituted with at least one functional group, or $C_1$-$C_{12}$ heterohydrocarbyl substituted with at least one functional group, (d), —($SO_2$)—$NR^{47}R^{48}$ wherein $R^{39}$ is H or $C_1$-$C_{12}$ hydrocarbyl and $R^{48}$ is H or $C_1$-$C_{12}$ hydrocarbyl,

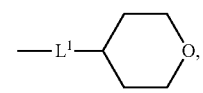
(e)

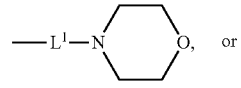
(f)

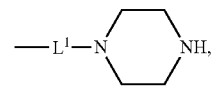
(g)

wherein $L^1$ is $C^1$-$C^6$ alkyl, or wherein $R^{27}$ is $C_1$-$C_{12}$ hydrocarbyloxy substituted with $C_1$-$C_{12}$ hydrocarbyloxy, wherein "hydrocarbyl," as before, refers to unsubstituted hydrocarbyl, substituted hydrocarbyl, and/or heteroatom-containing hydrocarbyl.

In one embodiment, q5 and q6 are zero and the remaining hydroxyl group is located meta to $R^{27}$, $R^{24}$ and $R^{25}$ are H, $R^{26}$ is $C_1$-$C_6$ alkyl, and $R^{27}$ is $C_2$-$C_{12}$ alkyl substituted with:
(a) —(CO)—$NR^{42}R^{43}$ wherein $R^{28}$ is H or $C_1$-$C_8$ alkyl and $R^{43}$ is $C_1$-$C_8$ alkyl;
(b) —$NR^{44}R^{45}$ wherein $R^{44}$ is H or $C_1$-$C_8$ alkyl and $R^{45}$ is $C_6$-$C_{12}$ alkyl, $C_1$-$C_8$ alkyl substituted with at least one functional group, $C_1$-$C_8$ heteroalkyl, or $C_1$-$C_8$ heteroalkyl substituted with at least one functional group;
(c) —$(SO_2)$—$R^{46}$ wherein $R^{46}$ is $C_1$-$C_8$ heteroalkyl, $C_1$-$C_8$ alkyl substituted with at least one functional group, or $C_1$-$C_8$ heteroalkyl substituted with at least one functional group;
(d) —$(SO_2)$—$NR^{47}R^{48}$ wherein $R^{47}$ is H or $C_1$-$C_8$ alkyl and $R^{48}$ is H or $C_1$-$C_8$ alkyl, wherein the $C_1$-$C_8$ alkyl groups are either substituted or unsubstituted;

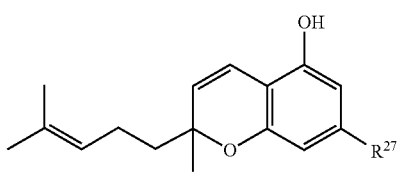

In the aforementioned embodiment, compound (GG) is a CBC analog having the structure of formula (GG-1) when $R^{26}$ is methyl:

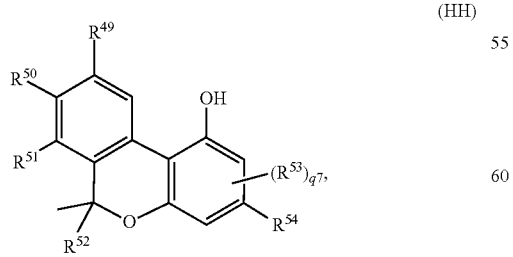

wherein $R^{27}$ is as defined above.

In the THCV analogs represented by the structure of formula (HH)

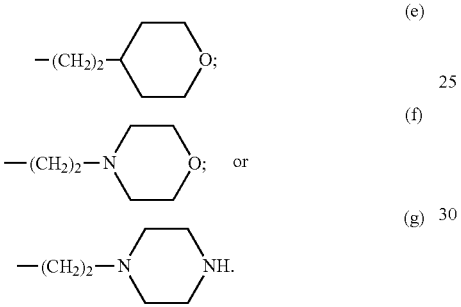

q7 is zero or 1, and the substituents are as follows:
$R^{53}$ is selected from $C_1$-$C_{12}$ hydrocarbyl, substituted $C_1$-$C_{12}$ hydrocarbyl, heteroatom-containing $C_1$-$C_{12}$ hydrocarbyl, substituted heteroatom-containing $C_1$-$C_{12}$ hydrocarbyl, and functional groups (e.g., halo, carboxyl, $C_1$-$C_{12}$ alkoxy, $C_1$-$C_{12}$ alkylsulfanyl, $C_2$-$C_{12}$ acyl, $C_2$-$C_{12}$ acyloxy, $C_2$-$C_{12}$ alkoxycarbonyl, and $C_6$-$C_{18}$ aryloxycarbonyl (—(CO)—O-aryl));
$R^{49}$ is H, carboxyl, $C_2$-$C_6$ acyloxy, $C_2$-$C_6$ alkoxycarbonyl, $C_1$-$C_6$ alkyl, or $C_1$-$C_6$ alkyl substituted with hydroxyl, carboxyl, or halo;
$R^{50}$ and $R^{51}$ are independently selected from H, $C_1$-$C_{12}$ hydrocarbyl, substituted $C_1$-$C_{12}$ hydrocarbyl, heteroatom-containing $C_1$-$C_{12}$ hydrocarbyl, substituted heteroatom-containing $C_1$-$C_{12}$ hydrocarbyl, and functional groups;
$R^{52}$ is methyl, hydroxymethyl, or halomethyl; and
$R^{54}$ is $C_1$-$C_{18}$ alkyl, $C_2$-$C_{18}$ alkenyl, or $C_2$-$C_{18}$ alkynyl, substituted with (a) —(CO)—$NR^{55}R^{56}$ wherein $R^{55}$ is H or $C_1$-$C_{12}$ hydrocarbyl and $R^{56}$ is $C_1$-$C_{12}$ hydrocarbyl, (b) —$NR^{57}R^{58}$ wherein $R^{57}$ is H or $C_1$-$C_{12}$ hydrocarbyl and $R^{58}$ is $C_6$-$C_{12}$ hydrocarbyl, $C_1$-$C_{12}$ hydrocarbyl substituted with at least one functional group, $C_1$-$C_{12}$ heterohydrocarbyl, or $C_1$-$C_{12}$ heterohydrocarbyl substituted with at least one functional group, (c) —$(SO_2)$—$R^{59}$ wherein $R^{59}$ is H or $C_1$-$C_{12}$ heterohydrocarbyl, $C_1$-$C_{12}$ hydrocarbyl substituted with at least one functional group, or $C_1$-$C_{12}$ heterohydrocarbyl substituted with at least one functional group, (d) —$(SO_2)$—$NR^{60}R^{61}$ wherein $R^{60}$ is H or $C_1$-$C_{12}$ hydrocarbyl and $R^{61}$ is H or $C_1$-$C_{12}$ hydrocarbyl,

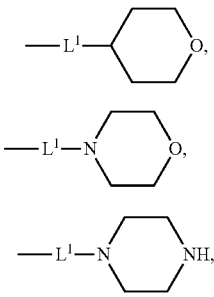

wherein $L^1$ is $C_1$-$C_6$ alkyl, or wherein $R^{16}$ is $C_1$-$C_{12}$ hydrocarbyloxy substituted with $C_1$-$C_{12}$ hydrocarbyloxy.

In one embodiment, q7 is zero, $R^{49}$ and $R^{52}$ are methyl, and $R^{50}$ and $R^{51}$ are H, so that the THCV analog having the structure (HH) is (HH-1)

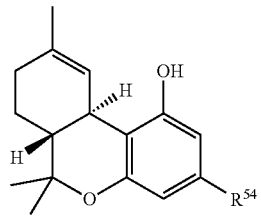

wherein $R^{54}$ is $C_1$-$C_{12}$ alkyl or $C_2$-$C_{12}$ alkenyl (preferably $C_1$-$C_3$ alkyl) substituted with:
(a) —(CO)—$NR^{55}R^{56}$ wherein $R^{55}$ is H or $C_1$-$C_8$ alkyl and $R^{56}$ is $C_1$-$C_8$ alkyl;
(b) —$NR^{57}R^{58}$ wherein $R^{57}$ is H or $C_1$-$C_8$ alkyl and $R^{58}$ is $C_6$-$C_{12}$ alkyl, $C_1$-$C_8$ alkyl substituted with at least one functional group, $C_1$-$C_8$ heteroalkyl, or $C_1$-$C_8$ heteroalkyl substituted with at least one functional group;

(c) —$(SO_2)$—$R^{59}$ wherein $R^{32}$ $C_1$-$C_8$ heteroalkyl, $C_1$-$C_8$ alkyl substituted with at least one functional group, or $C_1$-$C_8$ heteroalkyl substituted with at least one functional group; or (d) —$(SO_2)$—$NR^{60}R^{61}$ wherein $R^{60}$ is H or $C_1$-$C_8$ alkyl and $R^{61}$ is H or $C_1$-$C_8$ alkyl, wherein the $C_1$-$C_8$ alkyl groups are either substituted or unsubstituted.

Examples of specific such CBD, CBN, CBC, and THCV analogs include, without limitation, compounds having the structures of formula (EE-1), (FF-1), (GG-1), and (HH-1) wherein $R^{16}$, $R^{22}$, $R^{27}$, and $R^{54}$ are selected from the following:

—(CO)—$NHCH_3$;
—(CO)—$NHCH_2CH_3$;
—(CO)—NH—$(CH_2)_2CH_3$;
—(CO)—NH—$(CH_2)_3CH_3$;
—(CO)—NH—$(CH_2)_4CH_3$;
—$(CH_2)$—(CO)—$NHCH_3$;
—$(CH_2)$—(CO)—$NHCH_2CH_3$;
—$(CH_2)$—(CO)—NH—$(CH_2)_2CH_3$;
—$(CH_2)$—(CO)—NH—$(CH_2)_3CH_3$;
—$(CH_2)$—(CO)—NH—$(CH_2)_4CH_3$;
—$(CH_2)_2$—(CO)—$NHCH_3$;
—$(CH_2)_2$—(CO)—$NHCH_2CH_3$;
—$(CH_2)_2$—(CO)—NH—$(CH_2)_2CH_3$;
—$(CH_2)_2$—(CO)—NH—$(CH_2)_3CH_3$;
—$(CH_2)_2$—(CO)—NH—$(CH_2)_4CH_3$;
—$(CH_2)_3$—(CO)—$NHCH_3$;
—$(CH_2)_3$—(CO)—$NHCH_2CH_3$;
—$(CH_2)_3$—(CO)—NH—$(CH_2)_2CH_3$;
—$(CH_2)_3$—(CO)—NH—$(CH_2)_3CH_3$;
—$(CH_2)_3$—(CO)—NH—$(CH_2)_3CH_3$
—$NHCH_3$;
—$NHCH_2CH_3$;
—NH—$(CH_2)_3CH_3$;
—NH—$(CH_2)_4CH_3$;
—$(CH_2)$—$NHCH_3$;
—$(CH_2)$—$NHCH_2CH_3$;
—$(CH_2)$—NH—$(CH_2)_2CH_3$;
—$(CH_2)$—NH—$(CH_2)_3CH_3$;
—$(CH_2)_2$—$NHCH_3$;
—$(CH_2)_2$—$NHCH_2CH_3$;
—$(CH_2)_2$—NH—$(CH_2)_2CH_3$;
—$(CH_2)_2$—NH—$(CH_2)_3CH_3$;
—$(CH_2)_3$—$NHCH_3$;
—$(CH_2)_3$—$NHCH_2CH_3$;
—$(CH_2)_3$—NH—$(CH_2)_2CH_3$;
—$(CH_2)_3$—NH—$(CH_2)_3CH_3$;
—$(CH_2)_3$—NH—$(CH_2)_4CH_3$;
—$(SO_2)$—$CH_3$;
—$(SO_2)$—$CH_2CH_3$;
—$(SO_2)$—$(CH_2)_3CH_3$;
—$(SO_2)$—$(CH_2)_4CH_3$;
—$(CH_2)$—$(SO_2)$—$CH_3$;
—$(CH_2)$—$(SO_2)$—$CH_2CH_3$;
—$(CH_2)$—$(SO)_2$—$(CH_2)_3CH_3$;
—$(CH_2)$—$(SO_2)$—$(CH_2)_4CH_3$;
—$(CH_2)_2$—$(SO_2)$—$CH_3$;
—$(CH_2)_2$—$(SO_2)$—$CH_2CH_3$;
—$(CH_2)_2$—$(SO_2)$—$(CH_2)_3CH_3$;
—$(CH_2)_2$—$(SO_2)$—$(CH_2)_4CH_3$;
—$(CH_2)_3$—$(SO_2)$—$CH_3$;
—$(CH_2)_3$—$(SO_2)$—$CH_2CH_3$;
—$(CH_2)_3$—$(SO_2)$—$(CH_2)_3CH_3$;
—$(CH_2)_3$—$(SO_2)$—$(CH_2)_4CH_3$;
—$(SO_2)$—$NHCH_3$;
—$(SO_2)$—NH—$CH_2CH_3$;
—$(SO_2)$—NH—$(CH_2)_3CH_3$;
—$(SO_2)$—NH—$(CH_2)_4CH_3$;
—$(CH_2)$—$(SO_2)$—NH—$CH_3$;
—$(CH_2)$—$(SO_2)$—NH—$CH_2CH_3$;
—$(CH_2)$—$(SO_2)$—NH—$(CH_2)_2CH_3$;
—$(CH_2)$—$(SO_2)$—NH—$(CH_2)_4CH_3$;
—$(CH_2)_2$—$(SO_2)$—NH—$CH_3$;
—$(CH_2)_2$—$(SO_2)$—NH—$CH_2CH_3$;
—$(CH_2)_2$—$(SO_2)$—NH—$(CH_2)_2CH_3$;
—$(CH_2)_2$—$(SO_2)$—NH—$(CH_2)_4CH_3$;
—$(CH_2)_3$—$(SO_2)$—NH—$CH_3$;
—$(CH_2)_3$—$(SO_2)$—NH—$CH_2CH_3$;
—$(CH_2)_3$—$(SO_2)$—NH—$(CH_2)_2CH_3$; and
—$(CH_2)_3$—$(SO_2)$—NH—$(CH_2)_4CH_3$.

Also of interest are cannabinoids having the aforementioned structures, i.e. any of the structures (EE), (EE-1), (FF), (FF-1), (GG), (GG-1), (HH), and (HH-1) wherein $R^{16}$, $R^{22}$, $R^{27}$, and $R^{54}$ are selected from the "representative $R^1$ substituents" defined and exemplified in Section (II) of this Detailed Description.

CBD analogs having the structure of formula (EE) can be synthesized using the methods described in Section III and/or in the Examples herein, or by implementing other synthetic methods that will be apparent to those of ordinary skill in the art from the present disclosure.

CBN analogs having the structure of formula (FF) are typically prepared from a starting material having the structure of formula (FF—P)

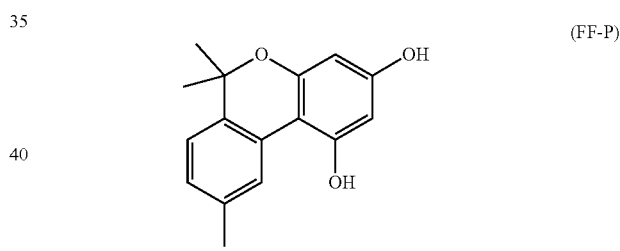

(FF-P)

which can be readily synthesized using the method of Rigby (1971) *J. Chem. Soc. Section C: Organic* (4):765-768. The starting material (FF—P) may be prepared in substituted form or substituted after synthesis, depending on the desired CBN analog. The CBN analogs herein can also be synthesized using the methods of Examples 24-27, optionally modified using techniques known to those of ordinary skill in the art and/or described in the literature.

Generally, CBC and CBC analogs having the structure (GG) may be synthesized according to either of the following reactions (a) or (b):

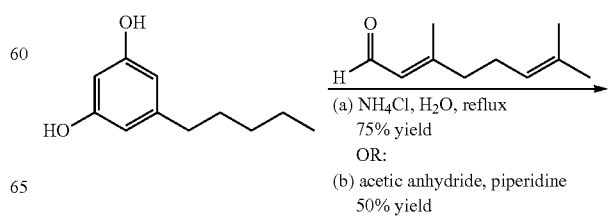

(a) $NH_4Cl$, $H_2O$, reflux
75% yield
OR:
(b) acetic anhydride, piperidine
50% yield -continued

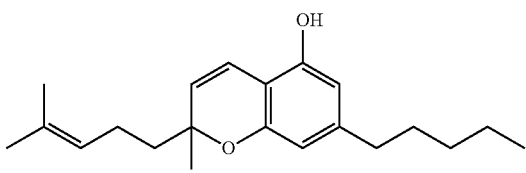

wherein CBC analogs can be provided as reaction products by starting with a suitably substituted olivetol analog, i.e., compound (AA). Also see Pollastro et al. (2018) *Nat. Prod. Comm.* 13(9): 1189-1194, which describes cannabichromene synthesis.

A representative synthesis of THCV that is readily adaptable to a method for preparing THCV analogs herein (again by selection of appropriately substituted phloroglucinol, which in turn reacts to give a suitably substituted divarinol intermediate) is described in Examples 3 and 21.

Additional cannabinoid compounds that can be synthesized using the present methods thus include, without limitation, the following:

CBD analogs:

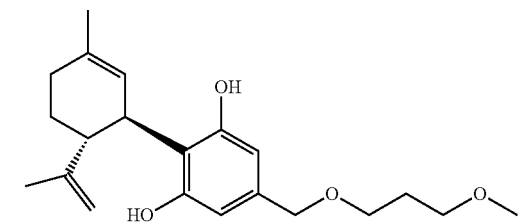

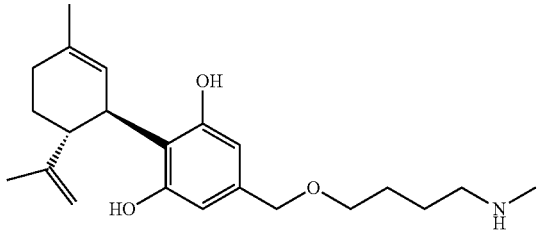

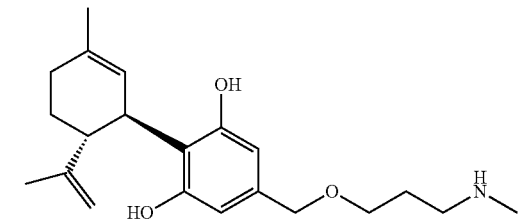

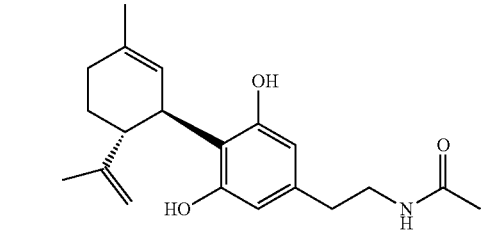

-continued

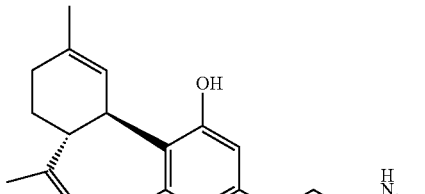

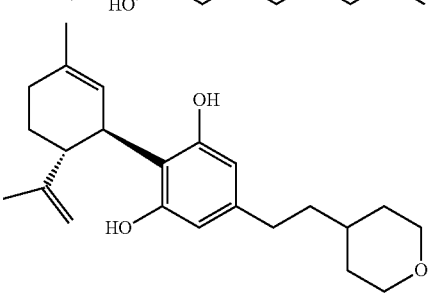

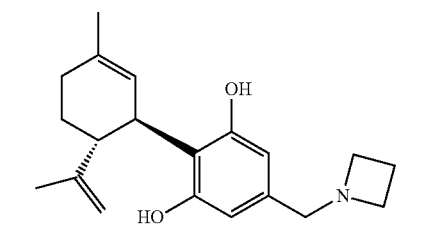

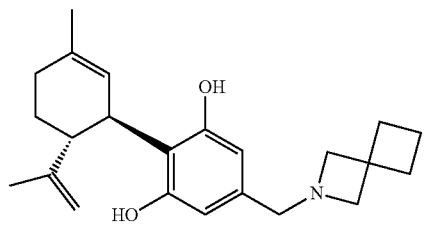

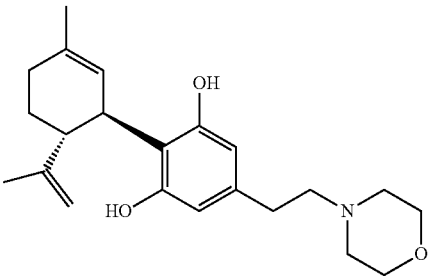

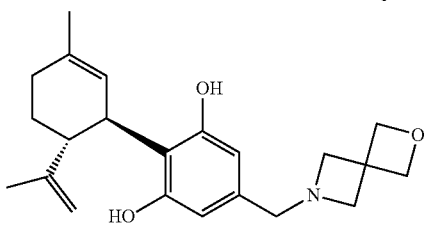

CBN analogs:

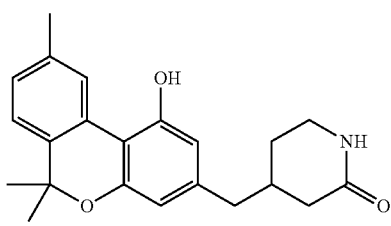

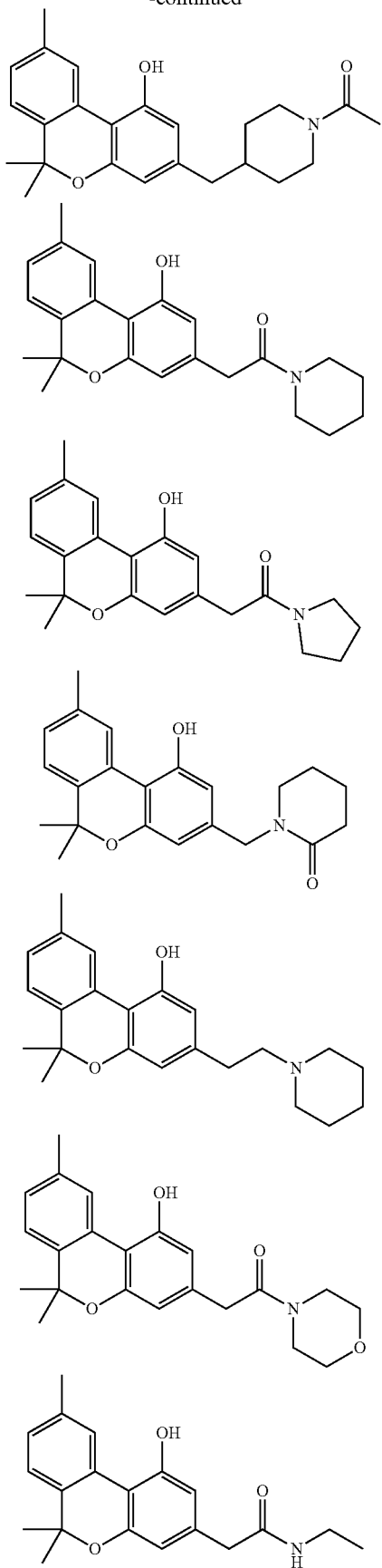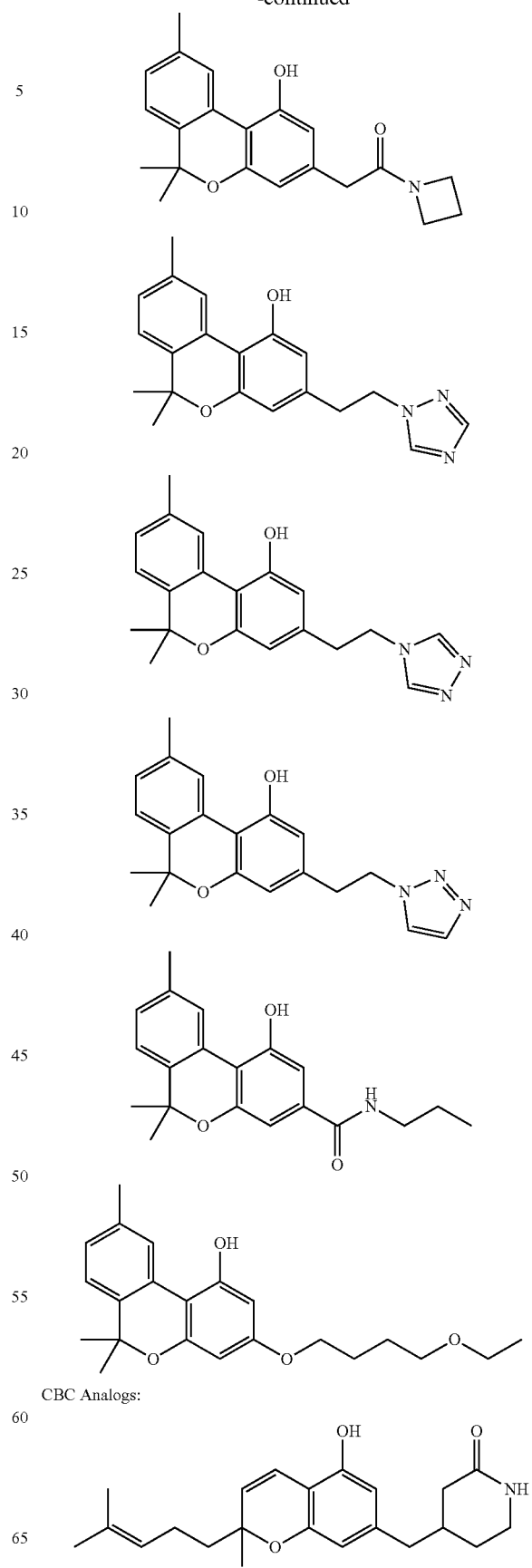
CBC Analogs:

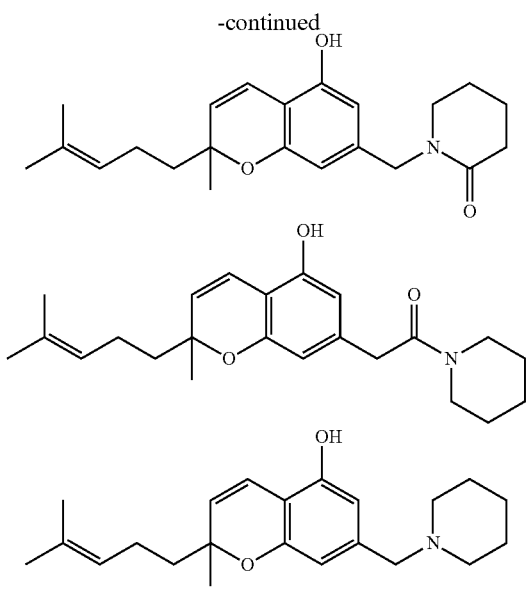

V. Pharmaceutical Formulations and Methods of Use

Pharmaceutical formulations suitable for administration of a cannabinoid synthesized as described herein are compositions wherein the cannabinoid, as a pharmacologically active agent, is contained in a "therapeutically effective" amount, i.e., in an amount effective to achieve its intended purpose. The cannabinoid may be in the form of a reaction product composition, but more typically it will be in isolated, purified form.

Determination of a therapeutically effective amount for any particular cannabinoid is within the capability of those skilled in the art. Generally, toxicity and therapeutic efficacy of a compound or composition described herein can be determined by standard pharmaceutical procedures in cell cultures or experimental animals, e.g., procedures used for determining the maximum tolerated dose (MTD), the ED50, which is the effective dose to achieve 50% of maximal response, and the therapeutic index (TI), which is the ratio of the MTD to the ED50. Compounds and compositions with high TIs are the more preferred compounds and compositions herein, and preferred dosage regimens are those that maintain plasma levels of the active agents at or above a minimum concentration to maintain the desired therapeutic effect. Dosage will, of course, also depend on a number of factors, including the particular compound or composition, the site of intended delivery, the route of administration, and other pertinent factors known to the prescribing physician.

Administration of a cannabinoid of the invention may be carried out using any appropriate mode of administration. Thus, administration can be, for example, oral, parenteral, transdermal, transmucosal (including rectal and vaginal), sublingual, by inhalation, or via an implanted reservoir in a dosage form. The term "parenteral" as used herein is intended to include subcutaneous, intravenous, and intramuscular injection. Depending on the intended mode of administration, the pharmaceutical formulation containing the cannabinoid may be a solid, semi-solid or liquid, such as, for example, a tablet, a capsule, a caplet, a liquid, a suspension, an emulsion, a suppository, granules, pellets, beads, a powder, or the like, preferably in unit dosage form suitable for single administration of a precise dosage. Suitable pharmaceutical compositions and dosage forms may be prepared using conventional methods known to those in the field of pharmaceutical formulation and described in the pertinent texts and literature, e.g., in Remington: The Science and Practice of Pharmacy (Easton, Pa.: Mack Publishing Co., 1995). For those compounds that are orally active, oral dosage forms are generally preferred, and include tablets, capsules, caplets, solutions, suspensions, and syrups, and may also comprise a plurality of granules, beads, powders, or pellets that may or may not be encapsulated. Preferred oral dosage forms are tablets and capsules.

Tablets may be manufactured using standard tablet processing procedures and equipment. Direct compression and granulation techniques are preferred. In addition to the active agent, tablets will generally contain inactive, pharmaceutically acceptable carrier materials such as binders, lubricants, disintegrants, fillers, stabilizers, surfactants, coloring agents, and the like.

Capsules are also preferred oral dosage forms for those cannabinoids that are orally active, in which case the cannabinoid-containing formulation may be encapsulated in the form of a liquid or solid (including particulates such as granules, beads, powders or pellets). Suitable capsules may be either hard or soft, and are generally made of gelatin, starch, or a cellulosic material, with gelatin capsules preferred. Two-piece hard gelatin capsules are preferably sealed, such as with gelatin bands or the like. See, for example, Remington: The Science and Practice of Pharmacy, cited supra, which describes materials and methods for preparing encapsulated pharmaceuticals.

Oral dosage forms, whether tablets, capsules, caplets, or particulates, may, if desired, be formulated so as to provide for gradual, sustained release of the cannabinoid over an extended time period. Generally, as will be appreciated by those of ordinary skill in the art, sustained release dosage forms are formulated by dispersing the cannabinoid within a matrix of a gradually hydrolyzable material such as a hydrophilic polymer, or by coating a solid, drug-containing dosage form with such a material. Hydrophilic polymers useful for providing a sustained release coating or matrix include, by way of example: cellulosic polymers such as hydroxypropyl cellulose, hydroxyethyl cellulose, hydroxypropyl methyl cellulose, methyl cellulose, ethyl cellulose, cellulose acetate, and carboxymethylcellulose sodium; acrylic acid polymers and copolymers, preferably formed from acrylic acid, methacrylic acid, acrylic acid alkyl esters, methacrylic acid alkyl esters, and the like, e.g. copolymers of acrylic acid, methacrylic acid, methyl acrylate, ethyl acrylate, methyl methacrylate and/or ethyl methacrylate; and vinyl polymers and copolymers such as polyvinyl pyrrolidone, polyvinyl acetate, and ethylene-vinyl acetate copolymer.

Preparations for parenteral administration of the cannabinoid include sterile aqueous and nonaqueous solutions, suspensions, and emulsions. Injectable aqueous solutions contain the cannabinoid in water-soluble form. Examples of nonaqueous solvents or vehicles include fatty oils, such as olive oil and corn oil, synthetic fatty acid esters, such as ethyl oleate or triglycerides, low molecular weight alcohols such as propylene glycol, synthetic hydrophilic polymers such as polyethylene glycol, liposomes, and the like. Parenteral formulations may also contain adjuvants such as solubilizers, preservatives, wetting agents, emulsifiers, dispersants, and stabilizers, and aqueous suspensions may contain substances that increase the viscosity of the suspension, such as sodium carboxymethyl cellulose, sorbitol, and dextran. Injectable formulations are rendered sterile by incorporation of a sterilizing agent, filtration through a bacteria-retaining filter, irradiation, or heat. They can also be manufactured using a sterile injectable medium. The active agent may also be in dried, e.g., lyophilized, form that may be rehydrated with a suitable vehicle immediately prior to administration via injection.

The cannabinoid may also be administered through the skin using conventional transdermal drug delivery systems, wherein the active agent is contained within a laminated structure that serves as a drug delivery device to be affixed to the skin. In such a structure, the drug composition is contained in a layer, or "reservoir," underlying an upper backing layer. The laminated structure may contain a single reservoir, or it may contain multiple reservoirs. In one embodiment, the reservoir comprises a polymeric matrix of a pharmaceutically acceptable contact adhesive material that serves to affix the system to the skin during drug delivery. Alternatively, the drug-containing reservoir and skin contact adhesive are present as separate and distinct layers, with the adhesive underlying the reservoir which, in this case, may be either a polymeric matrix as described above, or it may be a liquid or hydrogel reservoir, or may take some other form. Transdermal drug delivery systems may in addition contain a skin permeation enhancer.

In addition, the cannabinoid may be formulated in a depot preparation for controlled release of the active agent, preferably sustained release over an extended time period. These sustained release dosage forms are generally administered by implantation (e.g., subcutaneously or by intramuscular injection).

The cannabinoid can also be formulated for inhalation, e.g., as a solution in saline, as a dry powder, or as an aerosol. Administration may be via the intranasal route or via oral inhalation. A pharmaceutical formulation for delivery to the lungs via oral inhalation can also be a dry powder formulation, such as may comprise nanoparticle-sized solid particles containing the cannabinoid and suitable dry powder excipients, for example, lactose monohydrate, magnesium stearate, mannitol, or the like. Suitable dry powder composition components and inhaler types are described, inter alia, by de Boer (2017) Expert Opin Drug Deliv. 14(4): 499-512, and U.S. Patent Publication No. 2009/00004279 to Hofmann et al., both incorporated by reference herein.

Phytocannabinoids and structurally related exo-cannabinoids as a class have highly selective agonist and antagonist activity for the G protein-coupled receptors (GPCRs), CB(1) and CB(2), and individually may have activity at other receptors (such as the opiate mu- and kappa-receptors) that regulate a wide variety of metabolic and neurochemical processes. These receptors have been implicated in the progression of numerous diseases such as anorexia, emesis, pain, inflammation, multiple sclerosis, neurodegenerative disorders (Parkinson's disease, Huntington's disease, Tourette's syndrome, Alzheimer's disease), epilepsy, glaucoma, osteoporosis, schizophrenia, cardiovascular disorders, cancer, obesity, and metabolic syndrome-related disorders. For all of these, phytocannabinoids extracted from Hemp (*Cannabis sativa* L) have shown promise as potential therapies.

As such, the cannabinoids prepared using the present methods, including, but not limited to, CBD analogs, CBN analogs, CBC analogs, THCV, and THCV analogs, are compounds that, like CBD and other known cannabinoids, exhibit at least one of:

Neuroprotective effects in neurodegenerative disorders (see, e.g., Fernandez-Ruiz et al. (2013) *Br. J. Clin. Pharmacol.* 75: 323-33); Scuderi et al. (2014) *Phyther. Res.* 28: 1007-13; Ibeas Bih (2015) *Neurotherapeutics* 12: 699-730; Martin-Moreno et al. (2011) *Mol. Pharmacol.* 79(6): 964-73), regarding treatment of Alzheimer's disease);

Amelioration of the progressive degeneration of nigrostriatala dopaminergic neurons in Parkinson's disease (see Lastres-Becker et ala. (2005) *Neurobiol. Dis.* 19(1-2): 96-107);

Beneficial effects in cerebral ischemia (Braida et al. (2003) *Neurosci. Lett.* 345: 61-64);

Antiepileptic activity (see Devinsky et al. (2015) *Lancet Neural.* 15: 270-78; Wright et al. (2015) *Epilepsy Res.* 111: 111-113);

Antipsychotic activity (see Bhattacharyya et al. (2010) *Neuropsychopharmacology* 35: 764-74);

Anti-inflammatory activity (see Ruiz-Valdepeña et al. (2015) *Bioorgan. Med. Chem.* 23: 1377-85; and Burstein et al. (2015) *Bioorgan. Med. Chem.* 23: 1377-85);

Analgesic activity (see, e.g., Maione et al. (2015) *Br. J. Pharmacol.* 162: 584-96), either in reducing pain directly or by reducing the perception of pain;

Anti-asthmatic activity (see Ribeiro et al. (2015) *Immunopharmacol. Immunotoxicol.* 37: 35-41; and Vuolo et al. (2015) *Mediators Inflamm.* 2015:538670);

Anxiolytic activity;

Antitumor activity (see McAllister et al. (2011) Breast Cancer Res. Treat. 129: 37-47; and Massi et al. (2013) *Br. J. Clin. Pharmacol.* 75: 303-12);

Anti-arthritic activity (see, e.g., Lowin et al. (2020) *Cell Death Dis.* 11(8): 714);

Antipsychotic activity, including antischizophrenic activity (see Leweke (2016) *Front Pharmacol.* 7:422);

Anti-diabetic activity (see Weiss et al. (2008) *Neuropharmacology* 54(1): 244-249, regarding treatment of Type 1 diabetes);

Appetite suppression;

Glucose regulation; and

Efficacy in the treatment of post-traumatic stress disorder (PTSD).

Additional information pertaining to potential uses, regulatory approvals, and clinical trials of CBD may be found in Fasino et al. (2016) *Pharmacotherapy* 36: 781-96 and in White (2019) *J. Clin. Pharm.* 59(7): 923-34, the disclosures of which are incorporated by reference herein.

A therapeutic utility of particular interest is in the treatment of opioid withdrawal symptoms, wherein a cannabinoid of the invention is administered to an individual who has stopped opioid use or is in the process of reducing the regular dosage of an opioid.

Depending on the indication, a cannabinoid as described herein may be co-administered with at least one additional active agent, either simultaneously (in the same formulation or in different formulations) or separately. An additional active agent may have utility against the primary indication of interest. For instance, administration to treat inflammation may involve co-administration of the cannabinoid with a nonsteroidal anti-inflammatory agent (NSAID) or a steroidal anti-inflammatory agent. As another example, administration to treat pain may involve co-administration of the cannabinoid with an additional analgesic agent, e.g., an opioid analgesic or a non-opioid analgesic.

Co-administration of a cannabinoid as provided herein with an opioid analgesic agent is of interest insofar as a combination formulation, or separate co-administration, will reduce the therapeutic dosage of the opioid required and eliminate or at least minimize many of the undesirable side effects associated with opioid use, such as sedation, dizziness, tolerance, physical dependence, and the like. See Nielsen et al. (2017), "Opioid-Sparing Effect of Cannabinoids" A Systematic Review and Meta-Analysis," *Neuropsychopharmacology* 42(9): 1752-1765, which indicates that the median effective dose (ED50) of morphine administered in combination with Δ9-THC is 3.6 times lower than the ED50 of morphine alone. Co-administration of a cannabinoid with an opioid analgesic may also exhibit synergistic activity, with increased analgesic efficacy and/or reduced side effects seen relative to either drug administered as a monotherapy.

The cannabinoid may also be co-administered with olivetol or olivetol analog having the structure of formula (AA), as an anti-inflammatory formulation. Such a combination formulation can be readily synthesized using the present methods, particularly the method of Part A of Section III, by using an excess of compound (AA). In a telescoped reaction, where the synthesis of (AA) is immediately followed by cannabinoid synthesis, the initial reaction would be carried out with an excess of phloroglucinol or a phloroglucinol analog having the structure (AA-1).

Active agents that may be beneficial to co-administer with the cannabinoid are, therefore, as follows:

Analgesic agents, which include opioid analgesics such as alfentanil, buprenorphine, butorphanol, codeine, drocode, fentanyl, hydrocodone, hydromorphone, levorphanol, meperidine, methadone, morphine, nalbuphine, oxycodone, oxymorphone, pentazocine, propoxyphene, sufentanil, and tramadol; and nonopioid analgesics such as apazone, etodolac, diphenpyramide, indomethacin, meclofenamate, mefenamic acid, oxaprozin, phenylbutazone, piroxicam, and tolmetin;

NSAIDs, including propionic acid derivatives such as ketoprofen, flurbiprofen, ibuprofen, naproxen, fenoprofen, benoxaprofen, indoprofen, pirprofen, carprofen, oxaprozin, pranoprofen, suprofen, alminoprofen, butibufen, fenbufen and tiaprofenic acid; acetylsalicylic acid; apazone; diclofenac; difenpiramide; diflunisal; etodolac; flufenamic acid; indomethacin; ketorolac; meclofenamate; mefenamic acid; nabumetone; phenylbutazone; piroxicam; salicylic acid; sulindac; tolmetin; oxicams such as meloxicam and piroxicam; nabumetone; phenylbutazone; piroxicam; salicylates such as salsalate and acetylsalicylic acid; sulfasalazine; sulindac; tolmetin; and COX-2 inhibitors such as celecoxib, rofecoxib, and valdecoxib;

Steroidal anti-inflammatory agents, including corticosteroids of varying potency, such as hydrocortisone, hydrocortisone-21-monoesters (e.g., hydrocortisone-21-acetate, hydrocortisone-21-butyrate, hydrocortisone-21-propionate, hydrocortisone-21-valerate, etc.), hydrocortisone-17,21-diesters (e.g., hydrocortisone-17, 21-diacetate, hydrocortisone-17-acetate-21-butyrate, hydrocortisone-17,21-dibutyrate, etc.), alclometasone, dexamethasone, flumethasone, prednisolone, and methylprednisolone;

Active agents for the treatment of drug withdrawal, such as buprenorphine, methadone, and alpha 2 adrenergic agonists such as lofexidine and clonidine; and Active agents for the treatment of PTSD, such as antidepressants, benzodiazepines, prazosin, psilocybin, and glucocorticoids.

Pharmaceutical formulations of the invention thus include, without limitation, any of the novel cannabinoids of the invention, including those of formulae (EE), (EE-1), (FF), (FF-1), (GG), (GG-1), (HH), and (HH-1), present in an effective amount and in combination with at least one pharmaceutically acceptable excipient appropriate for a particular formulation type or dosage form.

It is to be understood that while the invention has been described in conjunction with a number of specific embodiments, the foregoing description as well as the examples that follow are intended to illustrate and not limit the scope of the invention.

All patents, patent publications, literature references, and other materials cited herein are incorporated by reference in their entireties.

Abbreviations used in the following examples:

ACE: acetone

DCE: dichloroethane

DCM: dichloromethane

DMAP: dimethylaminopyridine

EtOAc: ethyl acetate

Fe(acac)$_3$: ferric acetylacetonate

HPLC: high pressure liquid chromatography

NTBE: methyltributyl ether

NMP: N-methylpyrrolidone

THF: tetrahydrofuran

TLC: thin layer chromatography p-TsCl: p-toluenesulfonyl chloride

Example 1: Synthesis of Olivetol (a) Synthesis of 1,3,5-tris-p-toluenesulfonylbenzene:

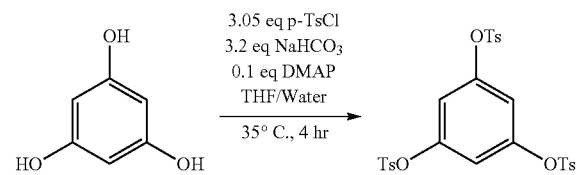 [SMILES: Oc1cc(O)cc(O)c1 ; Cc1ccc(S(=O)(=O)Oc2cc(OS(=O)(=O)c3ccc(C)cc3)cc(OS(=O)(=O)c3ccc(C)cc3)c2)cc1]

Phloroglucinol (100 g) was dissolved in a THF/water mixture (4 V/14 V) in a flask equipped with a mechanical stirrer and under a nitrogen blanket. Nitrogen gas was bubbled through the solution for 30 minutes to degas. Next, NaHCO$_3$ (3.2 equiv), p-TsCl (3.05 equiv), and DMAP (0.1 equiv) were added while stirring, creating a clear yellow solution with white solids. The reaction mixture was brought to 35° C. and maintained at that temperature. The reaction was monitored using TLC (70:30 hexane/EtOAc) and HPLC. Additional NaHCO$_3$ was added as the pH decreased (total 3.4 equiv. of NaHCO$_3$). After about four hours, when the reaction was deemed complete, the aqueous layer was separated and checked for product loss (0.15%) while the organic layer was washed twice with 5 V (1:1) water/brine solution. The filtrate was also checked for product loss (0.03%). Organic solution was stripped until a thick slurry formed, to which 3 V heptane was added to further precipitate product while agitating for 1 hour before vacuum filtering and washing with 1 V heptane. The white crude solid obtained was dried for 24 hours to produce 392.8 g final product, 1,3,5-tritosylatebenzene (i.e., fully tosylated phloroglucinol). NMR and HPLC indicated an 84.2% yield of the desired product with 98.6% purity.

(b) Alkylation of 1,3,5-tritosylatebenzene:

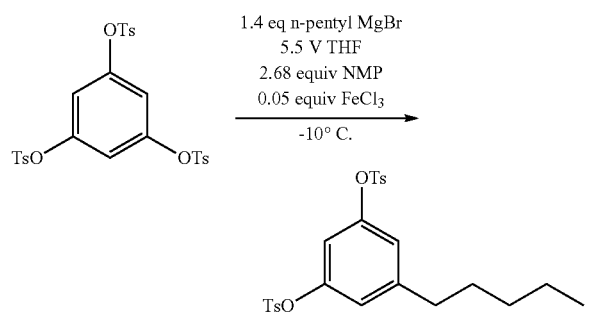

1,3,5-tritosylate benzene (75 g) and dry/degassed THF (7.75 V) were added to a jacketed flask which was equipped with a mechanical stirrer and an addition funnel (3×vac/N₂ cycles applied) to form a clear solution. To the solution, FeCl₃ (0.05 equiv) and dry NMP (4.75 equiv) were added under nitrogen, forming a red solution. The solution was cooled to −13° C./−15° C. and sparged with nitrogen. 2M n-pentyl-MgBr (1.4 equiv.) was slowly charged through the addition funnel. The reaction solution was stirred for 1 hr at −10° C. and reaction completion was monitored by HPLC; the solution was then stirred overnight at −10° C. Then, the reaction solution was diluted with MTBE (5 V) and quenched with 1N HCl (1.3 equiv.) at 0° C. The jacket temperature was then gradually increased to ambient temperature and stirred for about 30 min. The organic layer was separated out from the aqueous layer. Both layers were checked by HPLC, and since the aqueous layer did not contain any product, the aqueous layer was not further extracted. The organic product solution was successively washed with 10% NaHCO₃ (8 V), H₂O (8 V), and brine (8 V). The washed organic layer was concentrated on a rotary evaporator at 35° C. to give crude 5-pentyl-1,3-phenylene bis(4-methylbenzensulfonate) as an orange oil. Crystallization of the oil was attempted using THF/heptanes; however, a two-layer mixture was obtained. The solution was stripped and co-stripped with heptanes (1.6 V) to yield an orange-red color solid. The solid was dried at room temperature under high vacuum to give approximately 52 g of the solid product, ditosylated olivetol (9). HPLC indicated an approximately 86.3% product conversion.

(c) Detosylation of ditosylated olivetol:

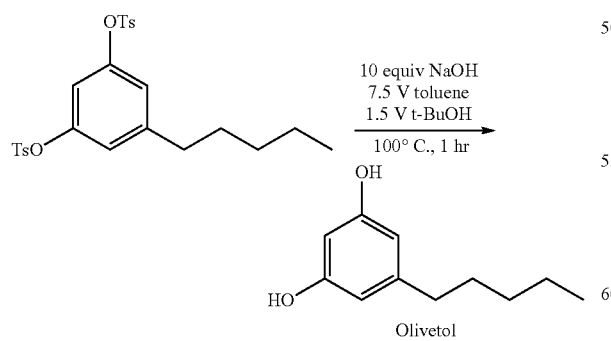

5-pentyl-1,3-phenylene bis(4-methylbenzenesulfonate) (ditosylated olivetol, 190 g) was dissolved in toluene (8.5 V) and t-butanol (1.5 V). in a three-necked round bottom flask equipped with a mechanical stirrer, a 12-inch condenser, and under a nitrogen atmosphere. Solid NaOH (9 equiv.) were added, forming a slurry. The solution was then refluxed at 100° C. with a condenser set up at −8° C. and allowed to stir until the reaction was deemed complete by TLC (50:50 hexane/EtOAc) and HPLC, approximately 1 hr. The solution was then allowed to cool to ambient temperature, water (4 V) was added, and the solution stirred for about 1 hr. The layers were separated and the aqueous product layer was washed with 300 mL toluene. To the aqueous product solution in an ice bath, isopropyl acetate (3 V) and 32% HCl (10 equiv) were added and agitated for 30 minutes. The layers were separated, and the organic layer was washed with water four times to remove all water-soluble impurities (1 V). The layers were separated, and the combined organic product layer was concentrated using a rotary evaporator while co-stripping with heptane twice (approximately 2 V) to produce crude olivetol oil in solution. The olivetol oil (68 g) was provided at a purity level of 97.5%.

Example 2: Alternative Synthesis of Olivetol (a) Synthesis of 1,3,5-tris-p-toluenesulfonylbenzene

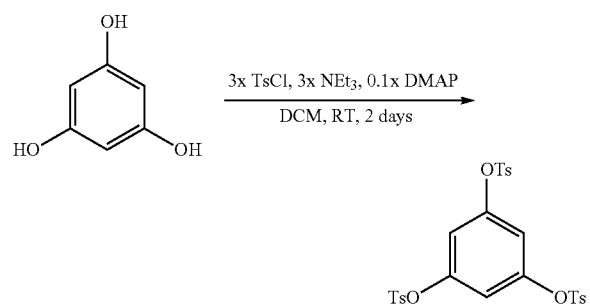

In a round bottom flask, phloroglucinol (1.30 g, 10.3 mmol) and triethylamine (5.4 mL, 39 mmol, 3 equiv.) were stirred in DCM (45 mL) for 10 minutes. The flask was placed in a cold-water bath and tosyl chloride (7.44 g, 39 mmol, 3 equiv.) was added in portions before the addition of DMAP (0.159 g, 1.3 mmol, 0.1 equiv.). The flask was left to stir over 2 days before being washed with brine, dried over Na₂SO₄, and concentrated on rotary evaporator (water bath 30° C.) to afford a brown oil (6.06 g). The oil was subjected to liquid column chromatography (70:30 to 50:50 hexanes: EtOAc) to give a colorless oil which crystallized as a white powder (4.9 g).

(b) Synthesis of 5-pentyl-1,3-phenylene bis(4-methylbenzenesulfonate)

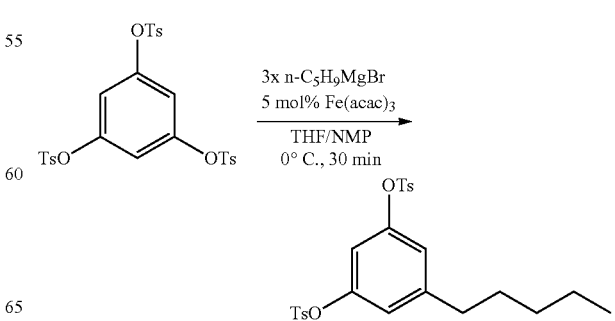

Two small crystals of $I_2$ were added to a room temperature THF (5 mL) suspension of Mg turnings (0.303 g, 12.61 mmol, 1.2 equiv.) in a dry 50 mL 3 neck flask fitted with a condenser. Reaction was placed under argon. A syringe containing THF (3.75 mL) solution of 1-bromopentane (1.52 g, 10.08 mmol, 1 equiv.) was ready to add to the reaction. 10-15% of the 1-bromopentane solution was added and the mixture was heated at reflux to initiate the reaction (<5 min). After initiation, the reaction mixture was removed from the heat and the remainder of the linoleyl bromide solution was added dropwise over approximately one hour, at which point the reaction mixture had taken on a brownish grey color and a significant portion of the Mg turnings had been consumed. Upon completion of the addition, the reaction mixture was stirred for a further hour resulting in 1 M solution of 1-pentylmagnesium bromide.

In an oven dried 50 mL round bottom flask, 1,3,5-tritosylatebenzene (1.30 g, 2.21 mmol. 1 equiv.) was dissolved in 5 mL of dry THE and 0.5 mL of dry NMP. To the reaction, $Fe(acac)_3$ (0.04 g, 0.11 mmol, 0.05 equiv.) was added resulting in a homogenous orange solution. Reaction was placed under argon and cooled to 0° C. with an ice bath. Solution of the prepared 1 M 1-pentylmagnesium bromide (6.63 mL, 6.63 mmol, 3 equiv.) was added to the reaction mixture via syringe dropwise. Upon completion of the addition (15 minutes), reaction was stirred for further 30 minutes at 0° C. TLC (70:30 Hexanes/EtOAc) showed the complete consumption of starting material. Reaction was stopped and diluted with $Et_2O$ (15 mL) then carefully quenched with 0.5M HCl. (20 mL). Reaction mixture was extracted with $Et_2O$ (3×20 mL). Combined organic layers were washed with $NaHCO_3$ (1×50 mL) the $H_2O$ (1×50 mL), brine (1×50 mL), dried over $Na_2SO_4$ and concentrated on a rotary evaporator (water bath 35° C.) to afford crude 5-pentyl-1,3-phenylene bis(4-methylbenzenesulfonate) as a light yellow mixture of solid and oil. This crude product was subjected to liquid column chromatography (85:15 Hexanes/EtOAc) to give 0.823 g of desired product.

(c) Synthesis of Olivetol

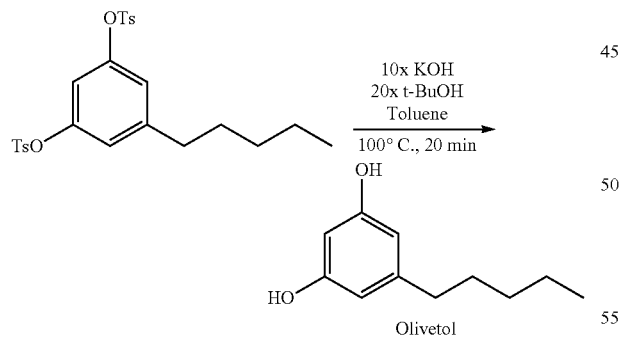

Olivetol

In a 25 mL round bottom flask, 5-pentyl-1,3-phenylene bis(4-methylbenzenesulfonate) (0.094 g, 0.192 mmol, 1 equiv.) was dissolved in toluene (2.0 mL). To the reaction flask, t-BuOH (0.5 mL, 0.355 g, 3.85 mmol, 20 equiv.) and crushed KOH (0.107 g, 1.92 mmol, 10 equiv.) were added. A condenser was attached to the reaction flask and reaction was placed under argon. As reaction was heated to 100° C. (refluxing), brown solid appeared in the reaction flask. After 20 minutes of refluxing, TLC (1:1 hexanes/EtOAc) showed the consumption of the starting material. Reaction was stopped and solvent was removed by rotary evaporation. Reaction residue then was redissolved in EtOAc (5 mL) and washed with 1M HCl (5 mL). Reaction mixture was extracted with EtOAc (3×5 mL). Combined organic layers were dried over $Na_2SO_4$ and concentrated on rotary evaporator (water bath 35° C.) to afford crude 5-pentylbenzene-1,3-diol as black oil. The crude product was subjected to liquid column chromatography (70:30 hexanes/EtOAc) to give 0.033 g of the desired product.

Example 3: Synthesis of Divarinol from Phloroglucinol (a) The method of Example 1, part (a), was repeated to synthesize 1,3,5-tritosylate benzene from phloroglucinol.

(b) The method of Example 1, part (b) is repeated, substituting n-propyl-MgBr for N-pentyl-MgBr:

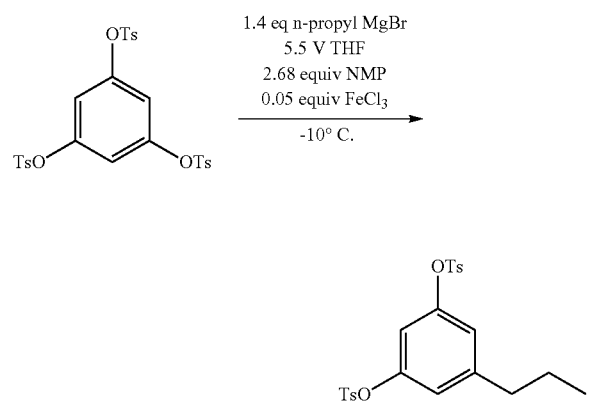

The resulting product is 5-propyl-1,3-phenylene bis(4-methylbenzenesulfonate), expected at a yield of greater than 90% and substantially free of contaminants. The compound may be isolated and purified or used as is in the next step.

(c) The method of Example 1, part (c) is repeated, except that the reaction product of the preceding step is substituted for ditosylated olivetol:

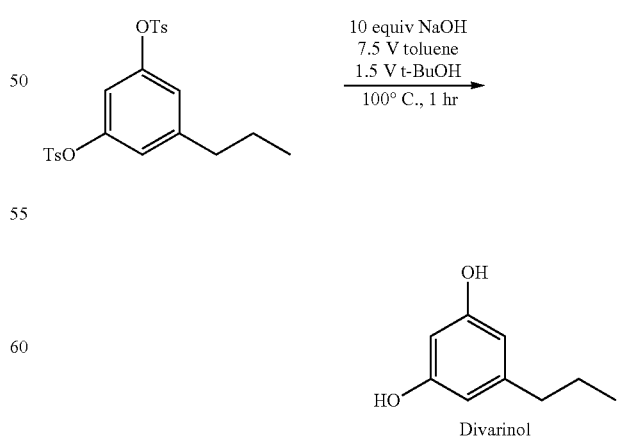

Divarinol

The final reaction product is divarinol, as indicated in the scheme.

Example 4: Synthesis of CBD from Olivetol Using Alumina

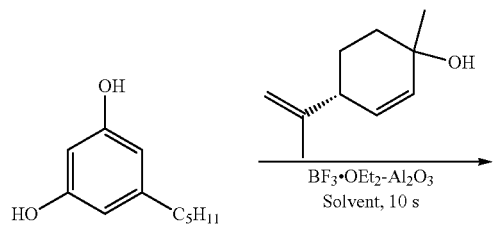

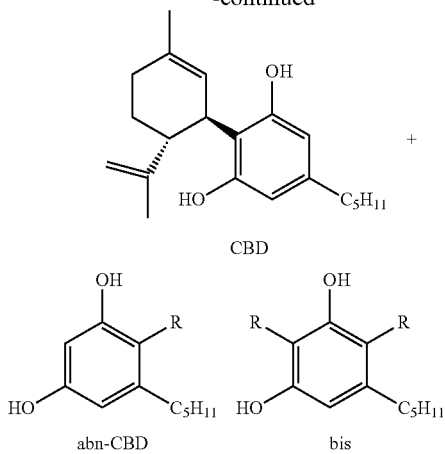

To a flame-dried 20 mL vial was added basic alumina (0.375 g, 3.68 mmol, 24.5 eq.), dry 1,2-dichloroethane (5.6 mL) and dry heptane (1.9 mL), and the solution was placed under argon. BF$_3$·Et$_2$O (0.056 mL, 0.45 mmol, 3 eq.) was added, and the suspension was allowed to stir for 15 minutes, then boiled for 1 minute. A mixture of olivetol (0.0811 g, 0.45 mmol, 3 eq.) and (1S,4R)-p-mentha-2,8-dien-1-ol (0.023 g, 0.15 mmol, 1 eq.) in dry 1,2-dichloroethane (1.5 mL) and dry heptane (0.5 mL) was added to the boiling suspension, and the reaction was quickly quenched with aqueous saturated NaHCO$_3$ (4 mL) within 10 seconds. Et$_2$O (20 mL) and additional saturated NaHCO$_3$ (20 mL) was added. The organic layer was washed with brine, dried over Na$_2$SO$_4$, and concentrated in vacuo. The product was purified via column chromatography (10:88:2 EtOAc/hexanes/Et$_3$N) to afford 0.0285 g of the desired product.

The ratio of CBD to olivetol in the final product was approximately 1:0.62. Washing with hot water to dissolve the remaining olivetol resulted in a CBD-to-olivetol ratio of 1:0.32, and washing an additional time resulted in a CBD-to-olivetol ratio of 1:0.

Examples 5-12

Additional Syntheses of CBD from Olivetol Using Alumina

The reaction of Example 4 was repeated using different reaction temperatures and solvents as indicated in Table 4 below, and the relative amounts of CBD, abn-CBD, and bis obtained are provided, as is the ratio of CBD to THC in the final product:

TABLE 4

| Example No. | Solvent | Temp, °C. | CBD:abn-CBD:bis | CBD:THC |
|---|---|---|---|---|
| 5 | DCM | 40 | 1:0.4:0.27 | 1:0 |
| 6 | Cyclohexane | 80 | 1:1.24:0 | 1:0 |
| 7 | 1:1 Cyclohexane/DCM | 40 | 1:0.63:0.25 | 1:0 |
| 8 | 1:1 Cyclohexane/DCE | 80 | 1:0.34:0.13 | 1:0 |
| 9 | 25% Heptane/DCE | 80 | 1:0.17:0.08 | 1:0 |
| 10 | 50% Heptane/DCE | 80 | 1:0.39:0.20 | 1:0 |
| 11 | 1-Chlorobutane | 80 | 1:0.27:0.16 | 1:0 |
| 12 | 25% Methylcyclohexane/1-chlorobutane | 80 | 1:0.65:0.28 | 1:0 |

The results indicate that a reaction product composition can be obtained with a mol ratio of CBD to abn-CBD of greater than 1:0.20 and a mol ratio of CBD to bis greater than 1:0.10.

Example 13: Synthesis of CBD from Olivetol Using Only Boron Trifluoride

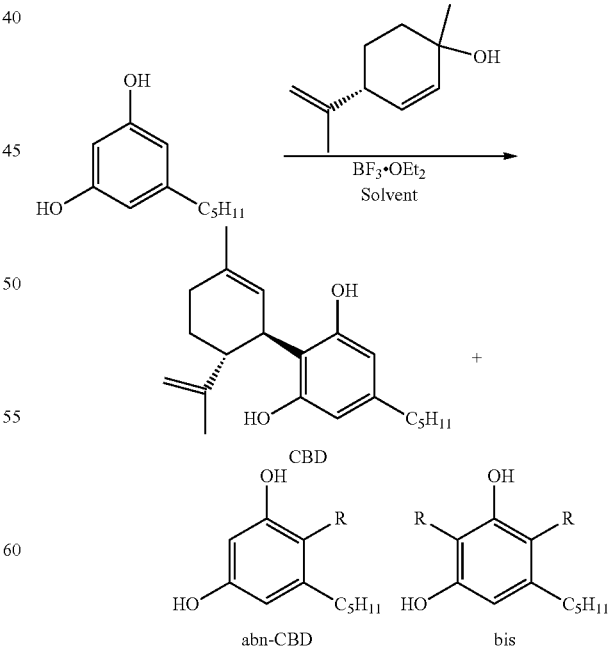

To a flame-dried 20 mL vial was added olivetol (54 mg, 0.45 mmol, 1 eq.) and (1S,4R)-p-mentha-2,8-dien-1-ol (45 mg, 0.3 mmol, 1 eq.) in dry 1,2-dichloroethane (0.75 mL) and the reaction mixture was heated to 80° C. BF$_3$·OEt$_2$ (2 mol %) in 1,2-dichloroethane (0.05 mL) was then added over 10 minutes. The reaction was quenched with aqueous saturated NaHCO$_3$ (0.5 mL). The organic layer was separated, dried over Na$_2$SO$_4$, and concentrated in vacuo. The product was analyzed by $^1$H NMR spectroscopy. The yield of CBD obtained was 31% and the reaction product composition was determined to be 1:1:0.5 CBD/abn CBD/bis.

Examples 14-18: Synthesis of CBD from Olivetol Using Only Boron Trifluoride

The process of Example 13 was repeated using different solvents, different concentrations, different reaction temperatures, and different quantities of BF$_3$·OEt$_2$, as indicated in Table 5 along with the results obtained ("Conc" refers to the amount solvent compared to 1 equivalent of CBD in the reaction, at a 100% theoretical yield):

TABLE 5

| Example No. | BF$_3$·OEt$_2$ equiv | Solvent | Conc. | CBD yield Product composition |
|---|---|---|---|---|
| 14 | 0.1 | DCM | 10 V | 25% CBD 1:1.7 CBD/abn CBD |
| 15 | 0.1 | DCM | 10 V | 11% CBD 1:2.3 CBD/abn CBD |
| 16 | 0.02 | DCE | 10 V | 31% CBD 1:1:0.5 CBD/abn CBD/bis |
| 17 | 0.02 | DCE/heptane | 10 V | 30% CBD 1:1.3:0.2 CBD/abn CBD/bis |
| 18 | 0.02 | 10% ACE in DCE | 10 V | 1:1.7:0.75 CBD/abn CBD/bis |

Example 19: Synthesis of CBD from Olivetol Using Alumina and MgSO$_4$

To an oven-dried 3-neck 10 mL round-bottom flask fitted with an oven-dried condenser was added olivetol (0.541 g, 3 mmol, 2 equiv.), anhydrous alumina (0.091 g, 0.9 mmol, 0.6 equiv.), anhydrous MgSO$_4$ (0.361 g, 3 mmol, 2 equiv.), and anhydrous dichloroethane (4.5 mL). The mixture was placed under argon, and BF$_3$·Et$_2$O (0.019 mL, 0.15 mmol, 0.1 equiv.) was added. The suspension was stirred at room temperature for 15 minutes, then heated to 90° C. for 2 minutes. A solution of (1S,4R)-p-mentha-2,8-dien-1-ol (0.228 g, 1.5 mmol, 1 equiv.) in dichloroethane (0.5 mL) was added over 2.5 minutes to the boiling mixture. The reaction was then refluxed for 15 minutes before quenching with saturated aqueous NaHCO$_3$ and diluting with DCM. The organic layer was washed with brine, dried over Na$_2$SO$_4$, and concentrated in vacuo. Upon refluxing the reaction mixture for 30 minutes prior to quenching, $^1$H NMR indicated that no olivetol was present.

Example 20: Synthesis of CBD from Olivetol Via the Protecting Group Method

Synthesis of dimethoxyolivetol:

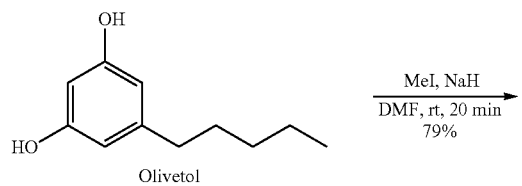

Olivetol

MeI, NaH
DMF, rt, 20 min
79%

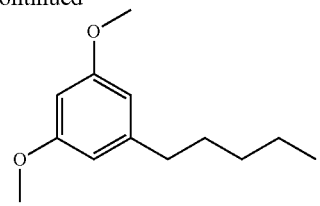

To a flame-dried 100 mL round bottom flask, NaH (1.00 g, 25 mmol) and anhydrous DMF (30 mL) were added and the mixture was placed under argon and cooled to 0°c. Olivetol (1.80 g, 1.0 mmol) in anhydrous DMF (10 mL) was added, and the mixture was allowed to stir for 5 minutes. Methyl iodide (1.9 mL, 30 mmol) was added dropwise, and the ice bath was removed. The reaction was allowed to stir for 20 minutes, and then quenched with 3.0 M HCl (30 mL). The mixture was extracted with ethyl acetate, and the organic layer was washed with water and brine, dried over Na$_2$SO$_4$, and concentrated under reduced pressure, yielding a dark brown oil. The product was purified via column chromatography (5% EtOAc/Hex) in 79% yield as a clear, yellow oil.

(b) Synthesis of Dimethoxy CBD, 0.3 Mmol Scale:

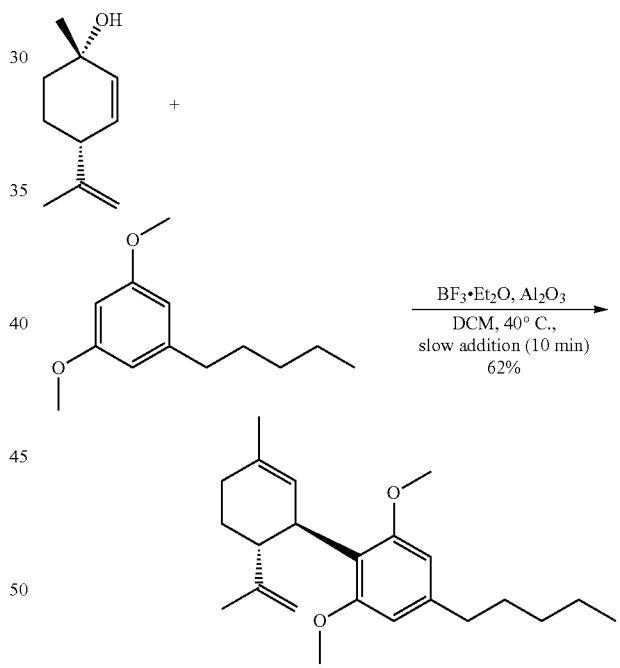

To a flame-dried 100 mL round bottom flask, basic alumina (0.749 g, 7.35 mmol) and anhydrous DCM (5.5 mL) were added. The mixture was placed under argon, and BF$_3$·Et$_2$O (0.11 mL, 0.9 mmol) was added. The suspension was stirred for 15 minutes, then heated to 40° C. and stirred for 1 minute. Dimethoxyolivetol (0.0625 g, 0.3 mmol) in anhydrous DCM (2 mL) was added, and the mixture was stirred for 1 minute. (1S,4R)-p-mentha-2,8-dien-1-ol (0.0457 g, 0.3 mmol) in anhydrous DCM (2 mL) was added dropwise over 10 minutes, and the reaction was then stirred for 1 minute. The reaction was quenched with 4 mL saturated NaHCO$_3$, extracted with diethyl ether, washed with brine, dried over Na$_2$SO$_4$, and concentrated under reduced pressure. The product was purified via column chromatography (5% EtOAc/Hexane) in 62% yield as a clear, colorless oil.

(b) Synthesis of Dimethoxy CBD, 1.0 Mmol Scale:

To a flame-dried 100 mL round bottom flask, basic alumina (2.50 g, 24.5 mmol) and anhydrous DCM (18 mL) was added. The mixture was placed under argon, and $BF_3$-$Et_2O$ (0.37 mL, 3 mmol) was added. The suspension was stirred for 15 minutes, then heated to 40° C. and stirred for 1 minute. Dimethoxyolivetol (0.208 g, 1.0 mmol) in anhydrous DCM (6.5 mL) was added, and the mixture was stirred for 1 minute. (1S,4R)-p-mentha-2,8-dien-1-ol (0.152 g, 1 mmol) in anhydrous DCM (6.5 mL) was added dropwise over 10 minutes, and the reaction was then stirred for 1 minute. The reaction was quenched with 30 mL saturated $NaHCO_3$, extracted with 30 mL diethyl ether, washed with brine, dried over $Na_2SO_4$, and concentrated under reduced pressure. The product was purified via column chromatography (100% Hexane) in 34% yield as a clear, colorless oil.

(c) Synthesis of CBD:

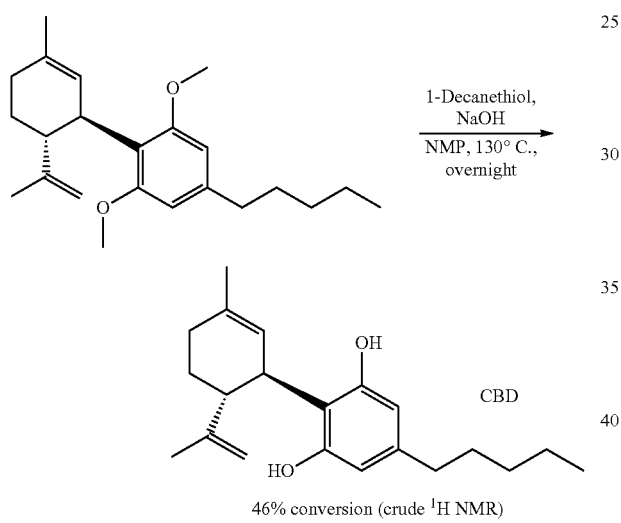

46% conversion (crude $^1$H NMR)

To a flame-dried 4 mL vial, dimethoxy-CBD (0.051 g, 0.15 mmol), NaOH (0.072 g, 1.8 mmol), and NMP (0.6 mL) were added. The mixture was placed under nitrogen, and decanethiol (0.16 mL, 0.75 mmol) was added. The reaction was heated to 130° C. and stirred overnight. The reaction was quenched with 1.0 M HCl (10 mL), extracted with ethyl acetate, washed with water and brine, dried over $Na_2SO_4$, and concentrated under reduced pressure.

Example 21: Synthesis of THCV from Phloroglucinol Via Divarinol

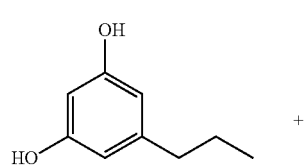

+

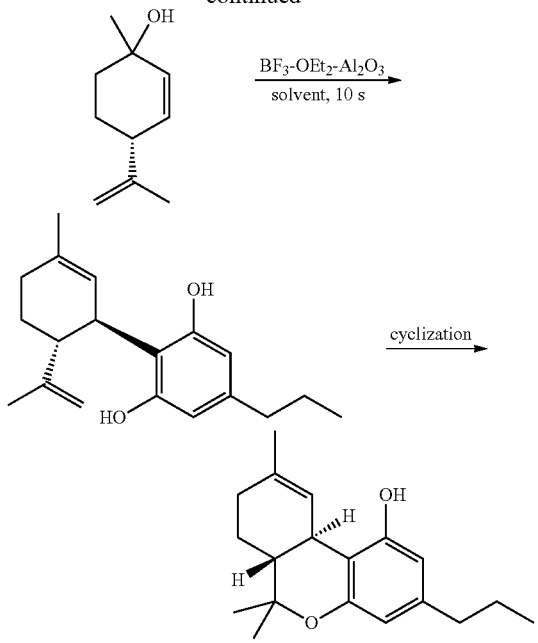

(a) The method of Example 3 was followed to prepare divarinol from phloroglucinol.
(b) Then, the method of Example 4 was followed in which divarinol was substituted for olivetol as the co-reactant in the cross-coupling reaction with (1S,4R)-p-mentha-2,8-dien-1-ol (0.023 g, 0.15 mmol, 1 eq.).
(c) Cyclization of the intermediate obtained in (b) is carried out using a Lewis acid and a molecular sieve or other means that will be apparent to those skilled in the art and/or are described in the literature.

Example 22: Synthesis of CBD Analog with 4'-(2-Ethylaminoethyl) Substituent

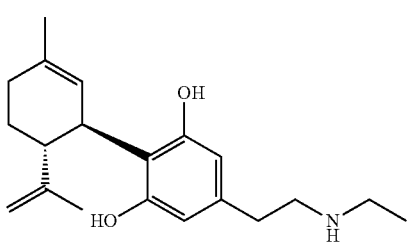 [SMILES: C=C(C)[C@@H]1CCC(C)=C[C@H]1c1c(O)cc(CCNCC)cc1O]

(a) The reaction below was carried out to provide pivaloyl protection on the hydroxyl groups of the reactant:

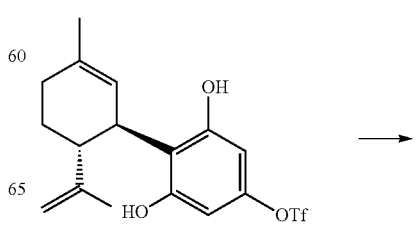

-continued

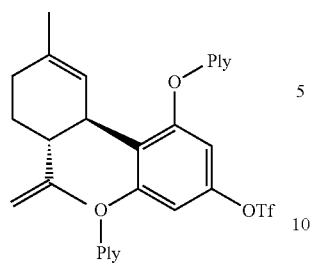

Reaction conditions were as follows: Pivaloyl chloride (2.5 eq), DMAP, 3.0 (equiv.), MeCN, 0° C., 16 hrs. The identity of the product (2.10 g, 73%) was characterized by ¹H NMR and MS.

(b) The C-4' site of the pivaloyl-protected intermediate synthesized was then modified to provide the 4'-ethoxyethenyl group using the reaction of the following scheme:

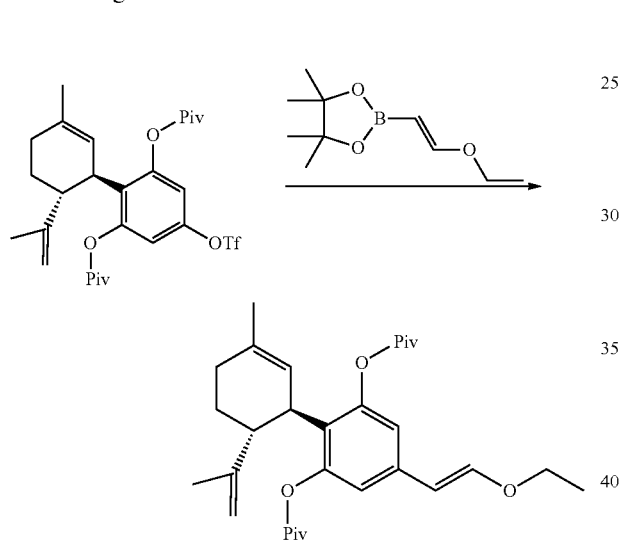

Reaction conditions (500 mg scale): 500 mg of the pivaloyl-protected intermediate (1.1 equiv.), Na$_2$CO$_3$ (2.0 equiv.), PdCl$_2$(dppf)·dcm (0.05 equiv.), 1,4-dioxane, 110° C., 1 h. The reaction product (140 mg, 33%) was characterized by ¹H NMR and MS.

Next, the compound obtained was converted to the aldehyde as shown:

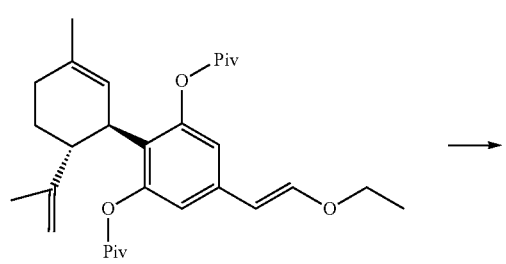

-continued

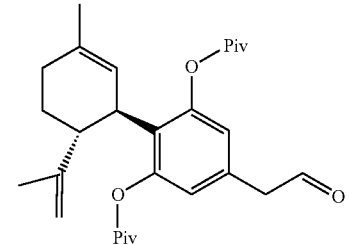

Reaction conditions: 4M HCl (5 equiv), 1,4-dioxane, toluene, 50° C., 1 hr.

A reductive amination reaction using ethylamine was then used to transform the aldehyde intermediate to the 4-(2-ethylaminoethyl) compound, followed by removal of the pivaloyl protecting groups using conventional means to provide the desired reaction product. The reactions are illustrated below:

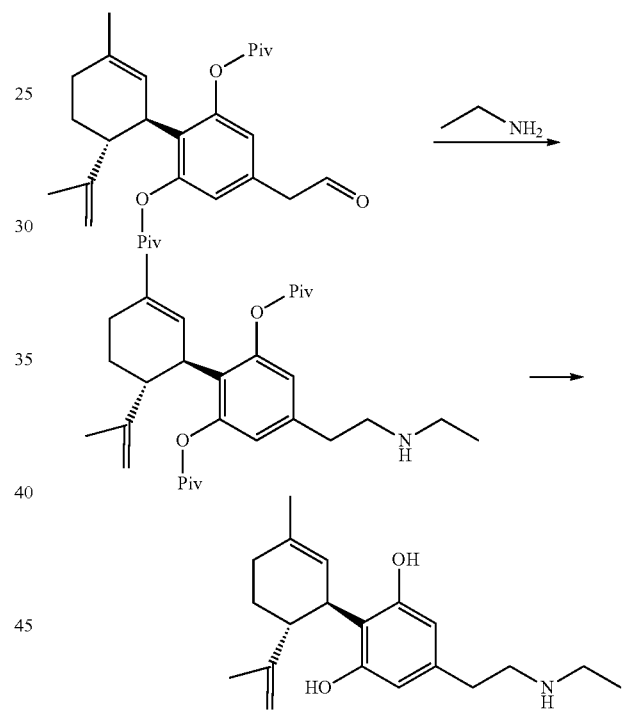

Reaction conditions: Ethylamine (1.1 equiv.), NaCNBH$_3$ (2.0 equiv.), MeOH, room temp., 16 hr.

Example 23: Synthesis of CBD Analog with 4'-(2-(n-Propyl)aminoethyl) Substituent

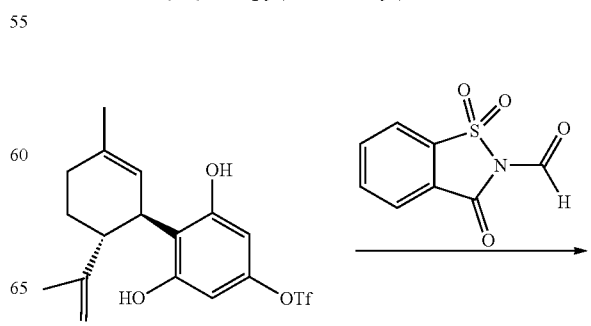

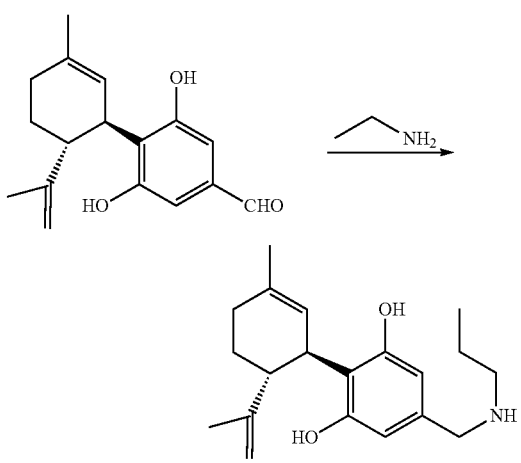

Reagents and reaction conditions, first step: Starting material (1.5 equiv.), Pd(OAc)$_2$ (0.05 equiv.), dppf (0.075), triethylsilane (1.3 equiv.), Na$_2$CO$_3$ (1.5 equiv.), ACN, 80° C., 16 hr. Product characterized by $^1$H NMR and MS, yield 400 mg (30%).

Reagents and reaction conditions, second step: aldehyde intermediate (1.1 equiv.), NaCNBH$_3$ (2.0 equiv.), MeOH, room temperature, 16 hr. Product characterized by $^1$H NMR and MS, yield 40 mg (97% purity as determined by HPLC).

Example 24: Synthesis of CBN Analog with 4'-(2-Ethoxyethyl) Substituent

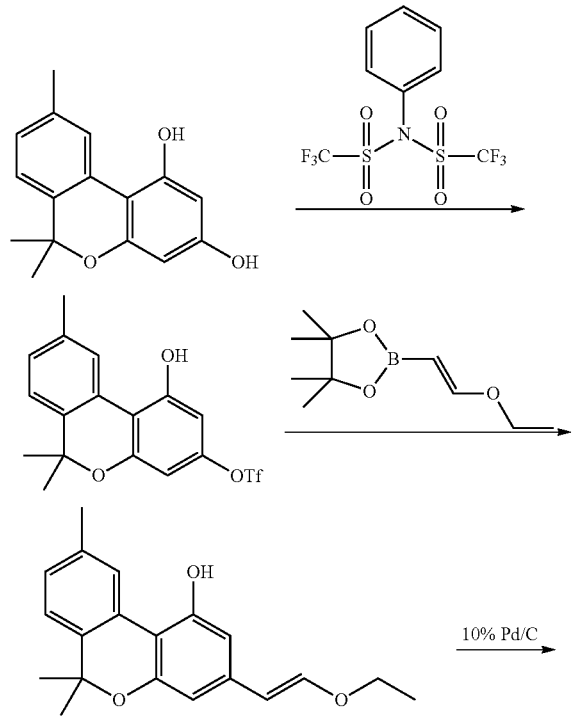

Reagents and reaction conditions, step (1): starting material (1.5 equiv.), Na$_2$CO$_3$ (2.0 equiv.) PdCl$_2$(dppf)·DCM (0.03 equiv.), 1,4-dioxane, H$_2$O, 90° C., 16 h, sealed tube. Product characterized by UPLC and $^1$H NMR, yield 200 mg (46%).

Reagents and reaction conditions, step (2): Pd(C), hydrogen, ethanol, room temperature. Product characterized by $^1$H NMR, MS, HPLC, 2D NMR, yield 80 mg (80%).

Example 25: Synthesis of CBN Analog with 4'-(2-Morpholinoethyl) Substituent

Conversion of the compound synthesized in Example 24 to CBN Target 3

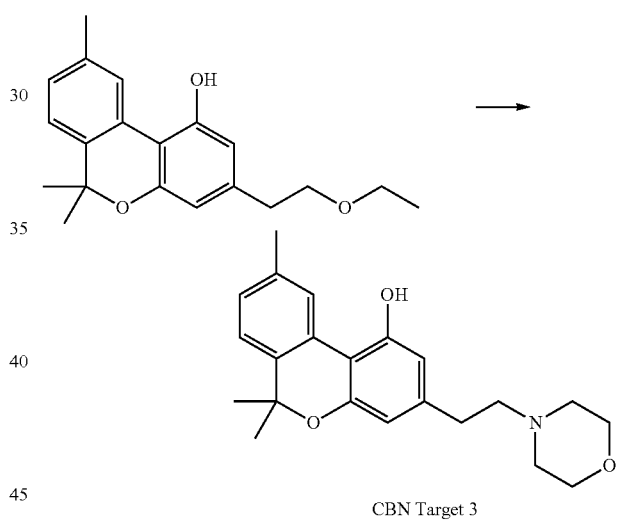

CBN Target 3 as follows:

Reagents and Reaction conditions: starting material (1.5 equiv.), dioxane, HCl, toluene, 50° C., 30 min.

Example 26: Telescoped Olivetol Synthesis

Step 1:

Phloroglucinol (50 g, 396 mmol, 1 equiv.) was dissolved in THF (700 mL, 14 V) and water (200 mL, 4 V) in a three-neck jacketed flask equipped with a mechanical stirrer under a nitrogen atmosphere.

Next, NaHCO$_3$ (119.91 g, 1.43 mol, 3.2-3.6 equiv.), DMAP (4.84 g, 39.6 mmol, 0.1 equiv.) and p-TsCl (230.55 g, 1.21 mol, 3.05 equiv.) were charged, creating a clear yellow solution with white solids. The reaction mixture was heated to 35° C. and maintained at that temperature while stirring for four hours until deemed complete by TLC and HPLC, left to stir overnight.

After reaction was deemed complete, the aqueous layer was separated and checked for product loss by HPLC. The organic product layer was washed twice with 1:1 water/brine solution (250 mL, 5 V). Aqueous washes were also checked for product loss. Organic layer was stripped until a thick slurry/semi-solid is formed, to which THF (200 mL, 4 V) was charged and co-stripped until the KF measures less than 0.02% water content. Then, solvent swap was needed (Toluene to THF) to remove toluene. After removal of water from the solution, the reaction product in THF, fully tosylated phloroglucinol, was carried to the next step.

Step 2:

1,3,5-tritosylate benzene (230 g, 391 mmol, 1 equiv.) and dry/degassed THF (1265 mL, 5.5 V) were charged into an RB flask. KF and contain of the solution were checked. Then solution was transferred into a jacketed flask (3 times vac/$N_2$ cycles applied) through a cannula which was equipped with a mechanical stirrer under a nitrogen atmosphere to form a light-yellow solution.

$FeCl_3$ (3.17 g, 19.5 mmol, 0.05 equiv.) and DMPU (126.5 mL, 0.55 V) were charged under $N_2$ atm forming a colored solution. Solution was purged with nitrogen again. The solution was cooled down to −10 to −13° C. internal temperature with the glycol chiller set to −15° C.

2M n-PentylMgBr (244 mL, 488 mmol, 1.25 equiv.) was slowly charged through an addition funnel over approximately 7.5 hours). More n-PentylMgBr was charged after the first reaction check since starting material was still present (12 mL, 0.061 equiv). Once the reaction was deemed complete, MTBE (575 mL, 2.5 V) and 1M HCl (586 mL, 586 mmol, 1.5 equiv.) were charged and allowed to stir for 30 minutes. Layers were separated and aqueous layer were washed with MTBE (575 mL, 2.5 V). Organic layers were combined then were washed twice with 10% w/w $NaHCO_3$, water and brine (575 mL, 2.5 V each wash). The organic solution was then stripped to form a thick oil and co-stripped with Toluene (285 mL, 1.25 V).

The crude oil was carried forward to next reaction, Step 3.

Step 3:

Ditosylated olivetol (5-pentyl-1,3-phenylene bis(4-methylbenzenesulfonate)) from Step 2 (190.0 g, 388 mmol, 1 equiv.)(estimated crude Step 2 qty) was dissolved in toluene (1615 mL, 8.5 V) and t-BuOH (285 mL, 1.5 V) in a three necked round bottom flask equipped with a mechanical stirrer, a 12-inch condenser and under a nitrogen atmosphere.

NaOH (139.9 g, 3.49 mol, 9 equiv.) was then charged, forming a slurry. The slurry was then refluxed at 100° C. with a condenser set up at −8° C. and allowed to stir until deemed complete, approximately one hour. The reaction was cooled down to ambient temperature.

Water (563 mL, 4V) was then charged and allowed to stir~1 hr. The layers were separated, and the aqueous product layer was washed with 300 mL toluene.

To the aqueous product solution in an ice bath, isopropyl acetate (570 mL, 3 V) and 32% HCl (349.9 mL, 3.49 mol, 10 equiv.) were charged and then agitated for 30 minutes.

The layers were separated, and the organic layer was washed with water four times to remove all water-soluble impurities (190 mL, 1 V). The layers were separated, and the combined organic product layer was concentrated using a rotary evaporator while co-stripping with Heptane twice (110 mL, ~2 V) to produce crude olivetol oil in solution.

The invention claimed is:

1. A method for synthesizing a cannabinoid, wherein the method comprises:

(a) reacting an optionally substituted phloroglucinol reactant having the structure

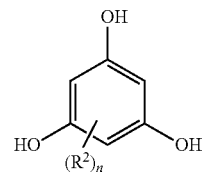

with an electron-withdrawing hydroxyl-protecting reagent under conditions effective to provide a first intermediate comprising a hydroxyl-protected compound having the structure

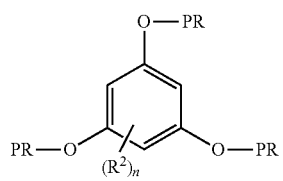

wherein n is zero, 1 or 2; $R^2$ is selected from $C_1$-$C_{12}$ alkyl, $C_1$-$C_{12}$ alkoxy, $C_2$-$C_{12}$ alkoxyalkyl, $C_1$-$C_{12}$ alkylsulfanyl, $C_2$-$C_{12}$ acyl, $C_2$-$C_{12}$ acyloxy, $C_2$-$C_{12}$ alkoxycarbonyl, $C_6$-$C_{18}$ aryloxycarbonyl, carboxyl, and halo; and PR is a hydroxyl-protecting group;

(b) effecting a cross-coupling reaction between the first intermediate and a reactant $R^1$-M in a solvent in the presence of a cross-coupling catalyst, wherein:

$R^1$ is selected from $C_1$-$C_{12}$ alkyl; ($C_1$-$C_8$ alkoxy)-substituted $C_1$-$C_{12}$ alkyl; $C_1$-$C_{12}$ alkyl substituted with N ($C_1$-$C_8$ alkyl)$_2$; $C_1$-$C_{12}$ alkyl substituted with $C_1$-$C_8$ alkylsulfonyl (—$SO_2$-alkyl); and $C_1$-$C_{12}$ alkyl substituted with oxanyl, morpholino, or diazinanyl, and M is selected from —Zn—X, —B(OH)$_2$, —B(OR)$_2$, —MgX and —CuLi in which X is halo and R is alkyl, thereby providing a second intermediate in which a protected hydroxyl group has been replaced with $R^1$, the second intermediate having the structure

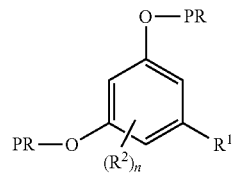

(c) hydrolyzing the second intermediate to remove the hydroxyl-protecting groups, thereby providing an $R^1$-substituted deprotected compound as a third intermediate having the

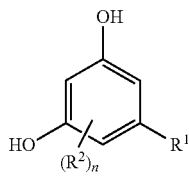

(d) contacting the $R^1$-substituted deprotected compound with a substituted cyclohexene reactant having the structure

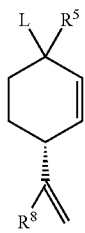

wherein $R^5$ is H, carboxyl, $C_2$-$C_6$ acyloxy, $C_2$-$C_6$ alkoxycarbonyl, $C_1$-$C_6$ alkyl, or $C_1$-$C_6$ alkyl substituted with hydroxyl, carboxyl, or halo; $R^8$ is methyl, hydroxymethyl, or halomethyl; and L is a leaving group, in the presence of a Lewis acid catalyst under reaction conditions effective to result in coupling of the $R^1$-substituted deprotected intermediate and the substituted cyclohexene reactant to provide a reaction product composition comprising a cannabinoid having the structure

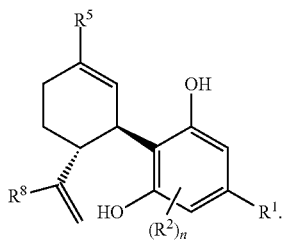

2. The method of claim 1, wherein $R^1$-M is $R^1$—MgBr, the cross-coupling catalyst is an iron-based catalyst, and the cross-coupling reaction is a Fürstner reaction carried out at a reaction temperature in the range of −25° C. to 25° C.

3. The method of claim 2, wherein about 1 equivalent to about 1.5 equivalents of $R^1$—MgBr are used and the reaction temperature in the range of −15° C. to −5° C.

4. The method of claim 1, wherein the first intermediate is not isolated or purified prior to the cross-coupling reaction of step (b).

5. The method of claim 1, wherein the third intermediate is not isolated or purified prior to step (d).

6. The method of claim 1, wherein $R^5$ and $R^8$ are methyl, so that the cannabinoid in the reaction product composition has the structure

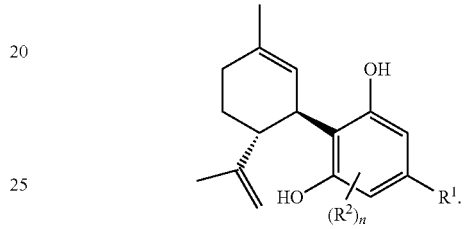

7. The method of claim 6, wherein n is zero.

8. The method of claim 7, wherein $R^1$ is n-pentyl, such that the $R^1$-substituted deprotected compound is olivetol and the cannabinoid is cannabidiol (CBD).

9. The method of claim 7, wherein $R^1$ is n-propyl, such that the $R^1$-substituted deprotected compound is divarinol.

10. The method of claim 8, wherein $R^1$ is n-pentyl and the method further comprises subjecting the cannabinoid to cyclization conditions.

11. The method of claim 6, wherein the electron-withdrawing hydroxyl-protecting reagent converts hydroxyl groups to sulfonate esters.

12. The method of claim 11, wherein the sulfonate esters are selected from tosylate, mesylate, triflate, benzyl sulfonate, 2-[(4-nitrophenyl) ethyl] sulfonate, and fluorosulfonate.

* * * * *